United States Patent
Watts et al.

(10) Patent No.: US 11,795,580 B2
(45) Date of Patent: Oct. 24, 2023

(54) MOLECULES FOR VERIFYING OLIGONUCLEOTIDE DIRECTED COMBINATORIAL SYNTHESIS AND METHODS OF MAKING AND USING THE SAME

(71) Applicant: Haystack Sciences Corporation, South San Francisco, CA (US)

(72) Inventors: Richard Edward Watts, South San Francisco, CA (US); Divya Kanichar, South San Francisco, CA (US)

(73) Assignee: Haystack Sciences Corporation, South San Francisco, CA (US)

( * ) Notice: Subject to any disclaimer, the term of this patent is extended or adjusted under 35 U.S.C. 154(b) by 70 days.

(21) Appl. No.: 16/608,478

(22) PCT Filed: May 1, 2018

(86) PCT No.: PCT/US2018/030536
§ 371 (c)(1),
(2) Date: Oct. 25, 2019

(87) PCT Pub. No.: WO2018/204420
PCT Pub. Date: Nov. 8, 2018

(65) Prior Publication Data
US 2020/0332441 A1    Oct. 22, 2020

Related U.S. Application Data

(60) Provisional application No. 62/500,029, filed on May 2, 2017.

(51) Int. Cl.
*C40B 50/06* (2006.01)
*C12P 19/34* (2006.01)
*C12P 21/02* (2006.01)

(52) U.S. Cl.
CPC .............. *C40B 50/06* (2013.01); *C12P 19/34* (2013.01); *C12P 21/02* (2013.01)

(58) Field of Classification Search
CPC .................... C12P 19/34; C40B 50/06
See application file for complete search history.

(56) References Cited

U.S. PATENT DOCUMENTS

| | | | |
|---|---|---|---|
| 5,573,905 A | 11/1996 | Lernerer et al. |
| 5,723,598 A | 3/1998 | Lernerer et al. |
| 5,759,779 A | 6/1998 | Dehlinger |
| 6,060,596 A | 5/2000 | Lerner et al. |
| 6,440,723 B1 | 8/2002 | Dale |
| 7,070,928 B2 | 7/2006 | Liu et al. |
| 7,223,545 B2 | 5/2007 | Liu et al. |
| 7,413,854 B2 | 8/2008 | Pedersen et al. |
| 7,442,160 B2 | 10/2008 | Liu et al. |
| 7,479,472 B1 | 1/2009 | Harbury et al. |
| 7,491,494 B2 | 2/2009 | Liu et al. |
| 7,557,068 B2 | 7/2009 | Liu et al. |
| 7,622,279 B2 | 11/2009 | Ju |
| 7,704,925 B2 | 4/2010 | Gouliaev et al. |
| 7,727,713 B2 | 6/2010 | Pedersen et al. |
| 7,771,935 B2 | 8/2010 | Liu et al. |
| 7,795,424 B2 | 9/2010 | Liu et al. |
| 7,883,869 B2 | 2/2011 | Liu et al. |
| 7,915,201 B2 | 3/2011 | Franch et al. |
| 7,928,211 B2 | 4/2011 | Hansen et al. |
| 7,935,658 B2 | 5/2011 | Morgan et al. |
| 7,972,992 B2 | 7/2011 | Morgan et al. |
| 7,972,994 B2 | 7/2011 | Morgan et al. |
| 7,989,395 B2 | 8/2011 | Morgan et al. |
| 7,998,904 B2 | 8/2011 | Liu et al. |
| 8,017,323 B2 | 9/2011 | Liu et al. |
| 8,071,739 B2 | 12/2011 | Milton et al. |
| 8,114,636 B2 | 2/2012 | Agnew et al. |
| 8,168,381 B2 | 5/2012 | Rasmussen |
| 8,183,178 B2 | 5/2012 | Liu et al. |
| 8,193,335 B2 | 6/2012 | Carell et al. |
| 8,202,823 B2 | 6/2012 | Hansen et al. |
| 8,206,901 B2 | 6/2012 | Freskgard et al. |
| 8,206,914 B2 | 6/2012 | Liu et al. |
| 8,298,792 B2 | 10/2012 | Ju et al. |
| 8,410,028 B2 | 4/2013 | Morgan et al. |

(Continued)

FOREIGN PATENT DOCUMENTS

| EP | 1670939 B1 | 11/2009 |
|---|---|---|
| EP | 2348124 A2 | 7/2011 |

(Continued)

OTHER PUBLICATIONS

Illustrated Glossary, Illustrated Glossary of Organic Chemistry, 2022, 1. Obtained on Nov. 22, 2022 at: https://www.chem.ucla.edu/~ harding/IGOC/Y/yield.html. (Year: 2022).*
Abdel-Magid et al., (1996). "Reductive amination of aldehydes and ketones with sodium triacetoxyborohydride," J. Org. Chem., 61:3849-3862.
Artuso et al., (2007). "Preparation of mono-, di-, and trisubstituted ureas by carbonylation of aliphatic amines with 5,5-dimethyl dithiocarbonate," Synthesis, 22:3497-3506.
Balcom et al., (1953). "Reductions with hydrazine hydrate catalyzed by Raney nickel," J. Am. Chem. Soc., 76:4334.
Barrow et al., (2007). "Design and synthesis of 2,3,5-substituted imidazolidin-4-one inhibitors of BACE-I," Chem. Med. Chem., 2:995-999.

(Continued)

*Primary Examiner* — Amy M Bunker
(74) *Attorney, Agent, or Firm* — MORRISON & FOERSTER LLP

(57) ABSTRACT

The present disclosure relates to multifunctional verification molecules, including molecules according to formula (I): G-L-(B)$_K$-Q-U, wherein G, L, B, K, Q, and U are defined herein. The present disclosure also relates to methods of preparing and using such multifunctional verification molecules to remove defective multifunctional molecules and to quantify synthetic yield.

3 Claims, 7 Drawing Sheets
Specification includes a Sequence Listing.

(56) References Cited

U.S. PATENT DOCUMENTS

| | | | |
|---|---|---|---|
| 8,541,570 B2 | 9/2013 | Gee et al. | |
| 8,552,173 B2 | 10/2013 | Skrzypczynski et al. | |
| 8,642,514 B2 | 2/2014 | Neri et al. | |
| 8,673,824 B2 | 3/2014 | Neri et al. | |
| 8,691,729 B2 | 4/2014 | Liu et al. | |
| 8,808,984 B2 | 8/2014 | Pedersen et al. | |
| 8,846,883 B2 | 9/2014 | Brown et al. | |
| 8,932,992 B2 | 1/2015 | Pedersen et al. | |
| 8,951,728 B2 | 2/2015 | Rasmussen | |
| 8,951,782 B2 | 2/2015 | Rasmussen | |
| 9,006,150 B2 | 4/2015 | Hansen et al. | |
| 9,096,951 B2 | 8/2015 | Freskgard et al. | |
| 9,109,248 B2 | 8/2015 | Freskgard et al. | |
| 9,121,110 B2 | 9/2015 | Gouliaev et al. | |
| 9,175,340 B2 | 11/2015 | Liu et al. | |
| 9,284,600 B2 | 3/2016 | Freskgard et al. | |
| 10,011,868 B2 | 7/2018 | Liu et al. | |
| 10,036,013 B2 | 7/2018 | Kim | |
| 10,053,725 B2 | 8/2018 | Liu et al. | |
| 10,240,147 B2 | 3/2019 | Decurtins et al. | |
| 10,513,700 B2 | 12/2019 | Hansen et al. | |
| 10,669,538 B2 | 6/2020 | Pederson et al. | |
| 11,186,836 B2 | 11/2021 | Watts | |
| 2005/0032081 A1 | 2/2005 | Ju et al. | |
| 2005/0247001 A1 | 11/2005 | Carell et al. | |
| 2006/0121470 A1 | 6/2006 | Pedersen | |
| 2006/0269920 A1 | 11/2006 | Freskgard et al. | |
| 2007/0026397 A1 | 2/2007 | Freskgard et al. | |
| 2007/0213519 A1 | 9/2007 | Gouliaev et al. | |
| 2008/0305957 A1 | 12/2008 | Thisted et al. | |
| 2009/0011957 A1 | 1/2009 | Gouliaev et al. | |
| 2009/0143232 A1 | 6/2009 | Pedersen et al. | |
| 2009/0239211 A1 | 9/2009 | Freskgard et al. | |
| 2009/0240030 A1 | 9/2009 | Ju et al. | |
| 2009/0264300 A1 | 10/2009 | Franch et al. | |
| 2010/0261181 A1 | 10/2010 | Agnew et al. | |
| 2011/0020799 A1 | 1/2011 | Ogi et al. | |
| 2012/0053091 A1 | 3/2012 | Wagner | |
| 2012/0071329 A1 | 3/2012 | Morgan et al. | |
| 2012/0142060 A1* | 6/2012 | Makarov ............... | C12P 19/34 435/91.2 |
| 2012/0245040 A1* | 9/2012 | Morgan ............... | C07H 21/00 506/4 |
| 2012/0252010 A1 | 10/2012 | Balasubramanian et al. | |
| 2013/0005581 A1 | 1/2013 | Hansen et al. | |
| 2013/0040823 A1 | 2/2013 | Freskgard et al. | |
| 2013/0046083 A1 | 2/2013 | Brown et al. | |
| 2013/0231473 A1 | 9/2013 | Brown et al. | |
| 2013/0237459 A1 | 9/2013 | Rasmussen | |
| 2013/0280700 A1 | 10/2013 | Ju et al. | |
| 2013/0281324 A1 | 10/2013 | Gouliaev et al. | |
| 2014/0235509 A1 | 8/2014 | Rasmussen | |
| 2014/0295414 A1 | 10/2014 | Salic et al. | |
| 2014/0315762 A1* | 10/2014 | Keefe ............... | C12N 15/1065 506/26 |
| 2014/0336079 A1 | 11/2014 | Agnew et al. | |
| 2015/0050697 A1 | 2/2015 | Kim | |
| 2015/0051088 A1 | 2/2015 | Kim | |
| 2015/0051116 A1 | 2/2015 | Kim | |
| 2015/0126381 A1 | 5/2015 | Rasmussen | |
| 2015/0203841 A1 | 7/2015 | Rasmussen | |
| 2015/0211002 A1 | 7/2015 | Keefe et al. | |
| 2015/0232957 A1 | 8/2015 | Fournier-Wirth et al. | |
| 2015/0315569 A1 | 11/2015 | Weisinger et al. | |
| 2015/0321164 A1 | 11/2015 | Li et al. | |
| 2015/0344872 A1* | 12/2015 | Harbury ............ | C12N 15/1068 506/28 |
| 2016/0040158 A1 | 2/2016 | Wagner et al. | |
| 2016/0222054 A1 | 8/2016 | Brown et al. | |
| 2016/0314242 A1 | 10/2016 | Schnall-Levin et al. | |
| 2016/0369267 A1 | 12/2016 | Wagner | |
| 2017/0009225 A1 | 1/2017 | Franch et al. | |
| 2017/0198336 A1 | 7/2017 | Reddavide et al. | |
| 2018/0002688 A1 | 1/2018 | Keefe et al. | |
| 2018/0135043 A1 | 5/2018 | Wong et al. | |
| 2019/0112730 A1 | 4/2019 | He et al. | |
| 2019/0136227 A1 | 5/2019 | Freskgard et al. | |
| 2019/0169607 A1* | 6/2019 | Watts ............... | C40B 10/00 |
| 2020/0216836 A1 | 7/2020 | Franch et al. | |
| 2020/0263163 A1 | 8/2020 | Watts et al. | |
| 2022/0145362 A1 | 5/2022 | Watts et al. | |
| 2022/0154179 A1 | 5/2022 | Watts | |

FOREIGN PATENT DOCUMENTS

| | | |
|---|---|---|
| JP | 2007524662 A | 8/2007 |
| JP | 2012517812 A | 8/2012 |
| RU | 2223319 C1 | 2/2004 |
| WO | WO-2000023458 A1 | 4/2000 |
| WO | WO-2003078446 A2 | 9/2003 |
| WO | WO-2004110964 A2 | 12/2004 |
| WO | WO-2005003778 A2 | 1/2005 |
| WO | WO-2005058479 A2 | 6/2005 |
| WO | WO-2006047791 A2 | 5/2006 |
| WO | WO-2006079061 A2 | 7/2006 |
| WO | WO-2007062664 A3 | 6/2007 |
| WO | WO-2009077173 A2 | 6/2009 |
| WO | WO-2010094036 A1 | 8/2010 |
| WO | WO-2011027933 A1 | 3/2011 |
| WO | WO-2011127933 A1 | 10/2011 |
| WO | WO-2012004240 A1 | 1/2012 |
| WO | WO-2015021080 A2 | 2/2015 |
| WO | WO-2015135856 A1 | 9/2015 |
| WO | WO-2016025804 A1 | 2/2016 |
| WO | WO-2016165621 A1 | 10/2016 |
| WO | WO-2017062973 A2 | 4/2017 |
| WO | WO-2017189631 A2 | 11/2017 |
| WO | WO-2017218293 A1 | 12/2017 |
| WO | WO-2018118897 A1 | 6/2018 |
| WO | WO-2018166532 A1 | 9/2018 |
| WO | WO-2018204420 A1 | 11/2018 |
| WO | WO-2019060856 A1 | 3/2019 |

OTHER PUBLICATIONS

Beugelmans et al., (1995). "Palladium catalyzed reductive deprotection of Alloc: Transprotection and peptide bond formation," Tetrahedron Lett., 36:3129-3132.

Brenner et al., (1992). "Encoded combinatorial chemistry," Proc Natl Acad Sci USA, 89(12):5381-5383.

Buller et al., (2008). "Design and synthesis of a novel DNA-encoded chemical library using Diels-Alder cycloadditions," Biorganic & Medicinal Chemistry Letters, 18:5926-5931.

Carriero et al., (2003). "Template-Mediated Synthesis of Lariat RNA and DNA," Journal of Organic Chemistry, 68:8328-8338.

Chauleta et al., (2011). "Design, synthesis and biological evaluation of new thalidomide analogues as TNF-a and IL-6 production inhibitors," Bioorg. Med. Chem. Lett., 21:1019-1022.

Deprez-Poulain et al., (2007). "Convenient synthesis of 4H-1,2,4-triazole-3-thiols using di-2-pyridylthionocarbonate," Tetrahedron Lett., 48:8157-8162.

Elia, (2010). "Protein Biotinylation," Current Protocols in Protein Science, 3.6.1-3.6.21.

Fedorova et al., (1996). "Cyanogen Bromide-Induced Chemical Ligation: Mechanism and Optimization of the Reaction Conditions," Nucleosides and Nucleotides, 15:1137-1147.

Giaever et al., (2002). "Functional profiling of the *Saccharomyces cerevisiae* genome," Nature, 418:387-391.

Gryaznov et al., (1993). "Chemical ligation of oligonucleotides in the presence and absence of a template," J. Am. Chem. Soc., 115:3808-3809.

Gurevich et al., (1991). "Preparative in vitro mRNA synthesis using SP6 and T7 RNA polymerases," Analytical Biochemistry, 195:207-213.

Halpin et al., (2004). "DNA Display III. Solid Phase Organic Synthesis on Unprotected DNA," PLoS Biology, 2(7):1031-1038.

Hong et al., (2009). "Analysis and Optimization of Copper-Catalyzed Azide—Alkyne Cycloaddition for Bioconjugation," Angewandte Chem Int Ed Engl., 48:9879-9883, 13 pages.

(56) References Cited

OTHER PUBLICATIONS

International Preliminary Report on Patentability for International Patent Application No. PCT/US2017/036582 dated Dec. 18, 2018, 8 pages.
Kanan et al., (2004). "Reaction discovery enabled by DNA-templated synthesis and in vitro selection," Nature, 431:545-549.
Leriche et al., (2012). "Cleavable linkers in chemical biology," Bioorganic & medicinal chemistry, 20(2), 571-582.
Li et al., (2011). "Copper-free Sonogashira cross-coupling for functionalization of alkyne encoded proteins in aqueous medium and in bacterial cells," J. Am. Chem. Soc., 133:15316-15319, 10 pages.
Liang et al., (2005). "Cooper-free 15 sonogashira coupling reaction with PdCl2 in water under aerobic conditions," J. Org. Chem., 70:391-393.
Lubbad et al., (2002). "Micropreparative fractionation of DNA fragments on metathesis-based monoliths: influence of stoichiometry on separation," J Chromatogr A., 959(1-2):121-9.
Lubbad et al., (2011). "Ring-opening metathesis polymerization-derived monolithic anion exchangers for the fast separation of double-stranded DNA fragments," J Chromatogr A., 1218(17):2362-7.
Lubbad et al., (2011). "Ring-opening metathesis polymerization-derived monolithic strong anion exchangers for the separation of 5'-phosphorylated oligodeoxythymidylic acids fragments," J Chromatogr A., 1218(49):8897-902.
Mandal et al., (2014). "RIP3 induces apoptosis independent of pronecrotic kinase activity," Mol. Cell, 56:481-495.
Manocci et al., (2011). "20 years of DNA-encoded chemical libraries," Chem. Commun., 47:12747-12753.
Marziale et al., (2011). "An efficient protocol for copper-free 20 palladium-catalyzed Sonogashira crosscoupling in aqueous media at low temperatures," Tetrahedron Lett., 52:6355-6358.
Mukhopadhyay et al., (2008). "Dowex 50W: A highly efficient and recyclable green catalyst for the construction of the 2-substituted benzimidazole moiety in aqueous medium," Catal. Commun., 9:2392-2394.
Plieva et al., (2004). "Characterization of polyacrylamide based monolithic columns," J. Sep. Sci., 27:828-836.
Plieva et al., (2006). "Macroporous polyacrylamide monolithic gels with immobilized metal affinity ligands: the effect of porous structure and ligand coupling chemistry on protein binding," J. Mol. Recognit., 19:305-312.
Plieva et al., (2008). "Cryogel applications in microbiology," Trends in Microbiology, 16(11):543-551.
Pokrovskaya et al., (1994). "In Vitro Transcription: Preparative RNA Yields in Analytical Scale Reactions," Analytical Biochemistry, 220:420-423.
Potewar et al., (2008). "Catalyst-free efficient synthesis of 2-aminothiazoles in water at ambient temperature," Tetrahedron 64:5019-5022.
Roughley et al., (2011). "The medicinal chemist's toolbox: an analysis of reactions used in the pursuit of drug candidates," J. Med. Chem., 54:3451-3479.
Shabarova et al., (1991). "Chemical ligation of DNA: the first non-enzymatic assembly of a biologically active gene," Nucleic Acids Research, 19:4247-4251.
Wang et al., (2011). "Asymmetric synthesis of LFA-1 inhibitor BIRT2584 on metric ton scale," Org. Process Res. Dev., 15:1185-1191.
Witt et al., (2000). "Synthesis and reactions of some 2-vinyl-3H-quinazolin-4-ones," Tetrahedron, 56:7245-7253.
Xie et al., (1996). "Preparation of porous hydrophilic monoliths: Effect of the polymerization conditions on the porous properties of poly (acrylamide-co-N,N'-methylenebisacrylamide) monolithic rods," J. Polym. Sci. A Polym. Chem., 35:1013-1021.
Extended European Search Report and Written Opinion for European Patent Application No. 18857926.2 dated Jun. 2, 2021, 12 pages.
Bao et al., (2016). "Predicting Electrophoretic Mobility of Protein-Ligand Complexes for Ligands from DNA-Encoded Libraries of Small Molecules," Analytical Chemistry, 88(10):5498-5506.
De la Torre et al., (2021). "Reprogramming the Genetic Code," Genetics Reviews, 22:169-184.
Drabovich et al., (2009). "Selection of Smart Small-Molecule Ligands: The Proof of Principle," Analytical Chemistry, 81(1):490-494.
Hoernes et al., (2018). "Translation of Non-Standard Codon Nucleotides Reveals Minimal Requirements for Condon-Anti-Codon Interactions," Nature Communications, 1-12.
Kierzek et al., (2014). "Microarrays for Identifying Binding Sites and Probing Structures of RNAs," Nucleic Acids Research, 43(1):1-12.
Shabalina et al., (2013). "Sounds of Silence: Synonymous Nucleotides as a Key to Biological Regulation and Complexity," Nucleic Acids Research, 41(4):2073-2094.

\* cited by examiner

MOLECULES FOR VERIFYING OLIGONUCLEOTIDE DIRECTED COMBINATORIAL SYNTHESIS AND METHODS OF MAKING AND USING THE SAME

CROSS-REFERENCE TO RELATED APPLICATIONS

This application is a National Stage Application of International Patent Application PCT/US18/30536, filed May 1, 2018, which claims priority to U.S. Provisional Application No. 62/500,029, filed May 2, 2017, each of which is incorporated by reference in its entirety.

TECHNICAL FIELD

The present invention relates to multifunctional verification molecules, and methods of preparing and using such multifunctional verification molecules. The present invention further provides methods of synthesizing the multifunctional verification molecules and using them to purify or quantify multifunctional verification molecules or multifunctional molecules.

BACKGROUND

There are basically three ways that molecules with desired functions, like drugs for example, are discovered. They are discovered in nature, they are rationally designed, and they are found by trial and error. In many cases, the trial and error method arguably holds the most promise, but it can be stunningly inefficient. The key to making the trial and error method more efficient has been to create combinatorial libraries of molecules that can be synthesized in vast numbers and tested for possession of desired properties. The need to efficiently discover new molecules through trial and error gave rise to the field of combinatorial chemistry.

There are three major problems with synthesizing and testing combinatorial libraries. First, many of the methods for preparing probe molecules from combinatorial libraries are limited by the types and number of successive chemical subunits or building blocks that can be assembled. Second, many of the methods for assembling successive building blocks are limited by the reaction efficiency of each step. Third, it is understood that to preserve efficiency, vast numbers of probe molecules should be simultaneously tested for possession of desired properties. It is also understood that libraries with a sufficient diversity of molecular shapes may possess only a few copies of any given molecule. The low number of copies frustrates identification of probe molecules possessing the desired properties. Therefore, each probe molecule should be labeled with a unique identifier so that researchers can identify the desired probe molecules.

Researchers have developed DNA encoded probe molecules to solve some of these problems. Some researchers have used DNA oligonucleotides as templates to direct one or more steps of combinatorial synthesis. Others have used DNA oligonucleotides to record combinatorial synthesis and uniquely label the probe molecules, so that PCR (polymerase chain reaction) amplification can be used to identify molecular probes that remain bound to the target molecule. Still, other researchers have used DNA oligonucleotides to direct one or more steps of combinatorial synthesis and to label the probe molecule with a unique identifier.

Despite the success of many of these methods, some problems still remain. It is generally accepted in chemistry that no reaction has a 100% yield. There are usually unreacted molecules and/or side reactions that lower the yield to less than 100%. DNA-encoded combinatorial chemistry usually relies on a series of synthetic steps to accurately encode and/or record the synthesis of a probe molecule. The failure of any one reaction during the formation of an oligonucleotide probe molecule can prohibit further reactions from occurring, which may render the probe molecule defective and perhaps useless. Also, the failure of one reaction during synthesis would result in a probe molecule that is not accurately recorded or identified by the encoding portion of the oligonucleotide molecule. Therefore, the chance of a defect is increased with each synthetic step.

Worse, when synthesizing oligonucleotide probe molecules using a series of reactions, there is no easy or cost-effective method of determining if each reaction step was successful. This issue results in most researchers applying the synthetic steps necessary to form the oligonucleotide probe molecules and then hoping for the best, because it would cost too much time and money to analyze each molecule during synthesis or even at the end of synthesis. The end result is often a mixture of accurately formed probe molecules and defective probe molecules, which can provide false results. There is a need for a cost-effective method of verifying the accurate synthesis of oligonucleotide probe molecules during or after synthesis, and quantifying the accurate synthetic yield after one or more reaction steps. There is a need for a cost-effective method of eliminating or reducing inaccurately synthesized oligonucleotide encoded probe molecules.

SUMMARY

The present disclosure relates to multifunctional verification molecules. In certain embodiments, the multifunctional verification molecules include molecules of formula (I), $$G\text{-}L\text{-}(B)_K\text{-}Q\text{-}U \qquad (I)$$

wherein

G includes an oligonucleotide, the oligonucleotide comprising at least two coding regions, wherein the at least two coding regions are single stranded, and, optionally, G contains T, wherein T is an attachment oligonucleotide that is from 0 to about 120 bases from a 3' end of G, wherein T is at least partially single stranded;

L is a linker that operatively links G to $(B)_K$;

B is a positional building block and K represents an integer from 1 to about 20;

Q is a non-positional building block directly attached to B at position K; and

U is an oligonucleotide that is capable of hybridizing to T or U is a chromatography agent;

wherein each positional building block B at position K is identified by one of the coding regions.

In certain embodiments of the molecule of formula (I), G comprises a sequence represented by the formula $(C_N\text{---}(Z_N\text{---}C_{N+1})_A)$ or $(Z_N\text{---}(C_N\text{---}Z_{N+1})_A)$, wherein C is a coding region, Z is a non-coding region, N is an integer from 1 to 20, and A is an integer from 1 to 20; wherein each non-coding region contains from 0 to 50 nucleotides and is optionally double stranded. In certain embodiments of the molecule of formula (I), each coding region contains from 6 to 50 nucleotides. In certain embodiments of the molecule of formula (I), each coding region contains from 8 to 30 nucleotides. In certain embodiments of the molecule of formula (I), T contains from 4 to about 80 nucleotides.

In certain embodiments of the molecule of formula (I), U contains from about 4 to about 80 nucleotides and U is hybridized to T to form a loop structure. In certain embodiments of the molecule of formula (I), the chromatography agent is selected from the group consisting of biotin, FLAG tag, polyhistidine, oligonucleotides captured by immobilized complementary oligonucleotides, and glutathione.

The present disclosure relates to a method of forming multifunctional verification molecules, including a molecule of formula (I). In certain embodiments, the method of forming a molecule of formula (I), includes
reacting a molecule of formula (II),

  (II)

with a molecule of formula (III),

  (III)

to form a molecule of formula (I),

  (I)

wherein
G includes an oligonucleotide, the oligonucleotide comprising at least two coding regions, wherein the at least two coding regions are single stranded, and, optionally, G contains T, wherein T is an attachment oligonucleotide that is from 0 to about 120 bases from a 3' end of G, wherein T is at least partially single stranded;
L is a linker that operatively links G to $(B)_K$;
B is a positional building block and K represents an integer from 1 to about 20;
Q is a non-positional building block directly attached to B at position K; and
U is an oligonucleotide that is capable of hybridizing to T or is an affinity chromatography agent;
wherein each positional building block B at position K is identified by one of the coding regions.

In certain embodiments of the method of forming a molecule of formula (I), G comprises a sequence represented by the formula $(C_N-(Z_N-C_{N+1})_A)$ or $(Z_N-(C_N-Z_{N+1})_A)$, wherein C is a coding region, Z is a non-coding region, N is an integer from 1 to 20, and A is an integer from 1 to 20; wherein each non-coding region contains from 0 to 50 nucleotides and is optionally double stranded. In certain embodiments of the method, each coding region contains from 6 to 50 nucleotides. In certain embodiments of the method, each coding region contains from 8 to 40 nucleotides. In certain embodiments of the method, T contains from 4 to about 80 nucleotides. In certain embodiments of the method, U contains from about 4 to about 80 nucleotides and U is hybridized to T to form a loop structure.

A method for forming multifunctional molecules is disclosed. In certain embodiments, the method for forming multifunctional molecules include methods of forming molecules of formula (II). In certain embodiments, the method of forming a molecule of formula (II), includes
providing at least one hybridization array, the at least one hybridization array comprising at least one single stranded anti-codon oligomer immobilized on the at least one hybridization array, wherein the at least one single stranded anti-codon oligomer immobilized on the at least one hybridization array is capable of hybridizing to a coding region of a molecule of formula (IV):

  (IV)

wherein
G includes an oligonucleotide, the oligonucleotide comprising at least two coding regions, wherein the at least two coding regions are single stranded, and, optionally, G contains T, wherein T is an attachment oligonucleotide that is from 0 to about 120 bases from a 3' end of G, wherein T is at least partially single stranded;
L is a linker that operatively links G to $(B)_{(K-1)}$; and
B is a positional building block and K represents an integer from 1 to about 20;
wherein each positional building block B at position K is identified by one of the coding regions;
sorting the pool of molecules of formula (IV) into sub-pools by hybridizing a coding region of the sub-pool of molecules of formula (IV) to the at least one single stranded anti-codon oligomer immobilized on the at least one hybridization array;
a step of optionally releasing the sub-pool of molecules of formula (IV) from the at least one hybridization array into separate containers;
providing at least one building block B; and reacting the at least one building block B with the molecule of formula (IV) to form a sub-pool of molecules of formula (II):

  (II)

wherein
G includes an oligonucleotide, the oligonucleotide comprising at least two coding regions, wherein the at least two coding regions are single stranded, and, optionally, G contains T, wherein T is an attachment oligonucleotide that is from 0 to about 120 bases from a 3' end of G, wherein T is at least partially single stranded;
L is a linker that operatively links G to $(B)_{(K-1)}$; and
B is a positional building block and K represents an integer from 1 to about 20;
wherein each positional building block B at position K is identified by one of the coding regions.

A method for purifying molecules is disclosed. In certain embodiments, the method of purifying molecules includes providing a pool of molecules containing at least one molecule of formula (I),

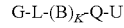

wherein
G includes an oligonucleotide, the oligonucleotide comprising at least two coding regions, wherein the at least two coding regions are single stranded, and, optionally, G contains T, wherein T is an attachment oligonucleotide that is from 0 to about 120 bases from a 3' end of G, wherein T is at least partially single stranded;
L is a linker that operatively links G to $(B)_K$;
B is a positional building block and K represents an integer from 1 to about 20;
Q is a non-positional building block directly attached to B at position K; and
U is an oligonucleotide that is capable of hybridizing to T or U is a chromatography agent;
wherein each positional building block B at position K is identified by one of the coding regions;
provided that U is an oligonucleotide, removing contaminants by annealing the oligonucleotide U to T to form a loop structure, performing polymerase chain reaction (PCR) to form a double stranded pool of molecules of formula (I), wherein G is double stranded, and adding a selection agent to the double stranded pool of molecules of formula (I), or
provided that U is a chromatography agent, removing contaminants from the molecules of formula (I) by performing at least one of affinity, immobilized metal ion, metal chelation, size exclusion, normal, and reverse phase chromatography.

In certain embodiments, the method for purifying molecules includes a step of, after removing contaminates, amplifying at least one oligonucleotide G from the molecules of formula (I) to form copies of G. In certain embodiments, the method for purifying molecules includes a step of sequencing at least one of the pool of pre-reaction copies of G and the pool of post-reaction copies of G.

A method for analyzing a synthetic yield is disclosed. The method of analyzing synthetic yield includes, providing a pool of molecules of formula (IV);

$$G\text{-}L\text{-}(B)_{(K\text{-}1)} \tag{IV}$$

amplifying G by polymerase chain reaction to form a pool of pre-reaction copies of G, reacting at least one molecule of formula (IV) to form molecules of formula (I)

according to methods disclosed herein, $$G\text{-}L\text{-}(B)_K\text{-}Q\text{-}U,$$

wherein

G includes an oligonucleotide, the oligonucleotide comprising at least two coding regions, wherein the at least two coding regions are single stranded, and, optionally, G contains T, wherein T is an attachment oligonucleotide that is from 0 to about 120 bases from a 3' end of G, wherein T is at least partially single stranded;

L is a linker that operatively links T to $(B)_K$ or $(B)_{(K-1)}$;

B is a positional building block and K represents an integer from 1 to about 20;

Q is a non-positional building block directly attached to B at position K; U is an oligonucleotide that is capable of hybridizing to T; and wherein each positional building block B at position K is identified by one of the coding regions;

provided that U is an oligonucleotide, removing contaminants by annealing the oligonucleotide U to T to form a loop structure, performing polymerase chain reaction (PCR) to form a double stranded pool of molecules of formula (I), wherein G is double stranded, and adding a selection agent to the double stranded pool of molecules of formula (I), or provided that U is a chromatography agent, removing contaminants from the molecules of formula (I) by performing at least one of affinity, immobilized metal ion, metal chelation, size exclusion, normal, or reverse phase chromatography; and amplifying at least one oligonucleotide G to form a pool of post-reaction copies of G.

In certain embodiments, the method of analyzing synthetic yield includes sequencing the pool of pre-reaction copies of G to provide pre-reaction sequencing data, sequencing the pool of post-reaction copies of G to provide post-reaction sequencing data, and comparing the pre-reaction sequencing data to the post-reaction sequencing data.

A method of analyzing synthetic yield is disclosed. In certain embodiments, the method of analyzing synthetic yield includes, reacting a molecule of formula (II), $$G\text{-}L\text{-}(B)_K$$

with a molecule of formula (III), $$Q\text{-}U$$

to form a molecule of formula (I), $$G\text{-}L\text{-}(B)_K\text{-}Q\text{-}U,$$

wherein

G includes an oligonucleotide, the oligonucleotide comprising at least two coding regions, wherein the at least two coding regions are single stranded, and, optionally, G contains T, wherein T is an attachment oligonucleotide that is from 0 to about 120 bases from a 3' end of G, wherein T is at least partially single stranded;

L is a linker that operatively links G to $(B)_K$;

B is a positional building block and K represents an integer from 1 to about 20;

Q is a non-positional building block directly attached to B at position K; and

U is an oligonucleotide that is capable of hybridizing to T or U is a chromatography agent;

wherein each positional building block B at position K is identified by one of the coding regions in G;

purifying molecules for formula (I) from unreacted molecules of formula (II) by a method comprising:

provided that U is an oligonucleotide, annealing the oligonucleotide U to T to form a loop structure; performing polymerase chain reaction (PCR) to form a double stranded pool of molecules of formula (I), wherein G is double stranded; and adding a selection agent to the double stranded pool of molecules of formula (I); or provided that U is a chromatography agent, performing at least one of affinity, size exclusion, normal, or reverse phase chromatography configured to select for the chromatography agent; and amplifying at least one oligonucleotide G to form a pool of post-reaction copies of G.

BRIEF DESCRIPTION OF THE DRAWINGS

The foregoing summary, as well as the following detailed description of the embodiments, will be better understood when read in conjunction with the attached drawings. For the purpose of illustration, there are shown in the drawings some embodiments, which may be preferable. It should be understood that the embodiments depicted are not limited to the precise details shown.

DETAILED DESCRIPTION

Figure 1:
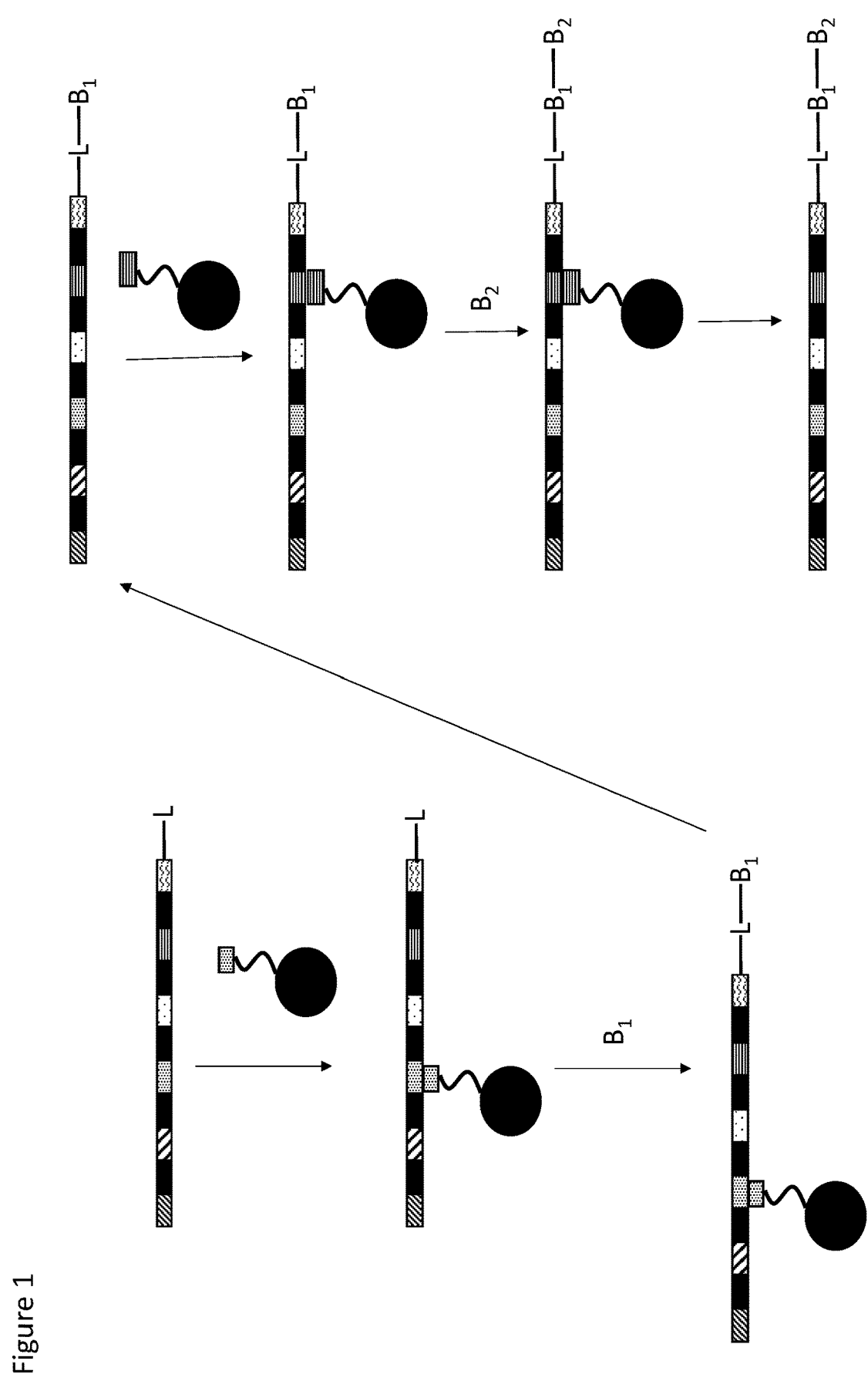
FIG. 1 is an illustration of an embodiment of a method of preparing a multifunctional molecule.

Unless otherwise noted, all measurements are in standard metric units.

Unless otherwise noted, all instances of the words "a," "an," or "the" can refer to one or more than one of the word that they modify.

Unless otherwise noted, the phrase "at least one of" means one or more than one of an object. For example, "at least one of $H_1$ and $H_2$" means $H_1$, $H_2$, or both.

Unless otherwise noted, the term "about" refers to ±10% of the non-percentage number that is described, and rounded to the nearest whole integer. For example, about 100 mm, would include 90 to 110 mm. Unless otherwise noted, the term "about" refers to ±5% of a percentage number. For example, about 20% would include 15 to 25%. When the term "about" is discussed in terms of a range, then the term refers to the appropriate amount less than the lower limit and more than the upper limit. For example, from about 100 to about 200 mm would include from 90 to 220 mm.

Unless otherwise noted, the term "hybridize," "hybridizing," and "hybridized" includes Watson-Crick base pairing, which includes guanine-cytosine and adenine-thymine (G-C and A-T) pairing for DNA and guanine-cytosine and adenine-uracil (G-C and A-U) pairing for RNA. This these terms are used in the context of the selective recognition of a strand of nucleotides for a complementary strand of nucleotides, called an anti-codon or anti-coding region.

The phrases "selectively hybridizing," "selective hybridization" and "selectively sorting" refer to a selectivity of from 5:1 to 100:1 or more of a complementary strand relative to a non-complementary strand.

The term "multifunctional molecule" refers to a molecule of the present disclosure that contains an oligonucleotide and at least one encoded portion.

The term "encoded portion" refers to one or more parts of the multifunctional molecule that only contain building blocks, such as positional building blocks $B_1$ and $B_2$. The term "encoded portion" does not include a linker, even though these structures may be added as part of the process of synthesizing the encoded portion.

The term "encoded molecule" refers to a molecule that would be or is formed if the encoded portion of the multifunctional molecule were removed or separated from the rest of the multifunctional molecule.

The term "probe molecule" refers to a molecule that is used to determine which encoded portion of a multifunctional molecule or encoded molecule is capable of binding a target molecule or selecting for desirable properties like target molecule selectivity or cell permeability.

The term "target molecule" refers to a molecule or structure. For example, structures include multi-macromolecular complexes, such as ribosomes, and liposomes.

The term "probe molecule" can include a multifunctional molecule.

The term "encoded probe molecule" is used interchangeably with the term multifunctional molecule.

In the present disclosure, the hyphen or dashes in a molecular formula indicate that the parts of the formula are directly connected to each other through a covalent bond or hybridization.

Unless otherwise noted, all ranges of nucleotides and integer values include all intermediate integer numbers as well as the endpoints. For example, the range of from 5 to 10 oligonucleotides would be understood to include 5, 6, 7, 8, 9, and 10 nucleotides.

In certain embodiments, the present disclosure relates to multifunctional molecules that contain at least one oligonucleotide portion and at least one encoded portion, wherein the oligonucleotide portion directed or encoded the synthesis of the at least one encoded portion using combinatorial chemistry. In certain embodiments, the oligonucleotide portion of the multifunctional molecule can identify the at least one encoded portion of the multifunctional molecule. In certain embodiments, a multifunctional molecule of the present disclosure contains at least one oligonucleotide or oligonucleotide portion that contains at least two coding regions, wherein the at least two coding regions correspond to and can be used to identify the sequence of building blocks in the encoded portion. In certain embodiments, the at least one oligonucleotide or oligonucleotide portion can be amplified by PCR to produce copies of the at least one oligonucleotide or oligonucleotide portion and the original or copies can be sequenced to determine the identity of the at least two coding regions of the multifunctional molecule. In certain embodiments, the identity of the at least two coding regions can be correlated to the series of combinatorial chemistry steps used to synthesize the encoded portion of the multifunctional molecule to which the PCR copy corresponds.

In certain embodiments, the present disclosure also relates to methods of forming multifunctional molecules, and to methods of exposing target molecules to the multifunctional molecules to identify which encoded portion, and therefore which encoded molecule, exhibits a desired property, including but not limited to the capability of binding a target molecule or molecules, of not binding other anti-target molecules, of being resistant to chemical changes made by enzymes, of being readily chemically changed by enzymes, of having degrees of water solubility, of being tissue permeable, and of being cell-permeable.

In certain embodiments, the present disclosure relates to a multifunctional verification molecule. In certain embodiments, a multifunctional verification molecule is or contains a multifunctional molecule. In certain embodiments, a multifunctional verification molecule contains at least one oligonucleotide portion, at least one encoded portion, and at least one verification portion. In certain embodiments, the verification portion of the multifunctional verification molecule would be directly attached to a positional building block of the encoded portion. In certain embodiments, the verification portion contains a non-positional building block Q that is directly connected or attached to a positional building block of the encoded portion of the multifunctional verification molecule. In certain embodiments, the verification portion contains a non-positional building block Q that is directly connected or attached to U. In certain embodiments, U is an oligonucleotide that is capable of hybridizing to G to form a hairpin on the 3' end of the encoding portion. In certain embodiments, U is a chromatography agent.

In certain embodiments, a multifunctional verification molecule includes a molecule of formula (I). A molecule according to formula (I), $$G\text{-}L\text{-}(B)_K\text{-}Q\text{-}U \qquad (I)$$

wherein

G includes an oligonucleotide, the oligonucleotide comprising at least two coding regions, wherein the at least two coding regions are single stranded, and G contains T, wherein T is an attachment oligonucleotide that is from 0 to about 120 bases from a 3' end of G, wherein T is at least partially single stranded;

L is a linker that operatively links G to $(B)_K$;

B is a positional building block and K represents an integer from 1 to about 20;

Q is a non-positional building block directly attached to B at position K; and

U is an oligonucleotide that is capable of hybridizing to T;

wherein each positional building block B at position K is identified by one of the coding regions.

A molecule according to formula (I),

G-L-(B)$_K$-Q-U  (I)

wherein

G includes an oligonucleotide, the oligonucleotide comprising at least two coding regions, wherein the at least two coding regions are single stranded;

L is a linker that operatively links G to (B)$_K$;

B is a positional building block and K represents an integer from 1 to about 20;

Q is a non-positional building block directly attached to B at position K; and

U is a chromatography agent;

wherein each positional building block B at position K is identified by one of the coding regions.

In certain embodiments of the molecule of formula (I), G is an oligonucleotide that directed or selected for the synthesis of the encoded portion. In certain embodiments of the molecule of formula (I), (B)$_K$ represents an encoded portion. In certain embodiments of the molecule of formula (I), the molecule contains an oligonucleotide portion and at least one encoded portion. It is understood that many of the structural features of the oligonucleotide G are discussed herein in terms of their having directed or encoded the synthesis of the at least one encoded portion of the molecule of formula (I). It is understood that many of the structural features of the oligonucleotide G of the molecule of formula (I) are discussed in terms of the ability of the oligonucleotide G, or a PCR copy thereof, to identify the synthetic steps used to prepare the molecule of formula (I) and therefore the sequence and/or identity of building blocks and the chemical reactions used to form the encoded portions of the molecule for formula (I).

In certain embodiments of the molecule of formula (I), G includes or is an oligonucleotide. In certain embodiments of G, the oligonucleotide has a 3' and a 5' end. In certain embodiments of G, the oligonucleotide one or more hairpin structures attached to the 3' and/or 5' end of the oligonucleotide in G. In certain embodiments, the oligonucleotide contains at least two coding regions, wherein from about 1% to 100%, including from about 50% to 100%, including from about 90% to 100%, of the coding regions are single stranded. In certain embodiments, the oligonucleotide G contains at least one oligonucleotide T. In certain embodiments, T is an oligonucleotide located from 0 to about 120 bases from a 3' end of G.

In certain embodiments of the molecule of formula (I), when U is an oligonucleotide, T is optionally an oligonucleotide that is capable of selectively hybridizing to U within the same molecule to form a hairpin structure. In certain embodiments, T is an oligonucleotide located from 0 to about 120 bases from a 3' end of G, including from 0 to about 90 bases from a 3' end of G, including from 0 to about 50 bases from a 3' end of G. In certain embodiments, if T is located more than about 120 bases from the 3' end of G, then the ability to hybridize T to U within the same molecule would be reduced or prevented. In certain embodiments, T contains from 4 to about 80 nucleotides, including from about 8 to about 60 nucleotides, including from about 12 to about 40 nucleotides. In certain embodiments, if T contains less than about 4 nucleotides, then the ability to hybridize T to U within the same molecule would be reduced, prevented, and/or the selectivity of the hybridization would be impermissibly lowered. In certain embodiments, T is from 25% to 100% single stranded, including from about 50% to about 95% single stranded, including from about 50% to about 75% single stranded. In certain embodiments, if T is less than 25% single stranded, then the ability of T to hybridize to U within the same molecule would be reduced or prevented. In certain embodiments, when U is a chromatography agent, then T may or may not be present in G. In certain embodiments, provided that U is a chromatography agent, then G does not contain T.

In certain embodiments of the molecule of formula (I), the oligonucleotide G contains at least two coding regions, including from 2 to about 21 coding regions, including from 3 to 10 coding regions, including from 3 to 5 coding regions. In certain embodiments, if the number of coding regions falls below 2, then the number of possible encoded portions that can be synthesized becomes too small to be practical. In certain embodiments, if the number of coding regions exceeds 21, then synthetic inefficiencies interfere with accurate synthesis.

In certain embodiments of the molecule of formula (I), the at least two coding regions contain from about 6 to about 50 nucleotides, including from about 12 to about 40 nucleotides, including from about 8 to about 30 nucleotides. In certain embodiments, if the coding region contains less than about 6 nucleotides then the coding region cannot accurately direct synthesis of the encoded portion. In certain embodiments, if the coding region contains more than about 50 nucleotides then the coding region could become cross reactive. Such cross reactivity would interfere with the ability of the coding regions to accurately direct and identify the synthesis steps used to synthesize the encoded portion of a molecule of formula (I).

In certain embodiments of the molecule of formula (I), a purpose of the oligonucleotide G is to direct the synthesis of at least one encoded portion of the molecule of formula (I) by selectively hybridizing to a complementary anti-coding strand. In certain embodiments, the coding regions are single stranded to facilitate hybridization with a complementary strand. In certain embodiments, from 70% to 100%, including from 80% to 99%, including from 80 to 95%, of the coding regions are single stranded. It is understood that a complementary strand for a coding region, if present, could be added after steps of encoding the encoded portion of the molecule of formula (I) during synthesis.

In certain embodiments, the oligonucleotide can contain natural and unnatural nucleotides. Suitable nucleotides include the natural nucleotides of DNA (deoxyribonucleic acid), including adenine (A), guanine (G), cytosine (C), and thymine (T), and the natural nucleotides of RNA (ribonucleic acid), adenine (A), uracil (U), guanine (G), and cytosine (C). Other suitable bases include natural bases, such as deoxyadenosine, deoxythymidine, deoxyguanosine, deoxycytidine, inosine, diamino purine; base analogs, such as 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, 4-((3-(2-(2-(3-aminopropoxy)ethoxy)ethoxy)propyl)amino)pyrimidin-2(1H)-one, 4-amino-5-(hepta-1,5-diyn-1-yl)pyrimidin-2(1H)-one, 6-methyl-3,7-dihydro-2H-pyrrolo[2,3-d]pyrimidin-2-one, 3H-benzo[b]pyrimido[4,5-e][1,4]oxazin-2(10H)-one, and 2-thiocytidine; modified nucleotides, such as 2'-substituted nucleotides, including 2'-O-methylated bases and 2'-fluoro bases; and modified sugars, such as 2'-fluororibose, ribose, 2'-deoxyribose, arabinose, and hexose; and/or modified phosphate groups, such as phosphorothioates and 5'-N-phosphoramidite linkages. It is understood that an oligonucleotide is a polymer of nucleotides. The terms "polymer" and "oligomer" are used herein interchangeably. In certain embodiments, the oligonucleotide does not have to contain contiguous bases. In certain embodiments, the oligonucleotide can be interspersed with linker moieties or non-nucleotide molecules.

In certain embodiments of the molecule of formula (I), the oligonucleotide G contains from about 60% to 100%, including from about 80% to 99%, including from about 80% to 95% DNA nucleotides. In certain embodiments, the oligonucleotide contains from about 60% to 100%, including from about 80% to 99%, including from about 80% to 95% RNA nucleotides.

In certain embodiments of the molecule of formula (I), the oligonucleotide G contains at least two coding regions, wherein the at least two of the coding regions overlap so as to be coextensive, provided that the overlapping coding regions only share from about 30% to 1% of the same nucleotides, including about 20% to 1%, including from about 10% to 2%. In certain embodiments of the molecule of formula (I), the oligonucleotide G contains at least two coding regions, wherein at least two of the coding regions are adjacent. In certain embodiments of the molecule of formula (I), the oligonucleotide G contains at least two coding regions, wherein the at least two coding regions are separated by regions of nucleotides that do not direct or record synthesis of an encoded portion of the molecule of formula (I).

The term "non-coding region," when present, refers to a region of the oligonucleotide that either cannot hybridize with a complementary strand of nucleotides to direct the synthesis of the encoded portion of the molecule of formula (I) or does not correspond to any anti-coding oligonucleotide used to sort the molecules of formula (I) during synthesis. In certain embodiments, non-coding regions are optional. In certain embodiments, the oligonucleotide contains from 1 to about 20 non-coding regions, including from 2 to about 9 non-coding regions, including from 2 to about 4 non-coding regions. In certain embodiments, the non-coding regions contain from about 4 to about 50 nucleotides, including from about 12 to about 40 nucleotides, and including from about 8 to about 30 nucleotides.

In certain embodiments of the molecule of formula (I), one purpose of the non-coding regions is to separate coding regions to avoid or reduce cross-hybridization, because cross-hybridization would interfere with accurate encoding of the encoded portion of the molecule of formula (I). In certain embodiments, one purpose of the non-coding regions is to add functionality, other than just hybridization or encoding, to the molecule of formula (I). In certain embodiments, one or more of the non-coding regions can be a region of the oligonucleotide that is modified with a label, such as a fluorescent label or a radioactive label. Such labels can facilitate the visualization or quantification of molecules of formula (I). In certain embodiments, one or more of the non-coding regions are modified with a functional group or tether which facilitates processing. In certain embodiments, one or more of the non-coding regions are double stranded, which reduces cross-hybridization. In certain embodiments, it is understood that non-coding regions are optional. In certain embodiments, suitable non-coding regions do not interfere with PCR amplification of the oligonucleotide of G.

In certain embodiments, one or more of the coding regions can be a region of the oligonucleotide G that is modified with a label, such as a fluorescent label or a radioactive label. Such labels can facilitate the visualization or quantification of molecules for formula (I). In certain embodiments, one or more of the coding regions are modified with a functional group or tether which facilitates processing.

In certain embodiments of the molecule of formula (I), G includes a sequence represented by the formula $(C_N—(Z_N—C_{N+1})_A)$ or $(Z_N—(C_N—Z_{N+1})_A)$, wherein C is a coding region, Z is a non-coding region, N is an integer from 1 to 20, and A is an integer from 1 to 20. In certain embodiments, from about 70% to 100%, including from about 80% to 99%, including from about 80 to 95%, of the non-coding regions contain from 0 to 50 nucleotides, including from 4 to 50 nucleotides. In certain embodiments, G includes from about 70% to 100%, including from about 80% to 99%, including from about 80% to 95%, of the non-coding regions are double stranded.

In certain embodiments of the molecule for formula (I), B represents a positional building block. The phrase "positional building block" as used in the present disclosure means one unit in a series of individual building block units bound together as subunits forming a larger molecule. In certain embodiments, $(B)_K$ each represents a series of individual building block units bound together to form a polymer chain having K number of units. For example, wherein K is 10, then $(B)_{10}$, refers to a chain of building block units: $B_1—B_2—B_3—B_4—B_5—B_6—B_7—B_8—B_9—B_{10}$. For example, where K is 2, then formula (I) can accurately be represented by the following formula:

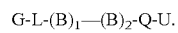

G-L-(B)$_1$—(B)$_2$-Q-U.

It is understood that K serves as a positional identifier for each individual unit of B. Therefore, $(B)_K$ can refer to building block B at position K or an oligomer that is $(B)_K$ units long, depending on the context.

In certain embodiments of the molecule of formula (I), Q represents a non-positional building block. The phrase "non-positional building block" as used in the present disclosure means one or more building block units that do not correspond and/or are not identified by a coding region of G.

The precise definition of the term "building block" in the present disclosure depends on its context. A "building block" is a chemical structural unit capable of being chemically linked to other chemical structural units. In certain embodiments, a building block has one, two, or more reactive chemical groups that allow the building block to undergo a chemical reaction that links the building block to other chemical structural units. It is understood that part or all of the reactive chemical group of a building block may be lost when the building block undergoes a reaction to form a chemical linkage. For example, a building block in solution may have two reactive chemical groups. In this example, the building block in solution can be reacted with the reactive chemical group of a building block that is part of a chain of building blocks to increase the length of a chain, or extend a branch from the chain. When a building block is referred to in the context of a solution or as a reactant, then the building block will be understood to contain at least one reactive chemical group, but may contain two or more reactive chemical groups. When a building block is referred to the in the context of a polymer, oligomer, or molecule larger than the building block by itself, then the building block will be understood to have the structure of the building block as a (monomeric) unit of a larger molecule, even though one or more of the chemical reactive groups will have been reacted.

The types of molecule or compound that can be used as a building block are not generally limited, so long as one building block is capable of reacting together with another building block to form a covalent bond. In certain embodiments, a building block has one chemical reactive group to serve as a terminal unit. In certain embodiments, a building block has 1, 2, 3, 4, 5, or 6 suitable reactive chemical groups. In certain embodiments, the positional building blocks of B each independently have 1, 2, 3, 4, 5, or 6 suitable reactive chemical groups. Suitable reactive chemical groups for building blocks include, a primary amine, a secondary amine, a carboxylic acid, a primary alcohol, an ester, a thiol, an isocyanate, a chloroformate, a sulfonyl chloride, a thionocarbonate, a heteroaryl halide, an aldehyde, a haloacetate, an aryl halide, an azide, a halide, a triflate, a diene, a dienophile, a boronic acid, an alkyne, and an alkene.

Any coupling chemistry can be used to connect building blocks, provided that the coupling chemistry is compatible with the presence of an oligonucleotide. Exemplary coupling chemistry includes, formation of amides by reaction of an amine, such as a DNA-linked amine, with an Fmoc-protected amino acid or other variously substituted carboxylic acids; formation of ureas by reaction of an amine, including a DNA-linked amine, with an isocyanate and another amine (ureation); formation of a carbamate by reaction of amine, including a DNA-linked amine, with a chloroformate (carbamoylation) and an alcohol; formation of a sulfonamide by reaction of an amine, including a DNA-linked amine, with a sulfonyl chloride; formation of a thiourea by reaction of an amine, including a DNA-linked amine, with thionocarbonate and another amine (thioureation); formation of an aniline by reaction of an amine, including a DNA-linked amine, with a heteroaryl halide (SNAr); formation of a secondary amine by reaction of an amine, including a DNA-linked amine, with an aldehyde followed by reduction (reductive amination); formation of a peptoid by acylation of an amine, including a DNA-linked amine, with chloroacetate followed by chloride displacement with another amine (an $SN_2$ reaction); formation of an alkyne containing compound by acylation of an amine, including a DNA-linked amine, with a carboxylic acid substituted with an aryl halide, followed by displacement of the halide by a substituted alkyne (a Sonogashira reaction); formation of a biaryl compound by acylation of an amine, including a DNA-linked amine, with a carboxylic acid substituted with an aryl halide, followed by displacement of the halide by a substituted boronic acid (a Suzuki reaction); formation of a substituted triazine by reaction of an amine, including a DNA-linked amine, with a cyanuric chloride followed by reaction with another amine, a phenol, or a thiol (cyanurylation, Aromatic Substitution); formation of secondary amines by acylation of an amine including a DNA-linked amine, with a carboxylic acid substituted with a suitable leaving group like a halide or triflate, followed by displacement of the leaving group with another amine ($SN_2/SN_1$ reaction); and formation of cyclic compounds by substituting an amine with a compound bearing an alkene or alkyne and reacting the product with an azide, or alkene (Diehls-Alder and Huisgen reactions). In certain embodiments of the reactions, the molecule reacting with the amine group, including a primary amine, a secondary amine, a carboxylic acid, a primary alcohol, an ester, a thiol, an isocyanate, a chloroformate, a sulfonyl chloride, a thionocarbonate, a heteroaryl halide, an aldehyde, a chloroacetate, an aryl halide, an alkene, halides, a boronic acid, an alkyne, and an alkene, has a molecular weight of from about 30 to about 330 Daltons.

In certain embodiments of the coupling reaction, a first positional building block might be added by substituting an amine, including a DNA-linked amine, using any of the chemistries above with molecules bearing secondary reactive groups like amines, thiols, halides, boronic acids, alkynes, or alkenes. Then the secondary reactive groups can be reacted with building blocks bearing appropriate reactive groups. Exemplary secondary reactive group coupling chemistries include, acylation of the amine, including a DNA-linked amine, with an Fmoc-amino acid followed by removal of the protecting group and reductive amination of the newly deprotected amine with an aldehyde and a borohydride; reductive amination of the amine, including a DNA-linked amine, with an aldehyde and a borohydride followed by reaction of the now-substituted amine with cyanuric chloride, followed by displacement of another chloride from triazine with a thiol, phenol, or another amine; acylation of the amine, including a DNA-linked amine, with a carboxylic acid substituted by a heteroaryl halide followed by an SNAr reaction with another amine or thiol to displace the halide and form an aniline or thioether; and acylation of the amine, including a DNA-linked amine, with a carboxylic acid substituted by a haloaromatic group followed by substitution of the halide by an alkyne in a Sonogashira reaction; or substitution of the halide by an aryl group in a boronic ester-mediated Suzuki reaction.

In certain embodiments, the coupling chemistries are based on suitable bond-forming reactions known in the art. See, for example, March, Advanced Organic Chemistry, fourth edition, New York: John Wiley and Sons (1992), Chapters 10 to 16; Carey and Sundberg, Advanced Organic Chemistry, Part B, Plenum (1990), Chapters 1-11; and Coltman et al., Principles and Applications of Organotransition Metal Chemistry, University Science Books, Mill Valley, Calif. (1987), Chapters 13 to 20; each of which is incorporated herein by reference in its entirety.

In certain embodiments, a building block can include one or more functional groups in addition to the reactive group or groups employed to attach a building block. One or more of these additional functional groups can be protected to prevent undesired reactions of these functional groups. Suitable protecting groups are known in the art for a variety of functional groups (Greene and Wuts, Protective Groups in Organic Synthesis, second edition, New York: John Wiley and Sons (1991), incorporated herein by reference in its entirety). Particularly useful protecting groups include t-butyl esters and ethers, acetals, trityl ethers and amines, acetyl esters, trimethylsilyl ethers, trichloroethyl ethers and esters and carbamates.

The type of building block is not generally limited, so long as the building block is compatible with one more reactive groups capable of forming a covalent bond with other building blocks. Suitable building blocks include but are not limited to, a peptide, a saccharide, a glycolipid, a lipid, a proteoglycan, a glycopeptide, a sulfonamide, a nucleoprotein, a urea, a carbamate, a vinylogous polypeptide, an amide, a vinylogous sulfonamide peptide, an ester, a saccharide, a carbonate, a peptidylphosphonate, an azatides, a peptoid (oligo N-substituted glycine), an ether, an ethoxyformacetal oligomer, thioether, an ethylene, an ethylene glycol, disulfide, an arylene sulfide, a nucleotide, a morpholino, an imine, a pyrrolinone, an ethyleneimine, an acetate, a styrene, an acetylene, a vinyl, a phospholipid, a siloxane, an isocyanide, a isocyanate, and a methacrylate. In certain embodiments, the $(B_1)_M$ or $(B_2)_K$ of formula (I) each independently represents a polymer of these building blocks having M or K units, respectively, including a polypeptide, a polysaccharide, a polyglycolipid, a polylipid, a polyproteoglycan, a polyglycopeptide, a polysulfonamide, a polynucleoprotein, a polyurea, a polycarbamate, a polyvinylogous polypeptide, a polyamide, a poly vinylogous sulfonamide peptide, a polyester, a polysaccharide, a polycarbonate, a polypeptidylphosphonate, a polyazatides, a polypeptoid (oligo N-substituted glycine), a polyethers, a polythoxyformacetal oligomer, a polythioether, a polyethylene, a polyethylene glycol, a polydisulfide, a polyarylene sulfide, a polynucleotide, a polymorpholino, a polyimine, a polypyrrolinone, a polyethyleneimine, a polyacetates, a polystyrene, a polyacetylene, a polyvinyl, a polyphospholipids, a polysiloxane, a polyisocyanide, a polyisocyanate, and a polymethacrylate. In certain embodiments of the molecule for formula (I), from about 50 to about 100, including from about 60 to about 95, and including from about 70 to about 90% of the building blocks have a molecular weight of from about 30 to about 500 Daltons, including from about 40 to about 350 Daltons, including from about 50 to about 200 Daltons.

It is understood that building blocks having two reactive groups would form a linear oligomeric or polymeric structure, or a linear non-polymeric molecule, containing each building block as a unit. It is also understood that building blocks having three or more reactive groups could form molecules with branches at each building block having three or more reactive groups.

In certain embodiments of the molecule of formula (I), L represents a linker. The term "linker molecule" refers to a molecule having two or more reactive groups that is capable of reacting to form a linker. The term "linker" refers to a portion of a molecule that operatively links or covalently bonds G to a positional building block. The term "operatively linked" means that two or more chemical structures are attached or covalently bonded together in such a way as to remain attached throughout PCR amplification.

In certain embodiments of the molecule for formula (I), L is a linker that operatively links L to $B_1$. In certain embodiments, L is a bifunctional molecule linking G to $(B)_K$ by reacting one of the reactive functional groups of L to a reactive group of $B_1$ or B at position K and the other reactive functional group of L to a reactive functional group of G. In certain embodiments of the molecule for formula (I), L is a linker formed from reacting the chemical reactive groups of G and $B_1$ or $(B)_K$ with commercially available linker molecules including, PEG (e.g., azido-PEG-NHS, or azido-PEG-amine, or di-azido-PEG), or an alkane acid chain moiety (e.g., 5-azidopentanoic acid, (S)-2-(azidomethyl)-1-Boc-pyrrolidine, 4-azidoaniline, or 4-azido-butan-1-oic acid N-hydroxysuccinimide ester); thiol-reactive linkers, such as those being PEG (e.g., SM(PEG)n NHS-PEG-maleimide), alkane chains (e.g., 3-(pyridin-2-yldisulfanyl)-propionic acid-Osu or sulfosuccinimidyl 6-(3'-[2-pyridyldithio]-propionamido)hexanoate)); and amidites for oligonucleotide synthesis, such as amino modifiers (e.g., 6-(trifluoroacetylamino)-hexyl-(2-cyanoethyl)-(N,N-diisopropyl)-phosphoramidite), thiol modifiers (e.g., 5-trityl-6-mercaptohexyl-1-[(2-cyanoethyl)-(N,N-diisopropyl)]-phosphoramidite, or chemically co-reactive pair modifiers (e.g., 6-hexyn-1-yl-(2-cyanoethyl)-(N,N-diisopropyl)-phosphoramidite, 3-dimethoxytrityloxy-2-(3-(3-propargyloxypropanamido)propanamido)propyl-1-O-succinoyl, long chain alkylamino CPG, or 4-azido-butan-1-oic acid N-hydroxysuccinimide ester)); and compatible combinations thereof.

In certain embodiments of the molecule of formula (I), U is an oligonucleotide. In certain embodiments, U contains from 4 to about 80 nucleotides, including from about 8 to about 60 nucleotides, including from about 12 to about 40 nucleotides. In certain embodiments, when T is present in G, then U is capable of hybridizing to T to form a loop structure. In certain embodiments, U is hybridized to T to form a loop structure. In certain embodiments, where U is not linked to G, for example, when a reaction between Q and $B_{(K)}$ has not proceeded efficiently, un-linked U can be removed from a molecule of formula (I) prior to a PCR step. In certain embodiments, one benefit of forming a loop structure by hybridizing U to T includes an ability to selectively perform PCR on those multifunctional verification molecules having a loop structure. In certain embodiments, the formation of a loop structure at the 3' end of the molecule of formula (I) selectively increases the chance of the molecule for formula (I) undergoing PCR by a ratio of at least 2:1 relative to a multifunctional molecule not having a loop structure at the 3' end of the multifunctional molecule, including a ratio of at least 5:1, and including a ratio of at least 20:1, and including a ration of at least 100:1.

In certain embodiments of the molecule of formula (I), U is a chromatography agent. In certain embodiments, the chromatography agent includes biotin, FLAG tag, polyhistidine, oligonucleotides captured by immobilized complementary oligonucleotides, and glutathione. In certain embodiments, FLAG tag is a polypeptide protein tag having the sequence motif DYKDDDDK (where D=aspartic acid, Y=tyrosine, and K=lysine. In certain embodiments, U can be a reactive functional group that forms a covalent bond to a reactive moiety on a solid support, for example, U can be an alkyne enabling purification on columns bearing immobilized azides, or vice versa; similarly, U could be an amine or thiol which can be immobilized on an electrophilic solid support like NHS agarose (U could also be a protected amine or thiol which after deprotection can be captured on an electrophilic support). In certain embodiments, when U is a chromatography agent, the chromatography agent can be used to selectively separate multifunctional verification molecules of formula (I) that include a chromatography agent from defective multifunctional molecules that do contain a chromatography agent.

The present disclosure relates to methods of synthesizing multifunctional molecules. As depicted in FIG. 1, in certain embodiments, a multifunctional molecule can be synthesized by a series of steps that separate oligonucleotides based on hybridizing a coding region of the oligonucleotide, wherein six coding regions are represented by six partially-shaded rectangles, with a complementary oligonucleotide (shown as a rectangle attached to a circle). Then, a linker group present on the oligonucleotides can be reacted with a building block $B_1$ to form a multifunctional molecule. Multifunctional molecules can be separated from the complementary oligonucleotide and the process can be repeated to form a multifunctional molecule having an encoded portion that contains more building block units. In certain embodiments, separation from the complementary oligonucleotide can be performed prior to a linker group present on the nucleotide being reacted with a building block $B_1$ to from a multifunctional molecule. In certain embodiments, a multifunctional molecule is represented by formula (II):

$$G\text{-}L\text{-}(B)_K \qquad (II)$$

wherein G, T, K, and B are as defined for formula (I) above.

Figure 2:
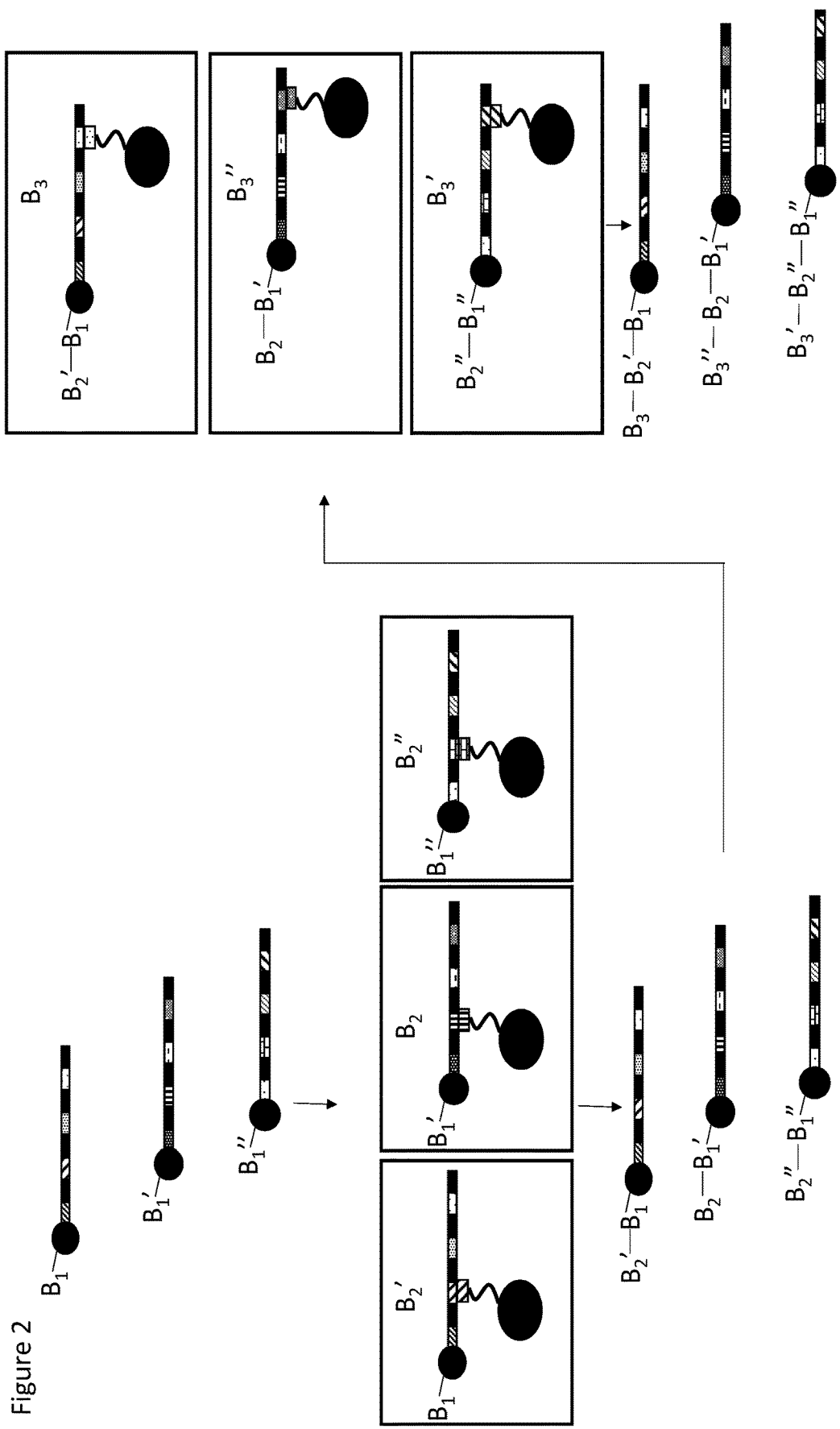
FIG. 2 is an illustration of an embodiment of a method of preparing a plurality of multifunctional molecules.

As depicted in FIG. 2, in certain embodiments of a method of synthesizing a multifunctional molecule, including a molecule of formula (II), the method uses a series of "sort and react" steps, where a mixture of multifunctional molecules containing different combinations of encoding regions are sorted into sub-pools by selective hybridization of one or more coding regions of the multifunctional molecule with an anti-coding oligomer immobilized on a hybridization array. In certain embodiments of the method, a benefit to sorting the multifunctional molecules into sub-pools is that this separation allows for each sub-pool to be reacted with a positional building block B, including $B_1$, $B_1'$, $B_1''$, $B_2$, $B_2'$, $B_2''$, $B_3$, $B_3'$, and $B_3''$, under separate reaction conditions before the sub-pools of multifunctional molecules are combined or mixed for further chemical processing. In certain embodiments of the method, the sort and react process can be repeated to add a series of positional building blocks to form an encoded portion. In certain embodiments of the method, a benefit of adding building blocks using a sort and react method is that the identity of each positional building block of the encoded portion of the molecule can be correlated to the coding region that is used to selectively separate or sort the multifunctional molecule prior to the addition of a building block. In certain embodiments, each coding region uniquely identifies a building block according to its position, because the identity of the coding region can be correlated to the identity of the reaction process used to add each building block, which would include the identity of the positional building block added. In certain embodiments, the method can synthesize a multifunctional molecule, including a molecule of formula (II), wherein at least one of each positional building block B at position K is identified by or corresponds to one of the coding regions. It is understood that the molecules of formulas (I) and (II) can include one or more coding regions that are identical between or among molecules in a pool, but it is also understood that the vast majority, if not all, of the molecules in the pool would have a different combination of coding regions. In certain embodiments of the method, a benefit of a pool of molecules having a different combination of coding region is that the different combinations can encode for multifunctional molecules having a multitude of different encoded portions.

The present disclosure relates to a method of synthesizing one or more multifunctional verification molecules, including a molecule of formula (I). In certain embodiments of a method of synthesizing a molecule of formula (I), the method includes reacting a molecule of formula (II),

G-L-(B)$_K$            (II)

with a molecule of formula (III),

Q-U to form a molecule of formula (I),

G-L-(B)$_K$-Q-U, wherein G, L, B, K, Q, U, and T are as defined for the molecule of formula (I). In certain embodiments, the method includes a step of providing a molecule for formula (II) and a molecule of formula (III). In certain embodiments, the method includes combining and/or reacting a molecule of formula (II) and a molecule for formula (III) to form a molecule of formula (I). In certain embodiments, each positional building block (B)$_K$ can be selected such that the exposed or available reactive group of the growing chain is different. In certain embodiments, the non-positional building block Q can be a building block with a reactive group that is highly selective for or only capable of reacting with a reactive group of one positional building block, including the terminal positional building block B at position K.

Figure 3:
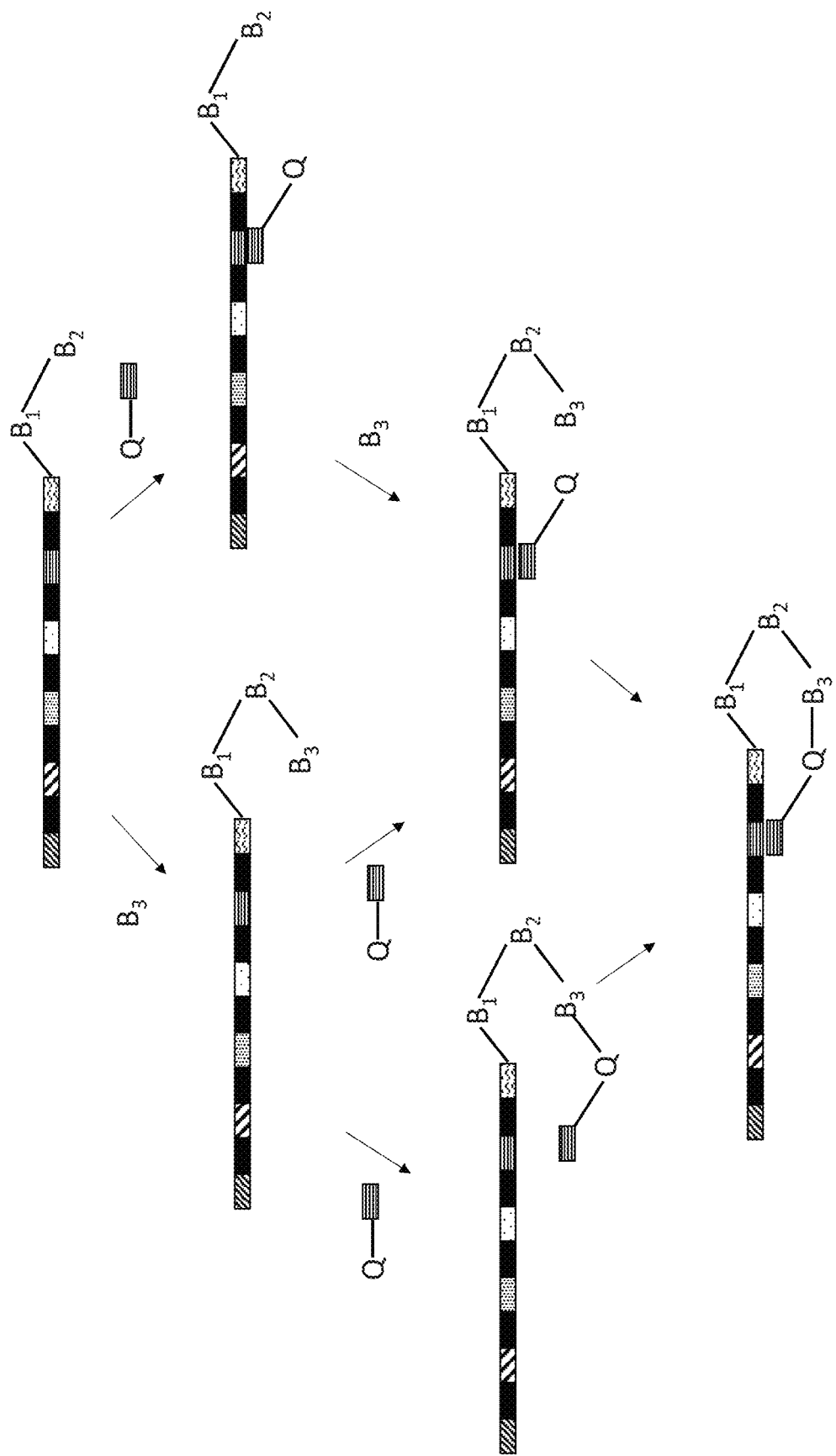
FIG. 3 is an illustration of multiple embodiments of methods for preparing an embodiment of a multifunctional verification molecule.

As depicted in FIG. 3, when U is an oligonucleotide and G contains T, then the verification portion Q-U can be added before, during, or after the addition of a positional building block (B)$_K$, such as, for example, $B_3$. In certain embodiments, the non-positional building block Q may be reacted with the positional building block (B)$_K$ before, during, or after U is hybridized to the oligonucleotide G to form a loop structure as depicted in FIG. 3.

In certain embodiments, a benefit to having a non-positional building block Q that is highly selective for or only capable of reacting with the exposed or available reactive group of one building block at a position (B)$_K$ can be the highly selective attachment of Q-U to those molecules of Formula (II) which contains that exact building block B at position K. In certain embodiments, Q can be configured to react with one building block B at position K to verify the presence of that exact building block. Since that exact building block is highly selective for reacting with Q, then the absence of that building block would indicate that the multifunctional molecule being formed at position (B)$_K$ is at least defective at the position (B)$_K$, and may be defective at a previously added positional building block. Due to the successive sort and react synthesis of the encoded portion, a defect in addition of any previously added positional building block will almost certainly lead to a defect in later synthesis. In certain embodiments, the successful synthesis of molecule (I) by reacting Q with a positional building block B at position K would indicate that the multifunctional verification molecule is accurately coded and therefore not defective. Conversely, in certain embodiments, a multifunctional molecule that where Q does not react with or bind the positional building block B at position K would indicate that the multifunctional building block is defective at position K and/or a previously added positional building block. In certain embodiments, Q is selective for reaction with a positional building block B at position K, including a ratio of at least 5:1, including a ratio of at least 10:1, including a ratio of at least 20:1, and including a ratio of at least 50:1, relative to any other positional building block in the encoded portion. If Q is less selective than a ratio of 5:1 for a reaction with a positional building block B at position K than another building block, then the cross-reactivity could interfere with the ability of the multifunctional molecule to the accuracy of the encoded portion.

Figure 4:
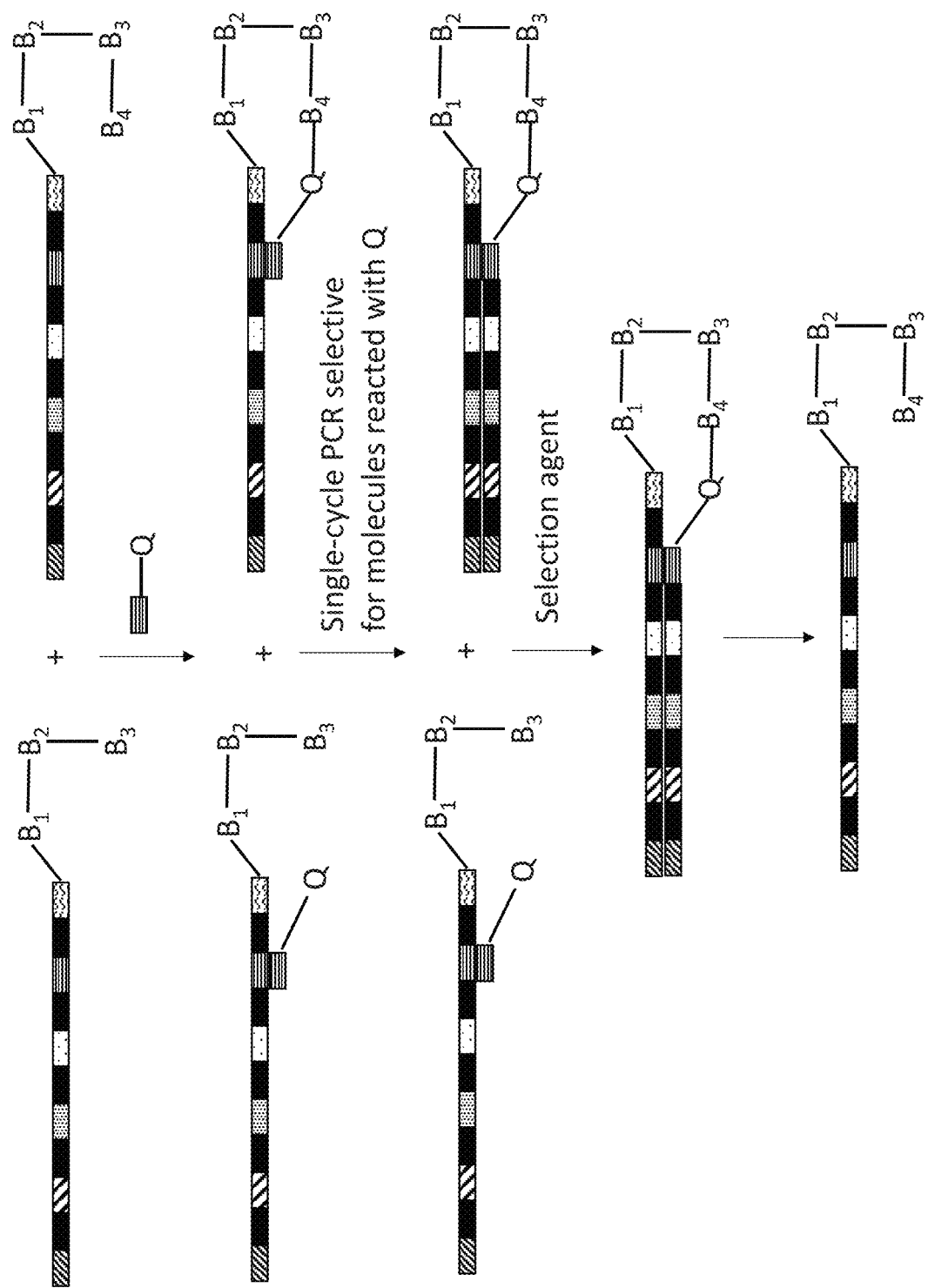
FIG. 4 is an illustration of an embodiment of a method of selectively performing PCR on a multifunctional verification molecule in a mixture with a defective multifunctional molecule, and then selectively eliminating the defective multifunctional molecule.

For example, as depicted in FIG. 4, in certain embodiments, when U is an oligonucleotide, G contains T, and Q reacts selectively with a positional building block $B_4$, then a mixture of multifunctional molecules that includes a multifunctional verification molecule containing $B_4$ and a defective multifunctional molecule not containing $B_4$ may be separated. In this example, the multifunctional verification molecule containing $B_4$ can form a loop structure, whereas the defective multifunctional molecule not containing $B_4$ cannot. As further depicted in FIG. 4, in certain embodiments, the formation of the loop structure in the multifunctional verification molecule can allow for PCR to selectively convert the multifunctional verification molecule into a double stranded multifunctional verification molecule while the defective multifunctional molecule remains single stranded. In certain embodiments, the defective multifunctional molecule can then be selectively reacted with a selection agent, such as Mung Bean Nuclease, RecJf, or Exonuclease VII to eliminate or reduce the amount of the defective multifunctional molecule. In certain embodiments, the multifunctional verification molecule can be converted back into the multifunctional molecule by removing the verification portion, Q-U, and optionally the double stranded portions added by PCR. In certain embodiments, the multifunctional verification molecule is not converted back, because the multifunctional verification molecule was converted for testing and quantification purposes. In certain embodiments, the multifunctional verification molecule is converted back into the multifunctional molecule for reasons that may include continuing synthesis of the encoded portion of the multifunctional molecule or using the multifunctional molecule as a probe molecule.

Figure 5:
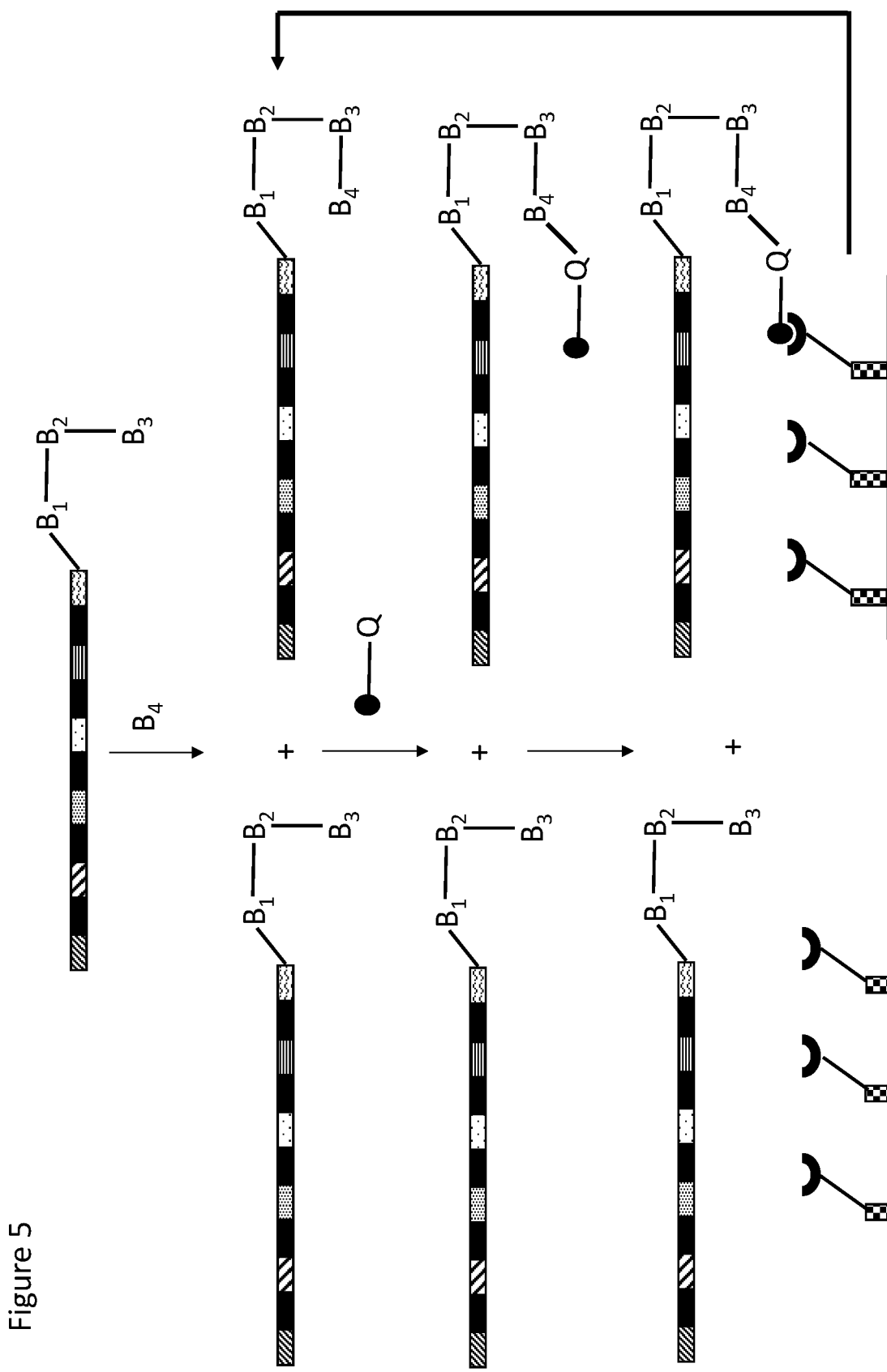
FIG. 5 is an illustration of an embodiment of a method of selectively separating a multifunctional verification molecule containing a chromatography agent from a mixture containing a defective multifunctional molecule by passing the mixture over a solid phase that selectively separates the multifunctional verification molecule.

In a different example, as depicted in FIG. 5, in certain embodiments, where U is a chromatography agent and Q reacts selectively with positional building block $B_4$, then a mixture of multifunctional molecules that includes a multifunctional verification molecule containing molecule containing $B_1$, $B_2$, $B_3$, and $B_4$ and a defective multifunctional molecule containing $B_1$, $B_2$, and $B_3$, but not containing $B_4$ can be separated. In certain exemplary embodiments, the verification portion of the molecule contains a chromatography agent. In certain embodiments, one benefit of forming a multifunctional verification molecule containing a chromatography agent is that the chromatography agent can allow for known chromatography methods to separate or reduce the amount of defective multifunctional molecules from the multifunctional verification molecules containing the chromatography agent. The choice of chromatography agent is not generally limited, so long as it allows for the removal of impurities, including defective multifunctional molecules, from multifunctional verification molecules. In certain embodiments, the chromatography agent can include, biotin, FLAG tag, polyhistidine, oligonucleotides captured by immobilized complementary oligonucleotides, and glutathione. The choice of chromatographic method is not generally limited so long as it allows for the removal of impurities, including defective multifunctional molecules, from multifunctional verification molecules. In certain embodiments, the chromatographic method includes affinity, immobilized metal ion, metal chelation, size exclusion, normal, or reverse phase chromatography.

In certain embodiments, the method includes providing at least one hybridization array. The step of providing a hybridization array is not generally limited, and includes manufacturing the hybridization array using techniques known in the art or commercially purchasing the hybridization array. In certain embodiments of the method, a hybridization array includes a substrate of at least two separate areas having immobilized anti-codon oligomers on their surface. In certain embodiments, each area of the hybridization array contains a different immobilized anti-codon oligomer, wherein the anti-codon oligomer is an oligonucleotide sequence that is capable of hybridizing with one or more coding regions of a molecule of formulas (I), (II), or (IV). In certain embodiments of the method, the hybridization array uses two or more chambers. In certain embodiments of the method, the chambers of the hybridization array contain particles, such as beads, that have immobilized anti-codon oligomers on the surface of the particles. In certain embodiments of the method, a benefit of immobilizing a molecule of formula (I), (II), or (IV) on the array, is that this step allows the molecules to be sorted or selectively separated into sub-pools of molecules on the basis of the particular oligonucleotide sequence of each coding region. In certain embodiments, the separated sub-pools of molecules can then be separately released or removed from the array into reaction chambers for further chemical processing. In certain embodiments, the step of releasing is optional, not generally limited, and can include dehybridizing the molecules by heating, using denaturing agents, or exposing the molecules to buffer of pH≥12. In certain embodiments, the chambers or areas of the array containing different immobilized oligonucleotides can be positioned to allow the contents of each chamber or area to flow into an array of wells for further chemical processing.

In certain embodiments, the method includes reacting the at least one building block B, with a molecule of formula (IV) to form a sub-pool of molecules of formula (I) or (II), wherein B is as defined above for formula (I). In certain embodiments, the building block B can be added to the container before, during, or after the molecule of formula (I), (II), or (IV). It is understood that the container can contain solvents, and co-reactants under acidic, basic, or neutral conditions, depending on the coupling chemistry that is used to react the building block B with a molecule of formula (II) or (I).

A method of purifying molecules is disclosed. In certain embodiments, the term "providing" is not generally limited, and can include purchasing or synthesis. In certain embodiments, provided that the U is an oligonucleotide and G contains T, then contaminants, including defective multifunctional molecules, can be removed or decreased by annealing the oligonucleotide U and T together to form a loop structure. In certain embodiments, PCR can selectively react with molecules of formula (I) to form molecules of formula (I), where G is double stranded. In certain embodiments, the PCR can selectively react with molecules of formula (I) over defective multifunctional molecules by a ratio of at least 2:1, including at least 5:1, including at least 10:1. In certain embodiments, the selection agent can selectively digest or breakdown defective multifunctional molecules relative to molecules of formula (I) by a ratio of at least 2:1, including at least 5:1, including at least 10:1. The selection agent is not generally limited so long as it is capable of selectively digesting or breaking down defective multifunctional molecules. In certain embodiments, selection agents include, RecJf, Exonuclease VII, and Mung Bean Nuclease.

A method of analyzing a synthetic yield is disclosed. In certain embodiments, the method includes providing a pool of multifunctional molecules, including molecules of formula (IV), and amplifying G of the multifunctional molecules by PCR to form a pool of pre-reaction copies of G. In certain embodiments of the method, a benefit of forming a pre-reaction pool of copies of G can be the quantification of the total number of multifunctional molecules present in a sample before one or more synthetic steps is performed. In certain embodiments of the method, a benefit of forming a pre-reaction pool of copies of G can be the quantification of the relative abundance of different multifunctional molecules present in the sample before one or more synthetic steps is performed. In certain embodiments of the method, the pool of multifunctional molecules, including molecules of formula (IV) can be reacted with one or more building blocks B to form a multifunctional verification molecule, including a molecule of Formula (I). In certain embodiments, the method includes amplifying at least one oligonucleotide G to form a pool of post-reaction copies of G. In certain embodiments, a benefit of forming a pool of post-reaction copies of G can be the quantification of the total number of multifunctional molecules present in a sample after one or more synthetic steps is performed. In certain embodiments of the method, a benefit of forming a pool of post-reaction copies of G can be the quantification of the relative abundance of different multifunctional molecules present in the sample after one or more synthetic steps is performed. In certain embodiments, the pool of pre-reaction copies of G and post-reaction copies of G can be sequenced by conventional oligonucleotide sequencing techniques to provide pre-reaction sequencing data and post-reaction sequencing data. In certain embodiments, the method includes comparing the pre-reaction sequencing data to the post-reaction sequencing data. The method of comparing pre-reaction sequencing data to the post-reaction sequencing data is not generally limited. In certain embodiments, one benefit of comparing pre-reaction sequencing data to the post-reaction sequencing data is that the synthetic yield of one or more reaction steps can be calculated, including the identification of low yield steps.

The use of DNA-Encoded Libraries requires the synthesis of millions to billions of unique compounds. To date there is no means of synthesizing a library which can be readily evaluated to ascertain the relative yield of each reaction done in the formation of that library. The present disclosed describes just such a library, and provides a facile means for evaluating the outcome of hundreds to thousands or even millions of chemical reactions simultaneously. Any method of performing such an analysis would be best if it could give very high quality results with exceptionally small amounts of material, so that the remainder of the library can be used for its intended purpose. The ability of PCR to amplify signals of exceptionally small size, and the ability of Next-GenSequencing to deliver vast quantities of high-resolution data presents an opportunity to measure the yield of many reactions simultaneously.

Many attractive DNA-encoded combinatorial chemistry libraries are comprised of a series of bifunctional molecules. In this regime, a bifunctional building block molecule is reacted with a first reactive functional group on DNA. The first functional group of the bifunctional molecule, which reacts with the reactive moiety on the DNA, is termed the 'upstream' functional group. The second functional group on the bifunctional building block, which is available for reaction with an incoming building block, is termed the 'downstream' building block. In the synthesis of DNA-encoded combinatorial chemistry libraries wherein the products of a synthetic step possess a downstream functional group that is different from the downstream functional group of the previous step, the yield of all reactions in that step can be measured with this method. In addition, for such libraries comprised of multiple synthetic steps wherein the downstream functional group changes at the end of each step, the yield of chemical reactions for all such steps can be measured simultaneously from a single DNA sequencing experiment. In addition, a method of synthesizing such a library is disclosed that is uniquely predisposed to the making of these measurements using an exceptionally small amount of sample so that the remainder of the synthesized library can be used for its intended purpose.

To achieve this benefit, molecules of formula (I) are used, $G-L-B_{(K)}-Q-U$, where G is an oligonucleotide, L is a linker linking $B_{(K)}$ to G, the sequence of G encodes the identity of $B_{(K)}$, Q is a building block or chemical functional group bonded to $B_{(K)}$, and U is an oligonucleotide linked to Q and complementary to a sequence in G. Under denaturing conditions, the distance between T and U can be determined by (a) the number of bases between T and the locus of L's attachment to G, (b) the length of L, (c) the length of $B_{(K)}$-Q, and (c) the linker between U and Q. When T is near or adjacent to the locus of L's attachment to G, when L is a PEG linker about 4 PEG units long, $B_{(K)}$ is about the size of a tetrapeptide, and U is linked to Q by a linker about 4 PEG units long, then the approximate number of atoms between T and U will be 50-80 atoms. An overestimate of the mean distance between T and U can be had by modeling the length of the linkers and $B_{(K)}$ as a fully extended chain of 50 links of length 150 pm (an average length of a carbon-carbon bond). These distances range between 7.5 nm and 11.9 nm. The effective concentration of U and T in this estimate would thus be higher than 10 mM. A more accurate estimation of the distance between U and T and therefore their effective concentration could be had by modeling the PEG linkers as ideal chains, but the estimation of 10 mM effective concentration is a clear underestimation in this example, and it is applicable and instructive. Molecules of formula (I) can be selectively separated from molecules of formula (II). Consider the case where (a) U-Q was reacted with molecules of formula (II) at only a slight molar excess over all of G (the sum of molecules of formula (I) and formula (II)), and (b) all of G is diluted to 1 uM in a buffer suitable for PCR, and (c) where a 100-fold excess of a silencing primer, U*, is added, wherein U* is comprised of the same sequence as U, but which has an extra 3' dideoxy nucleotide making it incapable of extension by a polymerase. If this solution is heated above the melting point of U, and then allowed to cool, a competition for annealing to T will occur wherein, U linked to G through Q and $B_{(K)}$ will have an effective concentration of ~10 mM, U* will have a concentration of 100 uM (100-fold less), and U not linked to G through Q and $B_{(K)}$ will have a concentration of at most 1 uM (which is 100-fold less than U*).

Because the effective concentration of U linked to G in molecules of formula (I) is ~100-fold greater than the concentration of U*, then only ~1% of molecules of formula (I) will be silenced by U*, and that silencing will happen in a way that is independent of information in coding regions in G and so will not skew sequencing results. Because the concentration of U* over U-Q unlinked to G will be =,>100-fold, then ~99% of molecules of formula (II) will be primed by U*, and therefore be incapable of being made double-stranded by PCR. Likewise, less than 1% of the molecules of formula (II) will be primed by any U-Q molecules present that are unlinked to G, and any of them that are primed so will be primed in a manner that is independent of information in coding regions in G and so will not skew sequencing results.

If a polymerase and dNTPs are added, and a single-cycle of PCR is done, the vast majority of copies of G that will be made double-stranded will be those primed by U-linked to G. Any method that preferentially removes ssDNA in the presence of dsDNA can then be used to purify the sample, and produce a sample that is very highly enriched in molecules of formula (I), and which represent those encoded molecules B(K) which have been fully and correctly synthesized.

The purified sample of molecules of formula (I) can be amplified by PCR, and sequenced by NextGenSequencing to identify compounds that have been fully formed. Comparison of the relative distribution of different molecules of formula (I) to an internal standard of known concentration or abundance, and comparison to a sample of the library taken prior to reaction of Q-U to G-L-$B_{(K)}$ which contains the same internal standard, can illuminate which reactions of which building blocks proceed to good yield and which do not.

It will be appreciated by one skilled in the art, that due to the reliance on enzymatic means used in this approach, the measurements can be made using microliter/sub-microliter scale samples, or nanogram/sub-nanogram scale samples.

Because the cost of producing DNA-encoded combinatorial chemistry libraries is high, this can be an important advantage.

This approach uses DNA polymerases and it will also be appreciated by one skilled in the art that because DNA polymerases extend primers in a 5' to 3' direction, that the primer U used in this invention anneal to a 3' end of G. It will also be appreciated that the position of T in G will function more optimally if placed near the locus of L's attachment to G.

It will be appreciated by one skilled in the art that Q could also be a chromatography reagent and enable purification of molecules of formula (I) by affinity chromatography. It will also be appreciated that such a scheme will enable use of the method with the Linker at either the 5' or 3' end of G, but that this scheme may require use of larger quantities of sample if purification is to be done on an affinity chromatography column.

It will be appreciated by one skilled in the art that taking measurements of chemical yield by this method can be done after any one single synthetic step in the production of a library, after every synthetic step, or after all or a series of steps.

It will be appreciated by one skilled in the art that the methods described herein can be readily applied to tagging correctly formed molecules of formula (II) with a U-Q construct to form molecules of formula (I). It will also be appreciated that the methods applied herein are readily applied tagging in-correctly formed molecules of formula (II) with a U-Q construct to form molecules of formula (I).

Without loss of generality, consider a hypothetical example wherein an arbitrary step of synthesis of a library, Step Orange, involves coupling a downstream functional group amine to an upstream functional group carboxylic acid on an incoming building block. The crude product of this reaction will comprise amides, representing places where the reaction has proceeded correctly, and amines, representing places where the reaction has failed. The reaction products could be analyzed by tagging the unreacted amines with a U-Q construct wherein Q was chosen to possess an acid fluoride capable of reacting with the remaining amines. This approach would be effective, as long Q is chosen to be reactive with the amine and unreactive with any reactive moieties present in the building blocks used in Step Orange, or any other exposed reactive moieties present on the nascent encoded molecule.

In general, tagging molecules of formula (II) which have in-correctly formed may require selection of a reactive functional group for Q which is highly reactive, because an inherently low reactivity of molecules of formula (II) may be the reason those molecules failed to react in the first place. It will be appreciated that an inherently low reactivity of incoming building blocks is just as likely a cause for poor yields. It will also be appreciated that the construction of these libraries typically requires the use reaction conditions having been chosen for their generality across a set of reactants, rather than being specifically tailored and optimized for high yields for each given pair building blocks. Thus, highly reactive functional groups for Q may not be strictly necessary, but they may prove more useful in some cases than others.

It will be appreciated by one skilled in the art, that strategies for acquiring useful and pertinent data can include the use of different reactive groups for Q, and different reaction conditions applied to several different samples in parallel. This ability is greatly enabled by the exceptionally small sample sizes required for execution of this method.

More Detail Regarding the Challenges

The high cost of drug discovery and the increasing need to discover molecules with unique and desirable properties for use in medicine, research, biotechnology, agriculture, food production, and industry has given rise to the field of combinatorial chemistry.

Discovery of a molecule with highly desirable properties for a particular desired application may not always be straightforward. For instance, molecules that bind a target protein or biological macromolecule or polymolecular structure can be profoundly difficult to rationally design. When faced with the challenge of discovering a molecule for which structural designs ascertained from first principles are impossible or inefficient, combinatorial chemistry has presented itself as a viable tool. Combinatorial chemistry enables discovery through the following general process: (a) the researcher makes the best hypotheses available about the more general properties and structure a molecule may have in order to fit the criteria for the desired application, (b) the researcher designs and synthesizes a very large number of molecules, termed a library, possessing the general properties or structures hypothesized, (c) the library is tested to determine if any of the library members possess the characteristics for the desired application.

Where information is limited, those hypotheses that can be made about the structure of a desirable molecule will be looser and less well-defined, than in cases where there is a large body of knowledge to inform those hypotheses. Where more data informs structural hypotheses, libraries with smaller complexity or diversity, e.g., $1e^4$-$1e^7$ unique members, focuses tightly on regions of chemical shape space hypothesized to be rich in desirable structures may be more successful. In cases where little or no data exists, libraries with far larger complexity and which sample greater regions of shape space and sample it more deeply, e.g., $1e^5$-$1e^{14}$ unique members, may be required for success.

Combinatorial chemistry allows the synthesis of libraries of compounds on this scale by split-and-pool or sort and react chemical synthesis methods. Typical split-and-pool libraries start with a functional group that is incorporated in the chain of a polymeric solid support like a polystyrene bead. A group of several thousand to several million beads are split into a series of vessels and the beads in each vessel are reacted with a different chemical subunit or building block. When the reaction is complete, all the beads are pooled, mixed well, and re-split into anew series of reaction vessels for a second step of chemical synthesis with the same or a different set of building blocks. The split-and-pool reaction process is repeated until synthesis is complete. The number of compounds made by this method is only limited by the number of beads that can be handled in the process, and the number of building blocks used at each step. These two parameters will define the complexity of such a library. For example if there are 5 chemical subunits at each of 4 steps, the $5^4$=625 members will make up the library. Similarly, if there are 52 building blocks at the first step, 3 at the second, 384 at the third, and 96 at the fourth, then 52×5×384×96=3,833,856 library members will have been produced.

The library of molecules can then be tested to ascertain which of them possesses the desired characteristics for the chosen application. Identification of such molecules can be challenging because the amount of molecules produced on a single bead can be quite small and therefore hard to identify. It is generally understood in the combinatorial chemistry community that for libraries tailored appropriately to the amount of structural data available to guide the design of the library, that larger libraries are expected to meet with a greater probability of possessing highly desirable members. However, for any given amount of library produced, the greater the complexity, or the greater the number of unique molecules in the library, the lower the copy number, or the number of copies of each member there will be. Therefore, as a library increases in complexity and in the probability of having a successful member, the total amount of that successful member diminishes along with the ability of the combinatorial chemist to correctly identify it.

The constrained optimization the combinatorial chemist then faces is to make a library with sufficient complexity to possess desirable members, while also making enough copies of each member of the library to ensure the desirable members are accurately identified. In general, as the complexity of a library increases, the size of the solid support should also decrease; as that support size decreases, so does the amount of sample available for analysis and identification.

In general, given sufficient resources one could synthesize a very large combinatorial library of $10^{10}$ unique members on polystyrene beads in a one-bead-one-compound library. But if each polystyrene bead were a sphere of volume 0.1 microliters, then the volume of the $10^{10}$-member library would be >1 cubic meter—enough to fill an ordinary hot tub or spa, perhaps to overflowing. And while industrial chemical processes are often carried out on this scale, processes of this complexity are very rarely carried out on this scale. A library on this scale also brings up the question of testing such a library, and producing the molecular target for those tests. Such a test could easily require a kilogram of purified protein and the cost of producing that much drug target protein would be astronomical for many drug target proteins.

DNA-encoded combinatorial chemistry libraries seek to improve this situation. The fact that PCR can vastly amplify a single template strand of DNA with great accuracy, and the fact that amplified strands can be sequenced readily, enables the possibility of reducing the size of the solid support down to a single molecule of DNA. Thus, the ability to both make extremely vast libraries (e.g., $10^6$-$10^{14}$ unique members), and also identify successful molecules from that population could be achieved by tethering a combinatorial chemistry library member to a strand of DNA in a way that establishes a correspondence between the DNA sequence and the identity of the library member. A selection experiment is then performed. A "selection" being an experiment physically isolating those members of the library population possessing desired traits from those members that do not. DNA encoding trait-positive library members is then amplified by PCR, and sequencing of the DNA identifies the trait-positive library member. In this manner libraries of vast complexity can be synthesized, and trait-positive individuals identified from vanishingly small sample sizes.

New DNA sequencing technologies capable of returning $10^6$-$10^8$ unique sequences facilitates markedly improved analysis of DNA-encoded libraries. "Deep sequencing" data enables robust statistical analysis of very complex chemical libraries. These kinds of analysis not only identify specific individual members of the library appropriate for the chosen application, but can also reveal previously unknown general traits that confer 'fitness' for the application on library members. Typically, a DNA library is deep sequenced prior to a selection experiment designed to physically separate individuals that are more fit for the application at hand from individuals that are less fit. The population after the experiment is deep sequenced and comparison of the two data sets shows which individuals are more fit because their relative frequency in the population increases. Those individuals that are less fit will be identified because their relative frequency in the population diminishes. However, DNA-encoded combinatorial chemistry methods can make libraries with complexities that far outstrip the most powerful current deep sequencing technologies. Although deep sequencing enables a vast improvement in the utility and success of DNA-encoded combinatorial libraries, it still only provides a statistical under-sampling of the data that is theoretically available.

The problem of this data under-sampling is compounded by the fact that not every step in the combinatorial chemistry process proceeds with perfect efficiency. A loss of fidelity is observed because some reactions do not go to completion, and some reactions form by-products. Therefore, there is not always perfect clarity that the DNA sequence returned by deep sequencing represents the actual molecule it encoded, but may on occasion represent a truncation product or a product altered by side reactions.

Compounding the problem of under sampling is the problem of synthetic fidelity. Not every reaction used in making a combinatorial library will be perfectly efficient. This means that some DNAs in a DNA encoded library are not tethered to the molecule they encode, but are rather tethered to truncation products resulting from incomplete incorporation of one or more building blocks, or they are tethered to analogous compounds resulting from the incorporation of a by-product or side reaction. Data analysis thus suffers because some of the genotypes observed to be surviving selection represent molecules other than the ones they encode.

Identification of Encoded Portions

In some embodiments, the present disclosure provides multifunctional molecules that are molecular probes having a correspondence between the DNA gene sequence in oligonucleotide G and the identity of the encoded portion or molecule the gene encodes.

In some embodiments, the correspondence is established as follows. In some embodiments, the gene library is prepared in a manner that makes the coding regions single-stranded and any non-coding regions double-stranded.

In certain embodiments, establishing a correspondence between the next chosen coding region sequences and the next building blocks will be accomplished by sorting the library into subpools based on the coding sequences at the chosen coding region, and performing chemistry to install different building blocks on different sub-pools. In certain embodiments, this sorting is accomplished by sequence specific hybridization of the single-stranded coding sequences to complementary oligos immobilized on an array of solid supports termed a hybridization array. In certain embodiments, this sorting is accomplished by providing different oligonucleotides that are complementary to sequences within different coding oligonucleotides, performing chemistry to install different building blocks on the anti-codon oligonucleotides, allowing the building block-laden oligonucleotides to anneal to the coding oligonucleotides in a sequence specific fashion. Upon such annealing, the building block can be transferred to a reactive moiety on the coding strand, or the building block-laden oligo can be ligated to the coding strand, or to another building block-laden oligo.

The construction of hybridization arrays is described below. Briefly, in certain embodiments, a hybridization array is an array of spatially separated features containing solid supports. In certain embodiments, on these supports are covalently tethered ssDNA oligos with sequences complementary to the sequences of the coding region being sorted. In certain embodiments, by flowing a library of molecules of formula (I), (II), or (IV) bearing a plurality of coding sequences over or through a solid support bearing a given anti-coding sequence, the members of the library having the complementary coding sequence can be specifically immobilized. In certain embodiments, flowing the library over or through an array of solid supports each of which bears a different immobilized anti-coding sequence will sort the library into subpools based on coding sequence. In certain embodiments, each sequence-specific subpool can then be independently reacted with a specific building block (positional building block) to establish a sequence to building block correspondence. This synthesis will be described in more detail below, and can be performed on the hybridization array, or after the subpools have been eluted in subpools off of the array into a suitable environment, such as separate containers, for reaction.

Coding regions in the oligonucleotides G may also encode other information. In certain embodiments, after translation of the library is complete, it may be desirable to sort the library based on index coding region sequences. In certain embodiments, index coding region sequences can encode the intended purpose, or the selection history of its corresponding subpool of the library. For example, libraries for multiple targets can be translated simultaneously together, and then sorted by the index coding region into subpools. Subpools intended for different targets, and/or for selections under different conditions can be thus separated from each other and made ready for use in their respective applications. The selection history of a library member undergoing multiple rounds of selections for various properties can thus be recorded in the index region.

Many kinds of chemistry are available for use in this invention. In theory, any chemical reaction could be used that does not chemically alter DNA. Reactions that are known to be DNA compatible include but are not limited to: Wittig reactions, Heck reactions, homer-Wads-worth-Emmons reactions, Henry reactions, Suzuki couplings, Sonogashira couplings, Huisgen reactions, reductive aminations, reductive alkylations, peptide bond reactions, peptoid bond forming reactions, acylations, SN2 reactions, SNAr reactions, sulfonylations, ureations, thioureations, carbamoylations, formation of benzimidazoles, imidazolidinones, quinazolinones, isoindolinones, thiazoles, imidazopyridines, diol cleavages to form glyoxals, Diels-Alder reactions, indole-styrene couplings, Michael additions, alkene-alkyne oxidative couplings, aldol reactions, Fmoc-deprotections, trifluoroacetamide deprotections, Alloc-deprotections, Nvoc deprotections and Boc-deprotections. (See, Handbook for DNA-Encoded Chemistry (Goodnow R. A., Jr., Ed.) pp 319-347, 2014 Wiley, New York. March, Advanced Organic Chemistry, fourth edition, New York: John Wiley and Sons (1992), Chapters 10 to 16; Carey and Sundberg, Advanced Organic Chemistry, Part B, Plenum (1990), Chapters 1-11; and Coltman et al., Principles and Applications of Organotransition Metal Chemistry, University Science Books, Mill Valley, Calif. (1987), Chapters 13 to 20; each of which is incorporated herein by reference in its entirety.)

It will be understood by one skilled in the art that a vast assortment of different combinatorial scaffolds can be incorporated into multifunctional molecules of the present disclosure. Examples of the kinds of general classes of scaffolds include but are not limited to the following: (a) chains of bifunctional building blocks connected end to end, peptides and peptoids are two examples of this kind of scaffold; it will be appreciated that not every bifunctional building block in the chain will have the same pair of functional groups, and that some building blocks may have only one functional group, e.g. terminal building blocks, (b) branching chains of bifunctional building blocks that include some tri-functional building blocks, and may or may not include mono-functional building blocks, (c) molecules comprised of a single polyfunctional building block, and a set of monofunctional building blocks; in one embodiment, such a molecule may have a polyfunctional building block that acts as a central core, to which other mono-functional building blocks are added as diversity elements, (d) molecules comprised of two or more polyfunctional building blocks to which are connected a set of monofunctional or bifunctional building blocks as diversity elements, (e) any of the above scaffolds that includes formation of ring by reacting a moiety on the linker or a building block installed at an earlier step with a moiety on a building block or the linker installed at a later step. Other scaffolds or chemical structural phyla can also be incorporated, and these general structural scaffolds are only limited by the ingenuity of the practitioner in designing the chemical pathways to synthesize them.

In certain embodiments, ion-exchange chromatography facilitates the chemical reactions performed on substrates tethered to DNA in two ways. For reactions conducted in aqueous solvent, purification can be readily accomplished by pouring the reaction over an ion exchange resin like DEAE-SEPHAROSE®, or TOYOPEARL® SuperQ 650M. In certain embodiments, the DNA will be bound to the resin by ion exchange, and unused reactants, by-products and other reaction components can be washed away with aqueous buffers, organic solvents or mixtures of both. For reactions that work best in organic solvent, a real problem exists: DNA has very poor solubility in organic solvents, and such reactions suffer from low yields. In these cases, library DNA can be immobilized on ion exchange resin, residual water washed away by a water miscible organic solvent, and the reaction performed in an organic solvent that may or may not be water miscible. See, for example, R. M. Franzini, et. al. Bioconjugate Chemistry 2014 25 (8), 1453-1461, and references therein. Many types and kinds of ion exchange media exist, all having differing properties that may be more or less suited to different chemistries or applications, and which are commercially available from numerous companies like THERMOFISHER®, SIGMA ALDRICH®, DOW®, DIAION® and TOYOPEARL® to name only a few. It will be appreciated that there are many possible means and media by which library DNA might be immobilized or solubilized for the purpose of conducting a chemical reaction to install a building block, or remove a protecting group, or activate a moiety for further modification, that are not listed here.

In certain embodiments, a hybridization array comprises a device for sorting a heterogeneous mixture of ssDNA sequences by sequence specific hybridization of those sequences to complementary oligos that are immobilized in a position-addressable format. See, for example, U.S. Pat. No. 5,759,779. It will be appreciated that hybridization arrays may take on many physical forms. In certain embodiments, hybridization arrays possess the ability for a heterogenous sample or ssDNAs (ie. a library of compounds of formula (I)) to come into contact with complementary oligos that have been immobilized on a surface of the array. The complementary oligos will be immobilized on a surface of the array in a manner that enables, allows or facilitates sequence-specific hybridization of the ssDNA to the immobilized oligo, thereby immobilizing the ssDNA as well. In certain embodiments, ssDNAs that have been immobilized through a common sequence can be independently removed from the array to form a subpool.

In some embodiments, the hybridization array will be a chassis comprising a rectangular sheet of plastic between 0.1 and 100 mm thick into which has been cut a series of holes, termed 'features'. In certain embodiments, on the underside and top of the sheet will be adhered filter membranes. In certain embodiments, in the features, trapped between the filter membranes, will be a solid surface or collection of solid surfaces, termed 'solid support.' In certain embodiments, a single sequence of oligo will be immobilized on the solid support in any given feature.

In certain embodiments, a library of molecules of formula (I or II) can be sorted on the array by allowing an aqueous solution of the library to flow over and through the features. In certain embodiments, as members of the library come in contact with oligos in features bearing complementary sequences, they become immobilized within the feature. In certain embodiments, after hybridization is complete, the features of the array can be positioned over a receiver vessel, like a 96-well plate or a 384-well plate. In certain embodiments, addition of an alkaline solution that causes the de-hybridization of DNA can be added to each feature and the solution will carry the library, now mobile, into the receiver vessel. Other methods of de-hybridizing are also possible, like the use of hot buffer, or denaturing agents. Thus, in certain embodiments, a library of molecules can be sorted into subpools in a sequence specific manner.

It will be appreciated, that the chassis described above could be comprised of plastic, ceramic, glass, polymer or metal. It will be appreciated that the solid supports can be comprised of a resin, glass, metal, plastic, polymer or ceramic, and that the supports can be porous or non-porous. It will be appreciated that higher surface areas on the solid supports allow for larger amounts of complementary oligos to be immobilized and larger amounts of library subpools can be captured in the feature. It will be appreciated that the solid supports can be held in their respective features by filter membranes made of nylon, plastic, cloth, polymer, glass, ceramic or metal. It will be appreciated that the solid supports can be held within their respective features by means other than filter membranes, like glue, adhesives, or covalent bonding of the support to the chassis and/or to other supports. It will be appreciated that the features may or may not be holes in a chassis, but independent constructs which can be taken out of or placed in a chassis. It will be appreciated that the shape of the chassis need not be rectangular with features arranged in 2 dimensions, but could be cylinder or rectangular prism with features arranged in one dimension or 3 dimensions. See, for example, U.S. Pat. No. 5,759,779.

Libraries of molecules of formula (I) can be thought of as populations of phenotypes tethered to their respective genotypes. Such a population can be subjected to a selection pressure that removes less fit individuals from the population, and allows more fit members to survive. The oligonucleotide G genotypes of the second generation population—those surviving selection—can be amplified by PCR, re-translated, and subjected to another, more stringent selection for the same trait, or selected for some orthogonal trait. The subpopulation surviving a selection can also be sequenced, typically using deep sequencing or next-generation sequencing techniques, and the sequencing data can be analyzed to identify the encoded portions (phenotypes) that are the most fit.

This invention is illustrated by but not limited by the following examples. Those skilled in the art will recognize many equivalent techniques for accomplishing the steps or portions of the steps enumerated herein.

EXAMPLES

An embodiment of a molecule of formula (I) is constructed as follows.

Example 1: Construction of a 8×10⁹-Member Gene Library (Molecules of Formula G)

Design and Provision of Codons for the Gene Library.

96 double stranded DNA ("dsDNA") sequences are provided or purchased from a gene synthesis company like Genscript in Piscataway N.J., Synbio Technologies in Monmouth Junction N.J., Biomatik of Wilmington Del., Epoch Life Sciences of Sugarland Tex., among others. These sequences comprise 5 coding regions of 20 bases each. Each coding region is flanked by a 20-base non-coding region (making a total of 6 non-coding regions). All of the coding region sequences are unique, and chosen to be un-cross-reactive with other coding regions and with the non-coding regions. The 5 non-coding regions in a DNA molecule have different sequences, but the sequence at each position is conserved across all the DNAs. All coding and non-coding regions are designed to have similar melting temperatures (typically between 58° C. and 62° C.). Coding and non-coding regions are designed in silico as follows. DNA sequences are generated randomly in silico.

Once generated, the sequence melting temperature and thermodynamic properties (delta H, delta S and delta G of melting) are calculated using the nearest neighbor method. If the calculated Tm and other thermodynamic properties are not within the predefined range desired for the library, the sequence is rejected. Acceptable sequences are subjected to analysis by sequence similarity algorithms. Sequences predicted by the algorithm to be sufficiently non-homologous are presumed to be non-cross-reactive, and are kept. Others are rejected. Coding and non-coding regions are sometimes chosen from empirical lists of oligos shown to be non-cross hybridizing. See, Giaever G, Chu A, Ni L, Connelly C, Riles L, et al. (2002) Functional profiling of the *Saccharomyces cerevisiae* genome. Nature 418: 387-391. This reference lists 10,000 non-cross-reactive oligos. The Tm of each is calculated and those falling within the predefined range are analyzed by sequence homology algorithms. Those which are sufficiently non-homologous are retained.

Each non-coding region contains a unique restriction site. The non-coding region at the 5' end of the template strand contains a SacI recognition site at bases 13-18 from the 5' end. The non-coding region at the 3' end of the coding strand contains an EcoRI restriction site at bases 14-19 from the 3' end of the template strand. The second, third, fourth and fifth non-coding regions from the 5' end of the template strand have HindIII, NcoI, NsiI, and SphI recognition sites respectively at bases 8-13.

Example 1b. The DNAs are Restriction Digested to De-Couple all Codons from Each Other The DNA sequences are pooled and dissolved in CUTSMART® buffer from New England Biolabs (NEB, Massachusetts) at a concentration of about 20 µg/ml. The internal restriction enzymes, HINDIII-HF®, NCOI-HF, NSII-HF® and SPHI-HF® from NEB are added and the digestion is done for 1 hour at 37° C., following enzyme the manufacturer's protocols. The enzymes are heat inactivated at 80° C. for 20 minutes. After inactivation, the reaction is held at 60° C. for 30 minutes, then cooled to 45° C. and held for 30 minutes, and then cooled to 16° C.

Example 1c. The Codons are Combinatorially Re-Assorted to Produce a Gene Library To re-assemble the individual codons produced in the digestion reaction into full-length genes, T4 DNA Ligase from NEB is added to the reaction to 50 U/ml, dithiothreitol (DTT, Thermo Fisher Scientific, Massachusetts) is added to 10 mM, and adenosine 5'-triphosphate (ATP, from NEB) is added to 1 mM in accordance with the manufacturer's protocol. The ligation reaction is performed for 2 hours, and the product is purified by agarose gel electrophoresis. Because the sticky-ends produced by digestion at one site of a provided gene will anneal to the sticky-ends of all the other digestion products at the same site, a complete combinatorial re-assortment will occur. Thus, 96 provided genes comprised of 5 codons each would produce 965 genes. Because there are 96 coding sequences at each of 5 coding positions, there are $96^5=8 \times 10^9$ combinations or library members.

Example 2a: Prepare the Gene Library by an Alternate Method

Example 1 describes the combinatorial re-assortment of all codons simultaneously by restriction digestion at all internal non-coding regions of provided library gene sequences followed by ligation. This process is optionally done in a step-wise fashion instead of simultaneously. The same reaction conditions found in Example 1b in the step "the DNAs are restriction digested to de-couple all codons from each other," are used except, a single restriction endonuclease is added, instead of all the endonucleases. Then using the same reaction conditions found in Example 1c in the step, "the codons are combinatorially re-assorted to produce a gene library," the restriction digestion products are re-ligated together. The ligation product is purified by agarose gel electrophoresis, amplified by PCR, and then cut by the next restriction enzyme. The process is repeated until the gene library is complete.

Example 2b: Prepare the Gene Library by a Second Alternate Method

Examples 1b and 1e describe the combinatorial re-assortment of all codons by restriction digestion at all internal non-coding regions followed by ligation. In some embodiments, incomplete combinatorial re-assortment of codons to produce a population with markedly lower complexity would be advantageous. Such a gene library is produced by first splitting a mixture of the 96 gene sequences described in Example 1 into several aliquots. Each aliquot is then restriction digested by a different combination of 1-3 restriction enzymes, using the reaction conditions found in Example 1b or in Example 2a. After heat inactivation of the restriction enzymes, the independent digestion products are re-ligated as per the protocol in Example 1c. The products are pooled and purified by agarose gel electrophoresis, amplified by PCR, and the rest of library preparation and translation and selection is done as per Examples following.

Example 2c. Prepare the Gene Library by a Third Alternate Method

A library is prepared with coding regions of from about 4 to about 40 nucleotides. The library is prepared as before with the following exceptions. The library is constructed by purchasing two sets of oligos, a coding strand set of oligos and an anti-coding strand set of oligos. Each set comprises as many subsets as there are coding regions, and as many different sequences are in each subset as there are different coding sequences at a coding region. Each oligo in each subset of the coding strand oligos comprises a coding sequence and optionally a 5' non-coding region. Each oligo in each subset of the anti-coding strand oligos comprises an anti-coding sequence and optionally a 5' non-coding region complement. In order to facilitate ligations downstream in the process, all the oligos except those for the 5' termini of the coding and anti-coding strands are purchased with 5' phosphorylations, or are phosphorylated with T4 PNK from NEB as per the manufacturer's protocol. The subset of oligos possessing the coding strand 5' terminal coding sequences is combined in T4 DNA Ligase buffer from NEB with the subset possessing the 3' terminal anti-coding sequences, and the two sets are allowed to hybridize. Doing so produces a product comprising a single-stranded 5' overhang non-coding region on the coding strand, a double-stranded coding region, and an optional single stranded 5' overhang non-coding region on the anti-coding strand. This hybridization procedure is carried out separately for each coding/anti-coding pair of oligo subsets. For example, the subset of sequences encoding the second coding region from the 5' end is hybridized with its complementary anti-coding subset, the subset encoding the third coding region from the 5' end with its complementary subset, and so forth. The hybridized subset pairs are pooled and optionally purified by agarose gel electrophoresis. If the genes in the library possess non-coding regions of 1 base or more in length, and if the non-coding regions between coding regions are unique, then equimolar amounts of each hybridized subset pair are added to a single vessel. The single-stranded non-coding regions hybridize, and are ligated to each other by T4 DNA Ligase from NEB using the manufacturer's protocol. If the non-coding regions are 1 base in length or more, but are not unique, then two adjacent hybridized subsets are added to one vessel, the single-stranded non-coding regions anneal, and are ligated with T4 DNA Ligase. Upon reaction completion, the product is optionally purified by agarose gel electrophoresis, and a third hybridized subset that is adjacent to one of the ends of ligated product is added, annealed and ligated. This process is repeated until construction of the library is complete. It will be appreciated that libraries comprised of arbitrary numbers of coding regions are constructed by this method. For current purposes, libraries of more than 20 coding regions may be impractical for reasons unrelated to library construction. It will be appreciated that blunt ligations are commonly performed by those skilled in the art, and that coding regions do ligate without intervening non-coding regions, but that for hybridized subsets possessing no non-coding regions at either end, that the ligation provides both sense and anti-sense products. Products possessing the correct sense are purified away from products possessing anti-sense by preparing the library and sorting it on all hybridization arrays sequentially. The portion of the library that is captured on the array at each hybridization step possesses the correct sense. It will be appreciated that a non-coding region comprised only of a unique restriction site sequence is an attractive option of this method.

Example 2d. Purchase of a Gene Library

Gene libraries like the one described in Examples 1 and 2 can be purchased from Twist Bioscience of 500 Terry Francois Boulevard, San Francisco, Calif. 94158.

Example 3: Prepare Translation-Ready, Single-Stranded Oligonucleotide G

Example 3 a. Amplify the Gene Library by PCR

A T7 promoter is appended to the 5' end of the non-template strand by extension PCR using these reactants for a 50 μL reaction: 5× PHUSION® High-Fidelity DNA Polymerase ("PHUSION® Polymerase", NEB), 10 μL; deoxynucleotide (dNTP) solution mix 200 μM final concentration; forward primer, final concentration 750 nM; reverse primer final concentration, 750 nM; template (enough template should be used to adequately oversample the library); dimethyl sulfoxide (DMSO), 2.5 uL; "PHUSION® Polymerase", 2 μL. Perform the PCR using an annealing temperature of 57° C., and an extension temperature of 72° C. Anneal for 5 seconds each cycle; extend for 5 seconds each cycle. Analyze the product by agarose gel electrophoresis.

Example 3b. Transcribe the DNA into RNA

Without purification of the PCR product, a 250 μL transcription reaction is done with the following reactants: PCR product, 25 μL; RNAse-free water, 90 μL; nucleoside triphosphate's (NTP), 6 mM final concentration in each; 5×T7 buffer, 50 μL; NEB T7 RNA polymerase 250 units; optionally, RNasin® Ribonuclease Inhibitors (Promega Corporation, WI) can be added to 200 U/ml; optionally, pyrophosphatase can be added to 10 μg/ml. 5×T7 buffer contains: 1M HEPES-KOH (4-(2-hydroxyethyl)-1-piperazineethane-sulfonic acid) pH 7.5; 150 mM magnesium acetate; 10 mM spermidine; 200 mM DTT. The reaction is conducted at 37° C. for 4 hours. The RNA is purified by lithium chloride precipitation. Dilute the transcription reaction with 1 volume of water. Add LiCl to 3M. Spin at maximum g, at 4° C. for at least 1 hr. Decant the supernatant and keep it. A clean pellet will be a clear, glassy, gel that can be difficult to dissolve. Alternating gentle warming (a minute at 70° C.) and gentle vortexing will cause the pellet to re-suspend. Analyze by agarose gel electrophoresis, quantitate and freeze as soon as possible to avoid degradation. See, for example, Analytical Biochemistry 195, p 207-213. (1991), and Analytical Biochemistry 220, p 420-423, (1994).

Example 3c. Reverse Transcribe the RNA into DNA

The single stranded RNA ("ssRNA") is reverse transcribed in a 2 step procedure using SUPERSCRIPT® III Reverse Transcriptase from Thermo Fisher Scientific and the supplied First Strand Buffer. The first step is done with these final concentrations of the following components: dNTP's, 660 μM each; RNA template, ~5 μM; primer, 5.25 μM. The Step 1 components are heated to 65° C. for 5 minutes, then iced for at least 2 min. The Step 2 components final concentrations are: First Strand Buffer, 1×; DTT, 5 mM; RNase Inhibitor (NEB), 0.01 U/uL, SUPERSCRIPT® III Reverse Transcriptase, 0.2 U/μl. The Step 2 components are combined, warmed to 37° C., and after the Step 1 components have been iced 2 minutes, the Step 2 mix is added to the Step 1 mix. The combined parts are reacted at 37° C. for 12 hours. The reaction is followed by agarose gel electrophoresis. Take samples of the reaction, of known starting material RNA and of known product, or known product analog like PCR product library. Add ethylenediaminetetraacetic acid ("EDTA") to all samples, heat to 65° C., 2 minutes, flash cool, and then run on an agarose gel. ssRNA should resolve from complementary DNA ("cDNA") product. The cDNA product is purified by adding 1.5 volumes of isopropanol and ammonium acetate to 2.5 M, followed by centrifugation at 48,000 g for 1 hour. The cDNA pellet is re-suspended in distilled water ("dH$_2$O") and the RNA strand is hydrolyzed by adding LiOH to pH 13. The solution is heated to 95° C. for 10 minutes. 1.05 equivalents of primers specific for the non-coding regions are added, the pH is brought to neutral with tris(hydroxymethyl)aminomethane ("Tris") and acetic acid, and the reaction is allowed to cool to room temperature slowly, whereupon it is concentrated and optionally purified.

Example 4: Prepare G with a Linker and Reactive Functional Group

Example 4a: Prepare G with a Linker at the 5' End During Reverse Transcription

A reactive chemical functional group can be tethered to the oligonucleotide by following the protocols in Example 3, in the paragraph "Reverse Transcribe the RNA into DNA" except the primer used for the reverse-transcription reaction is provided with linker that placed at or near the 5' end of the primer. Appropriate linkers are commercially available and include alkyl chains, peptide chains, polyethylene glycol chains, and they are discussed more fully herein. Appropriate chemical functional groups are commercially available already tethered to linkers and include amines, alkynes, carboxylic acids, thiols, alcohols, and are discussed more fully herein. One example of linkered functional group that can be purchased as part of an oligonucleotide primer is N4-TriGl-Amino 2'deoxycytidine (from IBA, Goettingen, Germany). Primers as described here can be purchased from DNA oligo synthesis companies like Sigma Aldrich, Integrated DNA Technologies of Coralville, Iowa, or Eurofins MWG of Louisville, Ky.

Example 4b: Prepare G with a Linker at the 5' End by Ligation

A primer bearing a linkered reactive chemical functional group as described in Example 4a can also be ligated to the 5' end of G by providing such a primer, then first, phosphorylating the 5' hydroxyl of G using Polynucleotide Kinase from NEB following the manufacturer's protocol. Then ligating the primer using T4 RNA Ligase 1 from NEB in the buffer and under conditions following the manufacturer's protocol. In addition, such a ligation may be made more efficient if a second primer is provided whose 5' end is complementary to the 5' end of G, and whose 3' end is complementary to the 3' end of the linker-bearing primer. This bridging primer will help hold the two reactive moieties together for ligation. A primer bearing a linkered functional group can also have a hairpin region and form a stem loop that accomplishes the same task of holding the ends of the primer and G together for ligation. In such a case the linkered functional group may be positioned farther from the 5' end of the primer, or at or near the 5' end. In any of these cases, the linkered functional group should be positioned where it does not interfere with ligation, or with upstream or downstream processing. Immobilizing the ligatable ends together by either of these to methods enables ligation using T4 DNA Ligase from NEB, by use of the manufacturer's protocol. For example, a template library of oligonucleotides G is buffer exchanged using ZEBA™ 30K MWCO (Thermo Fisher Scientific, MA) centrifugal concentrators to 50 mM Tris-HCl, 10 mM $MgCl_2$, 25 mM NaCl, pH 7.5@25° C. 1.1 equivalents of primer bearing a linkered functional group and a hairpin with a stem loop and a 5' overhang complementary to the 5' end of oligonucleotide G are added. The reaction is warmed to 65° C. for 10 min and allowed to cool to 15° C. below the melting temp of the complementary overhang over 15 min and incubated at that temp for 15 min. DTT is added to 10 mM, ATP is added to 1 mM, and T4 DNA Ligase is added to 50 U/mL. The ligation reaction is run at room temp for 12 hours, then the enzyme is heat inactivated at 65° C. for 10 min, and the reaction cooled slowly to room temperature. The reaction is buffer exchanged and concentrated with a 30K molecular weight cut-off (MWCO) centrifugal concentrator into 150 mM NaCl, 20 mM citrate, 15 mM Tris, 0.02% sodium dodecyl sulfate ("SDS"), 0.05% Tween20 (from Sigma-Aldrich), pH 7.5.

Example 4c: Prepare G with a Linker and Reactive Functional Group at the 3' End

A primer bearing a linkered reactive chemical functional group as described in Example 4a, but which bears its linkered functional group at or near its 3' end, can also be purchased from the same suppliers, and can also be ligated to the 3' end of G by providing such a primer, then first, phosphorylating the 5' hydroxyl of the primer using Polynucleotide Kinase from NEB following the manufacturer's protocol. Then ligating the primer using T4 RNA ligase from NEB following the manufacturer's protocol. In addition, such a ligation may be made more efficient if a second primer is provided whose 3' end is complementary to the 3' end of G, and whose 5' end is complementary to the 5' end of the linker-bearing primer. This bridging primer will help hold the two reactive moieties together for ligation. A primer bearing a linkered functional group can also have a hairpin region and form a stem loop that accomplishes the same task of holding the ends of the primer and G together for ligation. In such a case the linkered functional group may be positioned farther from the 3' end of the primer, or at or near the 3' end. In any of these cases, the linkered functional group should be positioned where it does not interfere with ligation, or with upstream or downstream processing. Immobilizing the ligatable ends together by either of these two methods enables ligation using T4 DNA Ligase from NEB, by use of the manufacturer's protocol. For example, a template oligonucleotide library, G, is buffer exchanged using ZEBA™ 30K MWCO (Thermo Fisher Scientific, MA) centrifugal concentrators to 50 mM Tris-HCl, 10 mM $MgCl_2$, 25 mM NaCl, pH 7.5@25° C. 1.1 equivalents of hairpin-containing primers bearing linkered functional groups, and a stem loop overhang sequence complementary to the 3' end of G are added. The reaction is warmed to 65° C. for 10 min and allowed to cool to 15° C. below the Tm of the overhang sequence, and held at that temp for 15 min. DTT is added to 10 mM, ATP is added to 1 mM, and T4 DNA Ligase is added to 50 U/mL. The ligation reaction is run at room temp for 12 hours, then the enzyme is heat inactivated at 65° C. for 10 min, and the reaction cooled slowly to room temperature. The reaction is buffer exchanged and concentrated with a 30K molecular weight cut-off (MWCO) centrifugal concentrator into 150 mM NaCl, 20 mM citrate, 15 mM Tris, 0.02% sodium dodecyl sulfate ("SDS"), 0.05% Tween20 (from Sigma-Aldrich), pH 7.5.

Example 4d: Ligate a Reaction Site Linked to a Primer to a Template Strand with Other Chemistry Other methods of covalently tethering the reaction site linked primer can be used, including chemical or enzymatic methods. Such linked primers are ligated by chemical means using reagents such as water soluble carbodiimide and cyanogen bromide as done by, Shabarova, et al. (1991) Nucleic Acids Research, 19, 4247-4251), Fed-erova, et al. (1996) Nucleosides and Nucleotides, 15, 1137-1147, GryaZnov, Sergei M. et al. J. Am. Chem. Soc., vol. 115: 3808-3809 (1993), and Carriero and Damlia (2003) Journal of Organic Chemistry, 68, 8328-8338. Chemical ligation is optionally done using 5M cyanogen bromide in aceto-nitrile, in a 1:10 v/v ratio with 5' phosphorylated DNA in a buffer containing 1M MES and 20 mM $MgCl_2$ at pH 7.6, the reaction being performed at 0 degrees for 5 minutes. Ligations can also be performed by topoisomerases, polymerases and ligases using manufacturer's protocols.

Example 5. Prepare Molecules of Formula (IV), and Formula (II) by Sorting a Library of Oligonucleotide G into Sub-Pools, and Performing Sub-Pool-Specific Chemistry Example 5a. Preparation of a Hybridization Array Hybridization arrays are constructed of a TECAFORM™ (Acetal Copolymer) chassis ~2 mm thick, with holes cut by a computer numerical control machine. A nylon 40 micron mesh from ELKO FILTERING is adhered to the bottom of the chassis using NP200 double-sided tape from Nitto Denko. The holes are then filled with a solid support of CM SEPHAROSE® resin (Sigma Aldrich) which has been functionalized with an azido-group. The resin is functionalized using azido-PEG-amine with 8 PEG units purchased from Broadpharm (San Diego, Calif.). 45 ml of packed CM SEPHAROSE® is loaded into a fritted funnel and washed with DMF. The resin is then suspended in 90 ml of DMF and reacted with 4.5 mM azido-PEG-amine, 75 mM EDC, 7.5 mM HOAt, 12 hours at room temp. The resin is washed with DMF, water, isopropanol and stored in ethanol 20% at 4° C. A nylon 40 micron mesh is then adhered to the top of the chassis. The azido group allows alkyne-linked oligos to be tethered to the solid support using click chemistry. Placing the array in an array-to-well-plate adapter, and stationing the adapter over a well plate enables capture oligos to be 'clicked' onto the azido-SEPHAROSE® in register. A 30 µl solution containing 1 nmol of alkynyl oligo, copper sulfate, 625 µM tris(3-hydroxy-propyl-triazolyl-methyl)amine ("THPTA") (ligand), 3.1 mM amino-guanidine, 12.5 mM ascorbate, 12.5 mM phosphate buffer pH 7, 100 mM, is added to each well of the array-to-well-plate adapter and allowed to adsorb onto the SEPHAROSE® support. After 10 minutes, the solution is spun in a centrifuge out of the array and into the plate, whereupon it is re-pipetted in register back onto the array for a second pass at the reaction. After a second 10 minute reaction, the reaction solutions are spun into the well plate, and the well plate is set aside. The array is washed well with 1 mM EDTA, and stored in phosphate buffer solution ("PBS") with 0.05% sodium azide. The reaction solutions are each diluted to 100 µl with dH$_2$O, loaded onto diethylaminoethyl (DEAE) ion exchange resin, washed with dH$_2$O to remove all reagents and reaction by-products except for any un-incorporated oligo. These solutions are analyzed by high-performance liquid chromatography (HPLC) to ascertain the degree of incorporation by disappearance of starting material. One array bears oligos complementary to one coding position in the template library. A separate array is made for each coding position.

Example 5b. Sorting a Library by Sequence-Specific Hybridization

The hybridization-ready library is diluted to 13 ml in 1× Hybridization Buffer (2× saline sodium citrate (SSC), +15 mM Tris pH7.4+0.005% TRITON® X100, 0.02% SDS, 0.05% sodium azide). 10 µg of transfer RNA ("tRNA") are added to block non-specific nucleic acid binding sites. An array is chosen corresponding to the desired coding position in the template library. The array is placed in a chamber that provides 1-2 mm of clearance on either side, and the 13 ml library solution is poured in. The chamber is sealed and rocked gently for 48 hours at 37° C. Optionally, the array is placed in a device that allows the solution containing the library to be pumped in a directed fashioned though the various features in a pre-patterned path as a means to sort the library on the array faster.

Example 5c. Eluting Sorted Library Off of a Hybridization Array

The array is washed by unsealing the chamber and replacing the hybridization solution with fresh 1× hybridization buffer, followed by rocking at 37° C. for 30 minutes. The wash is repeated 3 times with hybridization buffer, then 2 times with ¼× hybridization buffer. The library is then eluted off of the array. The array is placed in an array-to-well-plate adapter, and 30 µl of 10 mM NaOH, 0.005% TRITON® X-100 is added to each well and incubated 2 minutes. The solution is spun in a centrifuge through the array into a well plate. The elution procedure is done 3 times. The sorted library solutions are neutralized by adding 9 µl of 1M Tris pH 7.4 and 9 µl of 1M HOAc, in that order, to each well.

Example 5d. Performing a Peptoid Coupling Chemical Step on a Sorted Library

15 µl aliquots of SuperQ 650M resin are added to each well of a filter plate, and washed with 100 µl of 10 mM HOAc. The sorted library is transferred in register from the well plate into which it is spun during elution off of the hybridization array into the well plate bearing the ion exchange resin. The resin and library are washed 1×90 µl with 10 mM HOAc, 2×90 µl with dH$_2$O, 2×90 µl DMF, 1×90 µl piperidine. Separately, make a solution containing 100 mM sodium chloroacetate and 150 mM 4-(4,6-Dimethoxy-1,3,5-triazin-2-yl)-4-methyl morpholinium chloride in methanol. Add 40 µl of this solution to each well of resin and react at room temperature for 30 minutes. Wash the resin 3×90 µl methanol, then repeat the coupling and wash 3×90 µl methanol, 3×90 µl DMSO. Separately, make 2M (or saturated where necessary) solutions of secondary amines in DMSO. Add 40 µl of one secondary amine solution to each well of resin and react at 37° C. for 12 hrs. Wash the resin 3×90 µl DMSO, 3×90 µl 10 mM acetic acid (HOAc), 3×90 µl dH$_2$O. Elute the DNA library off of the ion exchange resin with 1.5 M NaCl, 50 mM NaOH, 0.005% TRITON® X-100 in 3×30 µl portions. Pool all the reactions, and neutralize the solution by addition of Tris to 15 mM and HOAc to pH 7.4. Concentrate and buffer exchange into 1× hybridization buffer.

Example 5e. Complete the Synthesis of the Library

Using the protocols above for sorting the library on hybridization arrays, and using the protocols above for performing peptide or peptoid chemistry, or those below in other Examples for performing other chemical steps, more steps of sorting and synthesis are done and the library is fully translated.

Example 6a: Prepare Molecules of Formula (I) when U is an Oligonucleotide Complementary to T A library of molecules of formula (II) is prepared as per the examples above wherein the reactive chemical group linked to G by L is an amine, and the first step of chemistry is a peptoid coupling step as described in Example 5, and wherein the secondary amines used in the reaction are bifunctional molecules bearing secondary amines and carboxylic acids. The product molecules of formula (II), which have correctly reacted, will bear carboxylic acid moieties. The library of molecules of formula (II) is sorted on a hybridization array into sub-pools and each sub-pool is reacted with a specific bifunctional compound bearing an amine, and also bearing an alkyne. The peptide coupling reaction is performed under conditions like those for coupling chloroacetate in Example 5 except the amine is reacted with the acid in 50/50 DMF/methanol. All molecules of formula (II) are pooled, and purified by ethanol precipitation, ion exchange chromatography, or reverse-phase chromatography. The pool of molecules of formula (II) is now comprised of encoded molecules bearing alkynes if both steps of synthesis were successful, of encoded molecules bearing carboxylic acids if only the first step of synthesis was successful, and of oligonucleotide G bearing a linker and free amine if neither step proceeded successfully. A sample of this pool of molecules of formula (II) is taken and set aside. Some or all of the rest is dissolved in 100 mM phosphate buffer. To it is added copper sulfate to 625 µM, THPTA (ligand) to 3.1 mM, amino-guanidine to 12.5 mM, ascorbate to 12.5 mM, and 1.1 mole equivalents of a molecule of formula (III) comprising an oligonucleotide of sequence U linked to an azide (Q). The reaction is run at room temperature for 4 hours. (See Hong, V., Presolski, Stanislav I., Ma, C. and Finn, M. G. (2009), Analysis and Optimization of Copper-Catalyzed Azide-Alkyne Cycloaddition for Bioconjugation. Angewandte Chemie International Edition, 48: 9879-9883.) Any of the sample of molecules of formula (II) that are not used in this reaction can be used in further steps of chemistry in library synthesis, and then used in this step as described.

Example 6b. Purify Molecules of Formula (I) when U is an Oligonucleotide Complementary to T At the end of the reaction linking Q to B$_{(K)}$, the reaction should be diluted to 1 uM in combined molecules of formula (I) and (II) in a buffer suitable for PCR; (2) a silencing primer, U*, which bears the sequence of U and an additional base at the 3' end having a dideoxy ribose, and which is therefore incapable of enabling elongation by a polymerase, is added to a concentration of 100 uM; (3) the solution is heated above the Tm of U hybridized to T; (4) the solution is allowed to cool to 37 C; (5) Taq polymerase and dNTPs are added so that each moiety of G that is primed by U can be made double-stranded; (6) when the reaction is complete, Exonuclease VII (from NEB) is used in accordance with the manufacturer's protocol to digest all single-stranded DNA. Taq polymerase and others like BST DNA Polymerase Large Fragment (from NEB), Bsu DNA Polymerase, Large Fragment (from NEB), T4 DNA Polymerase (from NEB) may be suitable for making the second strand synthesis application described here. In addition, other enzymes may be suitable for digestion of single stranded DNA including Bean Nuclease (from NEB), RecJf (from NEB). Note that attention should be paid to the activities and vicissitudes of each enzyme in the design of each experiment. For example, when using Mung Bean Nuclease, there should be no overhangs where U anneals to T, because that nuclease cleaves overhangs as an endonuclease. When using Exonuclease VII, or RecJ$_f$, this provision should be unnecessary. This information is readily available on the NEB website.

Example 7a: Prepare Molecules of Formula (I) when U is a Chromatography Reagent

A library of molecules of formula (II) is prepared as per the examples above wherein the reactive chemical group linked to G by L is an amine, and the first step of chemistry is a peptoid coupling step as described in Example 5, and wherein the secondary amines used in the reaction are bifunctional molecules bearing secondary amines and carboxylic acids. The product molecules of formula (II), which have correctly reacted, will bear carboxylic acid moieties. The library of molecules of formula (II) is sorted on a hybridization array into sub-pools and each sub-pool is reacted with a specific bifunctional compound bearing an amine, and also bearing an alkyne. The peptide coupling reaction is performed under conditions like those for coupling chloroacetate in Example 5 except the amine-alkyne is reacted with the acid in 50/50 DMF/methanol. All molecules of formula (II) are pooled, and purified by ethanol precipitation, ion exchange chromatography, or reverse-phase chromatography. The pool of molecules of formula (II) is now comprised of encoded molecules bearing alkynes if both steps of synthesis were successful, of encoded molecules bearing carboxylic acids if only the first step of synthesis was successful, and of oligonucleotide G bearing a linker and free amine if neither step proceeded successfully. A sample of this pool of molecules of formula (II) is taken and set aside. Some or all of the rest is dissolved in 100 mM phosphate buffer. To it is added copper sulfate to 625 µM, THPTA (ligand) to 3.1 mM, amino-guanidine to 12.5 mM, ascorbate to 12.5 mM, and 10 mole equivalents of a molecule of formula (III) comprising a molecule of biotin (U) linked to an azide (Q). A molecule of formula (III) as described here can be purchased from Sigma Aldrich (SKU: 762024). The reaction is run at room temperature for 4 hours. (See Hong, V., Presolski, Stanislav I., Ma, C. and Finn, M. G. (2009), Analysis and Optimization of Copper-Catalyzed Azide-Alkyne Cycloaddition for Bioconjugation. Angewandte Chemie International Edition, 48: 9879-9883.) Any of the sample of molecules of formula (II) that are not used in this reaction can be used in further steps of chemistry in library synthesis, and then used in this step as described.

Example 7b. Purify Molecules of Formula (I) when U is a Chromatography Reagent

The product of the reaction in Example 7 is passed over a streptavidin column, like a HiTrap Streptavidin High Performance Column sold by GE Healthcare through Sigma Aldrich (SKU: GE17-5112-01). Molecules of formula (I) will be captured on the column and molecules of formula (II) will not.

Example 8. Analysis of Chemical Reaction Yields

The sample of the pool of molecules of formula (II) that was taken prior to reaction with molecules of formula (III) (as in Example 6 or 7) is amplified by PCR and sequenced. This sample represents the relative distribution of molecules prior to the reaction with molecules of formula (III). The purified pool of molecules of formula (I) can be amplified by PCR and sequenced. This sample represents the pool of molecules that survived selection and therefore were correctly synthesized. Comparison and analysis of pre-reaction sequences and post-reaction sequences will illuminate which chemical reactions proceed with good yield and which do not.

Example 8a. Formation of Molecules of Formula (I), and Evaluation of Chemical Yields after Synthetic Steps Producing No Downstream Functional Groups In prior steps, Q is chosen to have a reactive functional group consonant with the downstream functional group of the final building block installed. In cases where a final building block lacking a downstream building block is required, Q is chosen to possess a reactive functional group consonant with the downstream functional block of the penultimate building block. Other Q's with functional groups consonant with reactive functional groups from prior steps may also be used. A library of molecules of formula (II) is prepared as per the examples above wherein the reactive chemical group linked to G by L is an amine, and the first step of chemistry is a peptoid coupling step as described in Example 5, and wherein the secondary amines used in the reaction are bifunctional molecules bearing secondary amines and carboxylic acids. A sample of this library is taken and set aside and termed the 'pre-analytical sample.' (This pre-analytical sample can be analyzed as if it were a final building block installed, as per Examples 6a and 6b, 7a and 7b, and Example 8.) The product molecules of formula (II), which have correctly reacted, will bear carboxylic acid moieties. The library of molecules of formula (II) is sorted on a hybridization array into sub-pools and each sub-pool is reacted with a specific monofunctional compound bearing an amine but bearing no downstream functional group. The peptide coupling reaction is performed under conditions like those for coupling chloroacetate in Example 5 except the amine is reacted with the acid in 50/50 DMF/methanol. All molecules of formula (II) are pooled, and purified by ethanol precipitation, ion exchange chromatography, or reverse-phase chromatography. The pool of molecules of formula (II) is now comprised of encoded molecules bearing no downstream functional group if both steps of synthesis were successful, comprised of encoded molecules bearing carboxylic acids as the downstream functional group if only the first step of synthesis was successful, and of oligonucleotide G bearing a linker and free amine, or a chloroacetate, as the downstream functional group if neither step proceeded successfully. A sample of this pool of molecules of formula (II) is taken and set aside and termed the 'pre-Q reaction sample.' Some or all of the rest is dissolved in 50 mM MES buffer, pH6.5. To it is added and 1.1 mole equivalents of a molecule of formula (III) comprising an oligonucleotide of sequence U linked to Q wherein Q comprises a hydroxyl amine. The reaction is run at room temperature for 4 hours. (See Hong, V., Presolski, Stanislav I., Ma, C. and Finn, M. G. (2009), Analysis and Optimization of Copper-Catalyzed Azide-Alkyne Cycloaddition for Bioconjugation. Angewandte Chemie International Edition, 48: 9879-9883.) Any of the sample of molecules of formula (II) that are not used in this reaction can be used in further steps of chemistry in library synthesis, and then used in this step as described.

Example 9. Perform Selections with Molecules of Formula (I)

The pool of molecules of formula (I) can be used in selections for molecules possessing desired properties. See Examples 9a-9h.

Example 9a. Select Ligands that Bind to Protein Target of Interest

5 µg of streptavidin in 100 µl of PBS is immobilized in 4 wells of a MAXISORP™ plate with rocking at 4° C. overnight. The wells are washed with PBST 4×340 ul. Two of the wells are blocked with 200 µl of casein, and 2 others with BSA at 5 mg/ml for 2 hours at room temperature. The wells are washed with PBST 4×340 µl. 5 µg of a biotinylated target protein in 100 µl of PBS are added to a well blocked with casein, and to a well blocked with BSA and incubated with rocking at room temperature for 1 hour (for a protocol on the biotinylation of proteins, see Elia, G. 2010. Protein Biotinylation. Current Protocols in Protein Science. 60:3.6: 3.6.1-3.6.21). A 100 µl aliquot of the translated library in PBS with Tween 20 (PBST) is added to each of the wells that did NOT receive the target protein, and 100 µl of PBST is added to the two wells that did receive target protein. The samples are incubated with rocking at room temperature for 1 hour. The buffer is carefully aspirated from the wells containing immobilized target protein and PBST only. The buffer containing library in wells without the target is carefully transferred to target-containing wells. 100 µl PBST are added to the wells without target. All are incubated for 4 hours with rocking at room temperature. The library is carefully removed with a pipette and stored. The wells are washed with 4×340 µl PBST. To elute library members binding tightly to the target protein, an excess of biotin in 100 µl of PBST is added to the wells and incubated for 1 hour at 37° C. The buffer is carefully aspirated and used as the template for a PCR reaction.

Example 9b. Analyze Selection Results

PCR products from the library before and after selection are submitted for deep sequencing using the primers and protocols required by the DNA Sequencing service provider. Providers include Seqmatic of Fremont Calif., and Elim BioPharm, Hayward, Calif. The coding sequences at the terminal and internal coding regions of each sequenced strand are analyzed to deduce the building blocks used in synthesis of the encoded portion. The relative frequency of identified library members before selection and after suggests the degree to which the library member is enriched in the population by the selection. Analysis of the various chemical subgroups comprising the library members surviving selection shows the degree to which those moieties confer fitness on a library member and are used to evolve more fit molecules or to predict analogous molecules for independent synthesis and analysis.

Example 9c. Performing Selections for Binding a Target Molecule Using Alternative Means Selections to identify library members capable of binding a target molecule are performed as per Example 1 with the exception that target molecules are immobilized on the surface of plastic plates like IMMULON® plates, MAXISORP® plates or other plates commonly used for immobilizing biological macromolecules for ELISA, or the target molecules are biotinylated and immobilized on streptavidin-coated surfaces or neutravidin-coated surfaces, or avidin-coated surfaces, including magnetic beads, beads made of synthetic polymers, beads made of polysaccharides or modified polysaccharides, plate wells, tubes, and resins. It will be understood that selections to identify library members possessing a desired trait will be performed in buffers that are compatible with DNA, compatible with keeping any target molecules in a native conformation, compatible with any enzymes used in the selection or amplification process, and compatible with identification of trait-positive library members. Such buffers include, but are not limited to, buffers made with phosphate, citrate, and TRIS. Such buffers may also include, but not be limited to, salts of potassium, sodium, ammonium, calcium, magnesium and other cations, and chloride, iodide, acetate, phosphate, citrate, and other anions. Such buffers may include, but not be limited to, surfactants like TWEEN®, TRITON™, and Chaps (3-[(3-Cholamidopropyl)dimethylammonio]-1-propanesulfonate).

Example 9d. Selection for Binders with Long Off-Rates

Selections are performed to identify individuals in the library population possessing the ability to bind a target molecule as described in Example 1. Individuals that bind the target molecule with long off-rates are selected for as follows. Target molecules are immobilized by being biotinylated and incubated with a streptavidin-coated surface, or optionally immobilized without biotinylation on plastic surface like a MAXISORP® plate or some other plate suitable for binding proteins for ELISA-like assays, or by a method described in Example 35, or by another method. The library population is incubated with the immobilized target for 0.1 to 8 hours in an appropriate buffer. The duration of the incubation will depend on the estimated number of copies of each individual library member in the sample and on the number of target molecules immobilized. With higher copy numbers of individuals and higher loads of target molecule, the duration may diminish. With smaller copy numbers and/or smaller loads of a target molecule, the duration may extend. An objective is to ensure each individual in the population has the opportunity to fully interact with the target. After this incubation of the library with an immobilized target, binders in the library are presumed to be bound to the target. At this point, an excess of non-immobilized target is added to the system and the incubation is continued for about 1 to about 24 hours. Any individuals bound to an immobilized target that possesses a short off-rate, may release from the immobilized target and upon re-binding will partition into being bound by free target and immobile target. Individuals binding with long off-rates will remain bound to the immobilized target. Washing the immobilization surface preferentially removes non-binders and binders with fast off-rates, thus selecting for individuals with long off-rates. Amplification of the DNA encoding the long off-rate binders is done as per Example 1.

Example 9e. Selections with Mobile Targets

Selections are performed in which target molecules are biotinylated, and then incubated with a library for an appropriate duration. The mixture is then immobilized for example on a streptavidin surface, whereupon the target becomes immobilized, and any library members bound to the target become immobilized as well. Washing the surface removes non-binders. Amplification of the DNA encoding the binders is done as per Example 1.

Example 9f. Selections for Target Specificity

Selections are performed to identify individuals in the library population that bind to a desired target molecule to the exclusion of other anti-target molecules. The anti-target molecule (or molecules if there are more than one) are biotinylated and immobilized on a streptavidin-coated surface, or optionally immobilized on a plastic surface like a MAXISORP® plate or some other plate suitable for binding proteins for ELISA-like assays. In a separate container, target molecules are immobilized by being biotinylated and incubated with a streptavidin-coated surface, or optionally immobilized on plastic surface like a MAXISORP® plate or some other plate suitable binding proteins for ELISA-like assays. The library is first incubated with the anti-target. This depletes the population of individuals that bind the anti-target molecule(s). After this incubation with anti-target, the library is transferred to a container with desired target and incubated for an appropriate duration. Washing removes non-binders. Amplification of the DNA encoding the long off-rate binders is done as per Example 1. Target binders identified will have an improved probability of selectively binding the target over the anti-target(s). Optionally, the selection for affinity for a target is performed by immobilizing the target, adding free, mobile anti-target in excess, and then adding library and incubating for an appropriate duration. Under this regime, individuals with affinity for the anti-target are preferentially bound by the anti-target because it is present in excess, and can thus be removed during washing of the surface. Amplification of the DNA encoding the binders is done as per Example 1.

Example 9g. Selections Based on Differential Mobility

Selections are performed based on the ability of an individual in the library population to interact with a target molecule or polymacromolecular structure based on a difference in mobility of the library member when in a complex formed when a target molecule or polymacromolecular structure is interacting with the library member. Allowing target molecules or structures and library members to interact, and then passing the mixture through a size exclusion medium causes library members that are not interacting with a target molecule or structure to become physically separated from library members that are interacting, because the complex of the interacting library member and target molecule or structure will be larger than non-interacting library members, and therefore move through the medium with a different mobility. It will be appreciated that the difference in mobility can be a function of diffusion in the absence of a size exclusion medium, that the mobility can be induced by various means including but not limited to gravity flow, electrophoresis, and diffusion.

Example 9h. General Strategies for Other Selections

It will be appreciated by one skilled in the art that selections are performed for virtually any property provided an assay is designed that either (a) physically separates individuals in the library population that possess the desired property from individuals that do not possess it, or (b) allows DNA encoding individuals in the library population that possess the desired property to be preferentially amplified over DNA encoding library members that do not possess the property. Many methods of immobilization of target molecules are known in the art including tagging target molecules with His-tags and immobilizing on nickel surfaces, tagging target molecules with flag tags and immobilizing with anti-flag antibodies, or tagging target molecules with a linker and covalently immobilizing it to a surface. It will be appreciated that the order of the events that allow library members to bind targets and that allows targets to be immobilized is done in various orders as is dictated or enabled by the method of immobilization used. It will be appreciated that selections are performed wherein immobilization or physical separation of trait-positive individuals from trait-negative individuals is not required. For example, trait-positive individuals recruit factors enabling amplification of their DNA, where trait-negative members do not. Trait-positive individuals become tagged with a PCR primer, whereas trait-negative individuals do not. Any process differentially amplifying trait-positive individuals is suitable for use.

Example 10. Removal of Q and/or U

Many reactions are known which are reversible, and many reversible chemical linkers are commercially available (see Leriche, et al., Bioorganic and Medicinal Chemistry, v20, issue 2, 15 Jan. 2012, pp. 571-582; doi:10.1016/j.bmc.2011.07.048, and references contained therein for a review of cleavable chemical linkers and their uses in biochemistry.) A pool of molecules of formula (I) is prepared using a molecule of formula (III) in which U is biotin, Q is azide, and U is linked to Q with a cleavable disulfide linker. Synthesis is performed exactly as per Example 7. This version of a molecule of formula (III) is commercially available from Broadpharm (9380 Waples Street, Suite 101, San Diego, Calif. 92121; SKU: BP-22877. Broadpharm also sells photocleavable linkers and PC cleavable linkers). The disulfide bridge in the linker can be cleaved by buffer exchange into PBS and addition of DTT or TCEP to 10 mM, at 37 C for 8 hours. Upon cleavage of the linker between Q and U, the pool of resultant molecules can be used in selections like those described in Example 9. A pool of molecules of formula (I) is prepared using a molecule of formula (III) in which U is an oligonucleotide complementary to T, which is a sequence within the 3' terminal non-coding region of G, Q is azide, and U is linked to Q with a cleavable disulfide linker. Synthesis is performed exactly as per Example 6. Cleavage of the disulfide bridge can be effected after buffer exchange reaction with DTT or TCEP as above.

Example 11. Alternative Reaction Sites and Linkers

It will be appreciated that a modified base bearing a reactive site for installing a linker, or bearing a linker and a reactive site can be placed at any desirable locations in the oligonucleotide during the course of synthesis. Oligos bearing linkers and reactive sites may also contain bases or modified bases bearing functional groups that facilitate processing, like biotin or fluorophores, or other labels. Such oligos can be purchased from reputable vendors of custom DNA oligos like IDT of Coralville, Iowa, Sigma Aldrich, or Eurofins MWG of Louisville, Ky.

A library using a different initial reactive site from a free amine is made in several ways. One method is to cap an existing initial reactive site functional group with a bifunctional molecule bearing the desired initial reactive site functional group. Prepare a library exactly as per Examples 4a-4d above, except that for each oligo bearing an amine reaction site on which a different initial reaction site is desired, a peptide bond is formed to the initial reactive site functional group amine with a bifunctional compound bearing a carboxylic acid and the desired initial reactive site functional group, using the peptide coupling reaction conditions listed in Example 5d for coupling chloroacetate. For example, 5-hydroxy pentanoic acid could be reacted with the free amine to form a peptide bond, and establish the hydroxyl functional group as the initial reactive site for synthesizing the library.

A second method is to incorporate a different base modified with a different reactive site that enables or facilitates installation of other desired initial reactive site functional groups. One such base is 5-Ethynyl-dU-CE Phosphoramidite ("ethynyl-dU") sold by Glen Research in Virginia. It is optionally modified with a bifunctional linker compound bearing an azide and the desired initial reactive site functional group. For example, 5-azido pentanoic acid could be reacted with the alkynyl moiety in a "click" reaction (Huisgen reaction) with conditions found in Example 25, establishing the carboxylic acid as the initial reactive site functional group. As another representative but non-inclusive example, 5-azido 1-pentanal could be reacted with the alkynyl moiety in a "click" reaction (Huisgen reaction), establishing the aldehyde as the initial reactive site functional group. As another representative example, 4-azido, 1-bromomethylbenzene could be reacted with the alkynyl moiety in a "click" reaction (Huisgen reaction), establishing the benzyl halide as the initial reactive site functional group. This base is optionally used as an alkynyl initial reactive site for library synthesis using chemistries appropriate for alkynes chosen from Examples 12-35. Desirable initial reactive sites include, but are not limited to, amines, azides, carboxylic acids, aldehydes, alkenes, acryloyl groups, benzyl halides, halides alpha to carbonyl groups, and 1,3-dienes.

A third method is to incorporate a base modified with both a linker and an initial reactive site functional group during synthesis of the oligonucleotides installed in G by the various means described in Examples 4a-4d. For example, incorporating 5'-Dimethoxytrityl-N6-benzoyl-N8-[6-(trifluoroacetylamino)-hex-1-yl]-8-amino-2'-deoxyAdenosine-3'-[(2-cyanoethyl)-(N,N-diisopropyl)]-phosphoramidite (also called amino-modifier C6 dA, purchased from Glen Research, Sterling Va.), at strategic locations during the synthesis of the oligonucleotide would establish a free amine as the initial reactive site functional group and a 6 carbon alkyl chain as the linker, as would incorporating 5'-Dimethoxytrityl-N2-[6-(trifluoroacetylamino)-hex-1-yl]-2'-deoxyGuanosine-3'-[(2-cyanoethyl)-(N,N-diisopropyl)]-phosphoramidite (also called amino-modifier C6 dG, purchased from Glen Research, Sterling, Va.). Incorporating 5'-Dimethoxytrityl-5-[3-methyl-acrylate]-2'-deoxyUridine,3'-[(2-cyanoethyl)-(N,N-diisopropyl)]-phosphoramidite (also called Carboxy dT, purchased from Glen Research, Sterling Va.) at strategic locations during the synthesis of the oligonucelotide would establish a carboxylic acid as the initial reactive site functional group and a 2 carbon chain as the linker. Incorporating 5'-Dimethoxytrityl-5-[N-((9-fluorenyl-methoxycarbonyl)-aminohexyl)-3-acrylimido]-2'-deoxyUridine,3'-[(2-cyanoethyl)-(N,N-diisopropyl)]-phosphoramidite (also called Fmoc-amino modifier C6 dT, Glen Research, Sterling, Va.) at strategic locations during the synthesis of the oligonucleotide would establish an Fmoc-protected amine as the initial reactive site functional group and a 6 carbon alkyl chain as the linker. Incorporating 5'-Dimethoxytrityl-5-(octa-1,7-diynyl)-2'-deoxyuridine, 3'-[(2-cyanoethyl)-(N,N-diisopropyl)]-phosphoramidite (also called C8 alkyne dT, Glen Research, Sterling Va.) at strategic locations during the synthesis of the oligonucelotide would establish an alkyne as the initial reactive site functional group and an 8 carbon chain as the linker. Incorporating 5'-(4,4'-Dimethoxytrityl)-5-[N-(6-(3-benzoylthiopropanoyl)-aminohexyl)-3-acrylamido]-2'deoxyuridine, 3'-[(2-cyanoethyl)-(N,N-diisopropyl)]-phosphoramidite (also called S-Bz-Thiol-Modifier C6-dT, Glen Research, Sterling Va.) at strategic locations during the synthesis of the oligonucleotide would establish a thiol as the initial reactive site functional group and a 14 atom chain as the linker. Incorporating N4-TriGl-Amino 2'deoxycytidine (from IBA GmbH, Goettingen, Germany) at strategic locations during the synthesis of the oligonucleotide would establish an amine as the initial reactive site functional group and a 3-ethylene glycol unit chain as the linker. It will be appreciated that these modified bases can be installed during synthesis of primers by many reputable and skilled commercial vendors like Sigma Aldrich, Integrated DNA Technologies of Coralville, Iowa, or Eurofins MWG of Louisville, Ky.

Suitable linkers perform two critical functions: (i) they covalently tether the oligonucleotide G to a building block, and (ii) they do not interfere with other critical functions in the synthesis or use of molecules of formula (I). Thus, in some embodiments, the linkers are alkyl chains or PEG chains because (a) they are highly flexible, allowing appropriate and free presentation of the encoded portions to target molecules during selections, and (b) because they are relatively chemically inert and typically do not undergo side reactions during synthesis of molecules of formula (I). To adequately perform most, but not all tasks, linkers need not comprise an overall length greater than about 8 PEG units. It will be appreciated by one skilled in the art that when performing selections in which the library DNA should be kept as far from the target molecule or target structure or target surface as possible, that considerably longer linkers, and/or considerably stiffer linkers, like a peptide alpha helix, would be useful and attractive. Other desirable linkers could include polyglycine, polyalanine, or polypeptides. Linkers are also used which incorporate a fluorophore, a radiolabel, or a functional moiety used to bind a molecule of formula (I) in a manner that is orthogonal to binding to the encoded portion, or that is complementary to the binding of the encoded portion. For example, it may be necessary to incorporate a biotin in the linker to immobilize the library in some circumstances. It also may be useful to incorporate a known ligand to one binding pocket of a target molecule as a means of performing selections for an encoded portion that can bind a second binding pocket of the same target molecule.

Example 12. Various Chemistries for Installing Building Blocks

Example 13. Synthesize an Encoded Portion Using Thioureation

A DNA library bearing an amine, either as a reactive site on a reaction site adapter, as a building block on a charged reaction site adapter or as a partially translated molecule, is dissolved in water at 1 mM. To it is added 20 equivalents 2-pyridylthionocarbonate as a 200 mM stock solution in dimethylacetamide at room temperature for 30 minutes. Then 40 equivalents of an amine are added as a 200 mM stock solution in dimethylacetamide at room temperature and slowly warmed to 60 μC and reacted for 18 hours. The product is purified by ethanol precipitation, or ion exchange chromatography. (See Deprez-Poulain, R. F., Charton, J., Leroux, V., and Deprez, B. P. (2007) Convenient synthesis of 4H-1,2,4-triazole-3-thiols using di-2-pyridylthionocarbonate. Tetrahedron Lett. 48, 8157-8162.)

Example 14. Synthesize an Encoded Portion Using Reductive Mono-Alkylation of an Amine A DNA library bearing an amine, either as a reactive site on a reaction site adapter, as a building block on a charged reaction site adapter or as a partially translated molecule, is dissolved in water at 1 mM. To it is added 40 equivalents of aldehyde as a 200 mM stock in dimethylacetamide, and reacted at room temperature for 1 hour. Then 40 equivalents of sodium borohydride are added as a 200 mM stock solution in acetonitrile and reacted at room temperature for 1 hour. The product is purified by ethanol precipitation, or ion exchange chromatography. (See Abdel-Magid, A. F., Carson, K. G., Harris, B. D., Maryanoff, C. A., and Shah, R. D. (1996) Reductive amination of aldehydes and ketones with sodium triacetoxyborohydride. J. Org. Chem. 61, 3849-3862.)

Example 15. Synthesize an Encoded Portion Using SNAr with Heteroaryl Compounds A DNA library bearing an amine, either as a reactive site on a reaction site adapter, as a building block on a charged reaction site adapter or as a partially translated molecule, is dissolved in water at 1 mM. To it is added 60 equivalents of a heteroarylhalide as a 200 mM stock solution in dimethylacetamide and reacted at 60° C. for 12 hours. The product is purified by ethanol precipitation, or ion exchange chromatography. (See Franch, T., Lundorf, M. D., Jacobsen, S. N., Olsen, E. K., Andersen, A. L., Holtmann, A., Hansen, A. H., Sorensen, A. M., Goldbech, A., De Leon, D., et al. Enzymatic encoding methods for efficient synthesis of large libraries. WIPO WO 2007/062664 A2, 2007.)

Example 16: Synthesize an Encoded Portion Using Horner-Wadsworth-Emmons Chemistry A DNA library bearing an aldehyde, either as a reactive site on a reaction site adapter, as a building block on a charged reaction site adapter or as a partially translated molecule, is dissolved in borate buffer pH 9.4 at 1 mM. To it is added 50 equivalents of ethyl 2-(diethoxyphsophoryl)acetate as a 200 mM stock in dimetylacetamide, and 50 equivalents of cesium carbonate as a 200 mM aqueous solution and reacted at room temperature for 16 hours. The product is purified by ethanol precipitation, or ion exchange chromatography. (See Manocci, L., Leimbacher, M., Wichert, M., Scheuermann, J., and Neri, D. (2011) 20 years of DNA-encoded chemical libraries. Chem. Commun. 47, 12747-12753.)

Example 17: Synthesize an Encoded Portion Using Sulfonylation

A DNA library bearing an amine, either as a reactive site on a reaction site adapter, as a building block on a charged reaction site adapter or as a partially translated molecule, is dissolved in borate buffer pH 9.4 at 1 mM. To it is added 40 equivalents of a sulfonyl chloride as a 200 mM stock solution in dimethylacetamide and reacted at room temp for 16 hours. The product is purified by ethanol precipitation, or ion exchange chromatography. (See Franch, T., Lundorf, M. D., Jacobsen, S. N., Olsen, E. K., Andersen, A. L., Holtmann, A., Hansen, A. H., Sorensen, A. M., Goldbech, A., De Leon, D., et al. Enzymatic encoding methods for efficient synthesis of large libraries. WIPO WO 2007/062664 A2, 2007.)

Example 18: Synthesize an Encoded Portion Using Trichloro-Nitro-Pyrimidine

A DNA library bearing an amine, either as a reactive site on a reaction site adapter, as a building block on a charged reaction site adapter or as a partially translated molecule, is dissolved in borate buffer pH 9.4 at 1 mM. To it is added 20 equivalents of trichloro-nitro-pyrimidine (TCNP) as a 200 mM stock solution in dimethylacetamide at 5° C. The reaction is warmed to room temp over an hour and purified by ethanol precipitation. The DNA library is dissolved at 1 mM in borate buffer pH 9.4 and 40 equivalents of amine are added as a 200 mM stock solution in dimethylacetamide, 100 equivalents of neat triethylamine and reacted at room temp for 2 hours. The library is purified by ethanol precipitation. The DNA library is either immediately dissolved in borate buffer for immediate reaction, or it is pooled, re-sorted on an array and then dissolved in borate buffer, whereupon it is reacted with 50 equivalents of an amine as a 200 mM stock in dimtheylacetamide and 100 equivalents of triethylamine and reacted at room temperature for 24 hours. The product is purified by ethanol precipitation, or ion exchange chromatography. (See Roughley, S. D., and Jordan, A. M. (2011) The medicinal chemist's toolbox: an analysis of reactions used in the pursuit of drug candidates. J. Med. Chem. 54, 3451-3479.)

Example 19: Synthesize an Encoded Portion Using Trichloropyrimidine

A DNA library bearing an amine, either as a reactive site on a reaction site adapter, as a building block on a charged reaction site adapter or as a partially translated molecule, is dissolved in borate buffer pH 9.4 at 1 mM. To it is added 50 equivalents of 2,4,6 trichloropyrimidine as a 200 mM stock in DMA and reacted at room temp for 3.5 hours. The DNA is precipitated in ethanol, and then re-dissolved in borate buffer pH 9.4 at 1 mM. To it is added 40 equivalents of amine as a 200 mM acetonitrile stock and reacted at 60-80° C. for 16 hrs. The product is purified by ethanol precipitation and then the DNA library is either immediately dissolved in borate buffer for immediate reaction, or it is pooled, re-sorted on an array and then dissolved in borate buffer, whereupon it is reacted with 60 equivalents of a boronic acid as a 200 mM stock in dimethylacetamide (DMA) and 200 equivalents of sodium hydroxide as a 500 mM aqueous solution, 2 equivalents of palladium acetate as a 10 mM DMA stock and 20 equivalents of tris(3-sulfophenyl)phosphine trisodium salt (TPPTS) as a 100 mM aqueous solution, and reacted at 75° C. for 3 hours. The DNA is precipitated in ethanol, then dissolved in water at 1 mM and reacted with 120 equivalents of sodium sulfide as a 400 mM stock in water at 65° C. for 1 hour. The product is purified by ethanol precipitation, or ion exchange chromatography.

Example 20: Synthesize an Encoded Portion Using Boc-Deprotection

A DNA library bearing a Boc-protected amine, as a reactive site on a reaction site adapter, as a building block on a charged reaction site adapter, or as a partially translated molecule, is dissolved in borate buffer pH 9.4 at 0.5 mM, and heated to 90° C. for 16 hours. The product is purified by ethanol precipitation, size exclusion chromatography or ion exchange chromatography. (See Franch, T., Lundorf, M. D., Jacobsen, S. N., Olsen, E. K., Andersen, A. L., Holtmann, A., Hansen, A. H., Sorensen, A. M., Goldbech, A., De Leon, D., et al. Enzymatic encoding methods for efficient synthesis of large libraries. WIPO WO 2007/062664 A2, 2007.)

Example 21: Synthesize an Encoded Portion Using Hydrolysis of a t-butyl ester A DNA library bearing t-butyl ester, as a reactive site on a reaction site adapter, as a building block on a charged reaction site adapter, or as a partially translated molecule, is dissolved in borate buffer at 1 mM, and reacted at 80° C. for 2 hours. The product is purified by ethanol precipitation, size exclusion chromatography or ion exchange chromatography. (See Franch, T., Lundorf, M. D., Jacobsen, S. N., Olsen, E. K., Andersen, A. L., Holtmann, A., Hansen, A. H., Sorensen, A. M., Goldbech, A., De Leon, D., et al. Enzymatic encoding methods for efficient synthesis of large libraries. WIPO WO 2007/062664 A2, 2007.)

Example 22: Synthesize an Encoded Portion Using Alloc-Deprotection

A DNA library bearing an Alloc-protected amine, as a reactive site on a reaction site adapter, as a building block on a charged reaction site adapter or as a partially translated molecule, is dissolved in borate buffer pH 9.4 at 1 mM. To it is added 10 equiv. of palladium tetrakis triphenylphosphine as a 10 mM DMA stock, and 10 equiv. of sodium borohydride as a 200 mM acetonitrile stock and reacted at room temperature for 2 hours. The product is purified by ethanol precipitation, or ion exchange chromatography. (See Beugelmans, R., Neuville, M. B.-C., Chastanet, J., and Zhu, J. (1995) PalladiµM catalyzed reductive deprotection of Alloc: Transprotection and peptide bond formation. Tetrahedron Lett. 36, 3129.)

Example 23: Synthesize an Encoded Portion Using Hydrolysis of a Methyl/Ethyl Ester A DNA library bearing methyl or ethyl ester, as a reactive site on a reaction site adapter, as a building block on a charged reaction site adapter, or as a partially translated molecule, is dissolved in borate buffer at 1 mM, and reacted with 100 equiv of NaOH at 60° C. for 2 hours. The product is purified by ethanol precipitation, size exclusion chromatography or ion exchange chromatography. (See Franch, T., Lundorf, M. D., Jacobsen, S. N., Olsen, E. K., Andersen, A. L., Holtmann, A., Hansen, A. H., Sorensen, A. M., Goldbech, A., De Leon, D., et al. Enzymatic encoding methods for efficient synthesis of large libraries. WIPO WO 2007/062664 A2, 2007.)

Example 24: Synthesize an Encoded Portion Using Reduction of a Nitro Group

A DNA library bearing a nitro group, as a reactive site on a reaction site adapter, as a building block on a charged reaction site adapter, or as a partially translated molecule, is dissolved in water at 1 mM. To it is added 10% volume equiv. of Raney nickel slurry, 10% volume equiv. of hydrazine as a 400 mM aqueous solution and reacted at room temp for 2-24 hrs with shaking. The product is purified by ethanol precipitation, or ion exchange chromatography. (See Balcom, D., and Furst, A. (1953) Reductions with hydrazine hydrate catalyzed by Raney nickel. J. Am. Chem. Soc. 76, 4334-4334.)

Example 25: Synthesize an Encoded Portion Using "Click" Chemistry

A DNA library bearing an alkyne or an azide group, as a reactive site on a reaction site adapter, as a building block on a charged reaction site adapter or as a partially translated molecule, is dissolved in 100 mM phosphate buffer at 1 mM. To it is added copper sulfate to 625 µM, THPTA (ligand) to 3.1 mM, amino-guanidine to 12.5 mM, ascorbate to 12.5 mM, and an azide to 1 mM (if the DNA bears an alkyne) or an alkyne to 1 mM (if the DNA bears an azide). The reaction is run at room temperature for 4 hours. The product is purified by ethanol precipitation, size exclusion chromatography or ion exchange chromatography. (See Hong, V., Presolski, Stanislav I., Ma, C. and Finn, M. G. (2009), Analysis and Optimization of Copper-Catalyzed Azide-Alkyne Cycloaddition for Bioconjugation. Angewandte Chemie International Edition, 48: 9879-9883.)

Example 26: Synthesize an Encoded Portion Incorporating a Benzimidazole

A DNA library bearing an aryl vicinal diamine, as a reactive site on a reaction site adapter, as a building block on a charged reaction site adapter or as a partially translated molecule, is dissolved in borate buffer pH 9.4 at 1 mM. To it is added 60 equiv. of an aldehyde as a 200 mM DMA stock and reacted at 60° C. for 18 hours. The product is purified by ethanol precipitation, or ion exchange chromatography. (See (1) Mandal, P., Berger, S. B., Pillay, S., Moriwaki, K., Huang, C., Guo, H., Lich, J. D., Finger, J., Kasparcova, V., Votta, B., et al. (2014) RIP3 induces apoptosis independent of pronecrotic kinase activity. Mol. Cell 56, 481-495; (2) Gouliaev, A. H., Franch, T. P.-O., Godskesen, M. A., and Jensen, K. B. (2012) Bi-functional Complexes and methods for making and using such complexes. Patent Application WO 2011/127933 A1; (3) Mukhopadhyay, C., and Tapaswi, P. K. (2008) Dowex 50W: A highly efficient and recyclable green catalyst for the construction of the 2-substituted benzimidazole moiety in aqueous medium. Catal. Commun. 9, 2392-2394.)

Example 27: Synthesize an Encoded Portion Incorporating an Imidazolidinone

A DNA library bearing an alpha-amino-amide, either as a reactive site on a reaction site adapter, as a building block on a charged reaction site adapter or as a partially translated molecule, is dissolved in 1:3 methanol:borate buffer pH 9.4 at 1 mM. To it is added 60 equiv. of an aldehyde as a 200 mM DMA stock and reacted at 60° C. for 18 hours. The product is purified by ethanol precipitation, or ion exchange chromatography. (See (1) Barrow, J. C., Rittle, K. E., Ngo, P. L., Selnick, H. G., Graham, S. L., Pitzenberger, S. M., McGaughey, G. B., Colussi, D., Lai, M.-T., Huang, Q., et al. (2007) Design and synthesis of 2,3,5-substituted imidazolidin-4-one inhibitors of BACE-1. Chem. Med. Chem. 2, 995-999; (2) Wang, X.-J., Frutos, R. P., Zhang, L., Sun, X., Xu, Y., Wirth, T., Nicola, T., Nummy, L. J., Krishnamurthy, D., Busacca, C. A., Yee, N., and Senanayake, C. H. (2011) Asymmetric synthesis of LFA-1 inhibitor BIRT2584 on metric ton scale. Org. Process Res. Dev. 15, 1185-1191; (3) Blass, B. E., Janusz, J. M., Wu, S., Ridgeway, J. M. II, Coburn, K., Lee, W., Fluxe, A. J., White, R. E., Jackson, C. M., and Fairweather, N. 4-Imidazolidinones as KV1.5 Potassium channel inhibitors. WIPO WO2009/079624 A1, 2009.)

Example 28: Synthesize an Encoded Portion Incorporating a Quinazolinone

A DNA library bearing an 2-anilino-1-benzamide, either as a reactive site on a reaction site adapter, as a building block on a charged reaction site adapter or as a partially translated molecule, is dissolved in borate buffer pH 9.4 at 1 mM. To it is added 200 equiv. NaOH as a 1M solution in water and an aldehyde as a 200 mM stock solution in DMA and reacted at 90° C. for 14 hours. The product is purified by ethanol precipitation, or ion exchange chromatography. (See Witt, A., and Bergmann, J. (2000) Synthesis and reactions of some 2-vinyl-3H-quinazolin-4-ones. Tetrahedron 56, 7245-7253.)

Example 29: Synthesize an Encoded Portion Incorporating an Isoindolinone

A DNA library bearing an amine, either as a reactive site on a reaction site adapter, as a building block on a charged reaction site adapter or as a partially translated molecule, is dissolved in borate buffer pH 9.4 at 1 mM. To it is added a 4-bromo, 2-ene methyl ester as a 200 mM stock solution in DMA and reacted for 2 hours at 60° C. The product is purified by ethanol precipitation, or ion exchange chromatography. (See Chauleta, C., Croixa, C., Alagillea, D., Normand, S., Delwailb, A., Favotb, L., Lecronb, J.-C., and Viaud-Massuarda, M. C. (2011) Design, synthesis and biological evaluation of new thalidomide analogues as TNF-α and IL-6 production inhibitors. Bioorg. Med. Chem. Lett. 21, 1019-1022.)

Example 30: Synthesize an Encoded Portion Incorporating a Thiazole

A DNA library bearing a thiourea, either as a reactive site on a reaction site adapter, as a building block on a charged reaction site adapter or as a partially translated molecule, is dissolved in borate buffer pH 9.4 at 1 mM. To this is added 50 equiv. of a bromoketone as a 200 mM stock in DMA and reacted at room temp for 24 hours. The product is purified by ethanol precipitation, or ion exchange chromatography. (See Potewar, T. M., Ingale, S. A., and Srinivasan, K. V. (2008) Catalyst-free efficient synthesis of 2-aminothiazoles in water at ambient temperature. Tetrahedron 64, 5019-5022.)

Example 31: Synthesize an Encoded Portion Incorporating an Imidazopyridine

A DNA library bearing an aryl aldehyde, either as a reactive site on a reaction site adapter, as a building block on a charged reaction site adapter or as a partially translated molecule, is dissolved in borate buffer pH 9.4 at 1 mM. To it is added 50 equivalents of a 2-amino pyridine as a 200 mM stock solution in DMA, and 2500 equiv. of NaCN as a 1M aqueous solution and reacted at 90° C. for 10 hours. The product is purified by ethanol precipitation, or ion exchange chromatography. (See (1) Alexander Lee Satz, Jianping Cai, Yi Chen, Robert Goodnow, Felix Gruber, Agnieszka Kowalczyk, Ann Petersen, Goli Naderi-Oboodi, Lucja Orzechowski, and Quentin Strebel. DNA Compatible Multistep Synthesis and Applications to DNA Encoded Libraries Bioconjugate Chemistry 2015 26 (8), 1623-1632; (2) Beatch, G. N., Liu, Y., and Plouvier, B. M. C. PCT Int. Appl. 2001096335, Dec. 20, 2001; (3) Inglis, S. R., Jones, R. K., Booker, G. W., and Pyke, S. M. (2006) Synthesis of N-benzylated-2-aminoquinolines as ligands for the Tec SH3 domain. Bioorg. Med. Chem. Lett. 16, 387-390.)

Example 32: Synthesize an Encoded Portion Using Suzuki Coupling Chemistry

A DNA library bearing an aryl-iodide, either as a reactive site on a reaction site adapter, as a building block on a charged reaction site adapter or as a partially translated molecule, is dissolved in water at 1 mM. To it is added 50 equivalents of a boronic acid as a 200 mM stock solution in dimethylacetamide, 300 equivalents of sodium carbonate as a 200 mM aqueous solution, 0.8 equivalents of palladium acetate as a 10 mM stock solution in dimethylacetamide premixed with 20 equivalents of 3,3',3" phosphanetriyltris (benzenesulfonic acid) trisodium salt as a 100 mM aqueous solution. The mixture is reacted at 65° C. for 1 hour then purified by ethanol precipitation. The DNA library is dissolved in buffer to 1 mM and 120 equivalents of sodium sulfide as a 400 mM aqueous solution is added, then reacted at 65° C. for 1 hour. The product is diluted to 200 µl with dH$_2$O and purified by ion exchange chromatography. (See Gouliaev, A. H., Franch, T. P. O., Godskesen, M. A., and Jensen, K. B. (2012) Bi-functional Complexes and methods for making and using such complexes. Patent Application WO 2011/127933 A1.)

Example 33: Synthesize an Encoded Portion Using Sonogashira Coupling Chemistry A DNA library bearing an aryl-iodide, either as a reactive site on a reaction site adapter, as a building block on a charged reaction site adapter or as a partially translated molecule, is dissolved in water at 1 mM. To it is added 100 equivalents of an alkyne as a 200 mM stock solution in dimethylacetamide, 300 equivalents of pyrrolidine as a 200 mM stock solution in dimethylacetamide, 0.4 equivalents of palladium acetate as a 10 mM stock solution in dimethylacetamide, 2 equivalents of 3, 3',3" phosphanetriyltris (benzenesulfonic acid) trisodium salt as a 100 mM aqueous solution. The reaction is run for 2 hours at 65° C., then purified by ethanol precipitation or by ion exchange chromatography. (See (1) Liang, B., Dai, M., Chen, J., and Yang, Z. (2005) Cooper-free sonogashira coupling reaction with PdCl2 in water under aerobic conditions. J. Org. Chem. 70, 391-393; (2) Li, N., Lim, R. K. V., Edwardraja, S., and Lin, Q. (2011) Copper-free Sonogashira cross-coupling for functionalization of alkyne encoded proteins in aqueous medium and in bacterial cells. J. Am. Chem. Soc. 133, 15316-15319; (3) Marziale, A. N., Schluter, J., and Eppinger, J. (2011) An efficient protocol for copper-free palladium-catalyzed Sonogashira crosscoupling in aqueous media at low temperatures. Tetrahedron Lett. 52, 6355-6358; (4) Kanan, M. W., Rozenman, M. M., Sakurai, K., Snyder, T. M., and Liu, D. R. (2004) Reaction discovery enabled by DNA-templated synthesis and in vitro selection. Nature 431, 545-549.)

Example 34: Synthesize an Encoded Portion Using Carbamylation

A DNA library bearing an amine, either as a reactive site on a reaction site adapter, as a building block on a charged reaction site adapter or as a partially translated molecule, is dissolved in water at 1 mM. To it is added 1:4 v/v triethylamine, 50 equivalents of di-2-pyridylcarbonate as a 200 mM stock solution in dimethylacetamide. The reaction is run for 2 hours at room temp, then 40 equivalents of an amine as a 200 mM stock solution in dimethylacetamide is added at room temperature for 2 hours. The product is purified by ethanol precipitation, or ion exchange chromatography. (See (1) Artuso, E., Degani, I., and Fochi, R. (2007) Preparation of mono-, di-, and trisubstituted ureas by carbonylation of aliphatic amines with S,S-dimethyl dithiocarbonate. Synthesis 22, 3497-3506; (2) Franch, T., Lundorf, M. D., Jacobsen, S. N., Olsen, E. K., Andersen, A. L., Holtmann, A., Hansen, A. H., Sorensen, A. M., Goldbech, A., De Leon, D., et al. Enzymatic encoding methods for efficient synthesis of large libraries. WIPO WO 2007/062664 A2, 2007.)

Example 35: Synthesize an Encoded Portion Using Various Other Chemistries

Thirty-one types of compatible chemical reactions are listed with references in Handbook for DNA-Encoded Chemistry (Goodnow R. A., Jr., Ed.) pp 319-347, 2014 Wiley, New York. These include SNAr reactions of trichlorotriazines, diol oxidations to glyoxal compounds, Msec deprotection, Ns deprotection, Nvoc deprotection, pentenoyl deprotection, indole-styrene coupling, Diels-Alder reaction, Wittig reaction, Michael addition, Heck reaction, Henry reaction, nitrone 1,3-dipolar cycloaddition with activated alkenes, formation of oxazolidines, trifluoroacetamide deprotection, alkene-alkyne oxidative coupling, ring-closing metatheses and aldol reactions. Other reactions are published in this reference that have the potential of working in the presence of DNA and are appropriate for use.

Example 36: Use Different Restriction Enzymes in Library Preparation

It will be understood that the restriction enzymes named in other Examples are representative, and that other restriction enzymes may serve the same purpose with equanimity or advantage.

Example 37a: Perform a Gene-Shuffling or Crossing-Over Reaction on a Library, Case 1

After a library like the one described in Examples above is translated and selected, performing a gene-shuffling will produce new offspring phenotypes not previously extant in the library, or produce offspring phenotypes that re-sample phenotypes surviving selection. This is accomplished by selective use of the protocols described in Example 1b and 1c, or in Example 2a and 2b. In a first case where all possible recombinations are desired, the post selection DNAs are amplified, and split into 2 aliquots. The first aliquot represents a sample that is phenotypically enriched by selection, and is set aside for use without recombination/shuffling. The second aliquot is restriction digested to de-couple all codons from each other as in Example 1b, and the codons are combinatorially re-assorted to produce a fully recombined gene library as in Example 1c. The digestion/re-ligation products are pooled, purified and amplified, added to the phenotypically enriched aliquot and subsequent rounds of library preparation, translation and selection is done as per Examples above.

Example 37b: Perform a Gene-Shuffling or Crossing-Over Reaction on a Library, Case 2

In a second case where more selective recombination is desired, the post-selection DNAs are amplified and split into several aliquots. One aliquot is set aside as in Case 1. Each of the other aliquots are subjected to selective restriction digestion and re-ligation as described in Example 2b.

Example 38: Index Molecules of Formula (I)

A coding region is set aside or added for use as an indexing region in G. After preparation and translation of a library as per Example 1, the library is sorted on a hybridization array by a coding region set aside for indexing. The subpools generated by such sorting are used for different purposes, are selected for different properties, for different targets, or for the same target under different conditions. The products of the different selections are optionally amplified by PCR independently, re-pooled with the other subpools, and re-translated as in Examples above.

Example 39. The Absence of a Building Block is an Encodable Diversity Element

In the course of library synthesis, diversity is generated when a multiplicity of building blocks are installed independently on various library subpools possessing different sequences. The absence of a building block is an optional diversity element. The absence of a building block is encoded exactly as per Examples above, except that at a desired chemical step, one or more sequence-specific subpools of the library are not treated with any chemistry to install a building block. In such case the sequence of those subpools thereby encode the absence of a building block.

Example 40. Hybridization Arrays Comprised of Other Materials

Hybridization Arrays can accomplish 2 critical tasks: (a) they can sort a heterogeneous mixture of at least partially single-stranded DNAs through sequence specific hybridization, and (b) the arrays can enable or allow the sorted sub-pools to be removed from the array independently. The features of the array wherein anti-coding oligonucleotides are immobilized may be arranged in any three dimensional orientation that meets the above criteria, but a 2 dimensional rectangular grid array is currently most attractive because an abundance of commercially available labware is already mass produced in that format (e.g. 96-well plates, 384-well plates).

The solid supports in the features of the array upon which anti-coding oligos are immobilized can accomplish 4 tasks: (a) it can permanently affix the anti-coding oligo, (b) it can enable or allow capture of a library DNA through sequence specific hybridization to the immobilized oligo, (c) it can have low background or non-specific binding of library DNA, and (d) it can be chemically stable to the processing conditions, including a step performed at high pH. CM SEPHAROSE® has been functionalized with azido-PEG-amine (with 9 PEG units) by peptide bond formation between the amine of azido-PEG-amine and carboxyl groups on the surface of the CM SEPHAROSE® resin. Anti-coding oligos bearing an alkynyl-modifier are 'clicked' to the azide in a copper-mediated 1,3-dipolar cycloaddition (Huisgen).

Other suitable solid supports include hydrophilic beads, or polystyrene beads with hydrophilic surface coatings, polymethylmethacrylate beads with hydrophilic surface coatings, and other beads with hydrophilic surfaces which also bear a reactive functional group like a carboxylate, amine, or epoxide, to which an appropriately functionalized anti-coding oligo is immobilized. Other suitable supports include monoliths and hydrogels. See, for example, J Chromatogr A. 2002 Jun. 14; 959(1-2):121-9, J Chromatogr A. 2011 Apr. 29; 1218 (17): 2362-7, J Chromatogr A. 2011 Dec. 9; 1218(49):8897-902, Trends in Microbiology, Volume 16, Issue 11, 543-551, J. Polym. Sci. A Polym. Chem., 35: 1013-1021, J. Mol. Recognit. 2006; 19: 305-312, J. Sep. Sci. 2004, 27, 828-836. Generally, solid supports with greater surface area capture a greater amount of library DNA, and beads with smaller diameter engender far higher back pressures and resistance to flow. These constraints are in part improved by the use of porous supports or hydrogels, which have very high surface areas, but lower backpressures. Generally, beads with positive charges engender greater degrees of non-specific binding of DNA.

The chassis of the hybridization array can accomplish 3 tasks: (a) it can maintain the physical separation between features, (b) enable or allow a library to flow over or through the features, and (c) enable or allow removal of the sorted library DNA from different features independently. The chassis is comprised of any material that is sufficiently rigid, chemically stable under processing conditions, and compatible with any means that are required for immobilizing supports within features. Typical materials for the chassis include plastics like DELRIN®, TECAFROM®, or polyether ether ketone (PEEK), ceramics, and metals, like aluminum or stainless steel.

Example 41. Measurement of Yields of Chemical Reactions

As an example of measuring yields of chemical reactions using this method, an experiment was performed to discern between ssDNA library strands bearing one reactive moiety, and ssDNA library strands bearing another. This model serves to illustrate the case where some ssDNA library members bearing a downstream reactive handle have been successfully reacted with building blocks bearing a different downstream handle. Six ssDNA library templates, representing molecules of formula (II), were prepared. Five of them, library members A-E, bore an alkyne moiety linked to the template 3' end (to model a BK building block) and comprised a 'positive control set' exemplifying reactions with building blocks in which a downstream alkynyl handle was successfully installed. One, library member F, was modified by an amine moiety linked to the template 3' end (to model a BK-1 building block) and comprised the 'negative control' exemplifying a reaction where a building block bearing the alkynyl moiety was not successfully coupled. Library members A through F were combined in a serial dilution to model reactions giving different yields. In total, there were 54 pmol of templates A-F in 452 ul of 100 mM potassium phosphate, pH 7.5, giving a concentration of total template of 0.12 uM. In this example, sequence T was the final set of base at the 3' end of G and had the sequence, TTTC-CACGCTAGTATGCACG. A sample of this pre-processing mixture was collected and set aside for sequencing.

One mole-equivalent, 54 pmol, of a "live bait" molecule of formula (III) was added to the mixture of A-F. This exemplary molecule comprised a sequence U complementary to the Sequence T in molecules A-F. Sequence U in the molecule of formula (III) was allowed to anneal to sequence T in the molecules of formula (II). In this example, U had the sequence CGTGCATACTAGCGTGGAAA, and bore an azide linked to its 5'end.

After annealing the "live bait" molecule of formula (III) to library members A-F, a click reaction was performed by adding 145 ul of a solution containing 10 mM $CuSO_4$, 100 mM amino-guanine, 50 mM THPTA (Tris(3-hydroxypropyl triazolylmethyl)amine), and 100 mM freshly prepared sodium ascorbate (based on a method of Finn, in Angew. Chem. Int. Ed. 2009, 48, 9879-9883). The reaction was run for 15 minutes at room temperature.

The crude reaction product was desalted to remove the copper catalyst by passing over a SEPHADEX® G25 column that had been pre-washed with 1× first strand synthesis buffer.

The reaction was then diluted 100-fold from 0.12 uM to 1.2 nM with first strand synthesis buffer. Whereupon a "dead bait" oligo was added to a concentration of 120 nM, the solution was warmed to 75° C. in a heat block then removed and allowed to cool to room temp. During this annealing phase, the 'dead bait' competed to anneal to templates with any "live bait" left over, and with any 'live bait' which was covalently linked to a template to form molecules of formula (I). The "dead bait" sequence in this example was CGTG-CATACTAGCGTGGAAddC, in which the 3' terminal base was a dideoxyC, a base commonly used to halt 5' to 3' extension.

The solution was subjected to first-strand synthesis conditions using MMLV (Moloney Murine Leukemia Virus) reverse transcriptase from NEB, the reaction solution was adjusted to closely match the manufacturer's protocols; the reaction was executed at 42° C. for 1 hour. This reaction allowed all templates primed with "live bait" to be extended by the MMLV and made double-stranded, whereas all templates primed with the "dead bait" would remain single-stranded.

Directly to the MMLV reaction was added 1×NEB buffer 2, and the exonuclease $Rec_{Jf}$. This exonuclease operates in the 5' to 3' direction and digests only single-stranded DNA. The reaction was conducted at 37° C. for 30 minutes.

The ILLUMINA® sequencing primers were installed by extension PCR to both the pre-processing sample mix of templates A-F and the post-processing sample. See FIG. 6 for a summary of the sequencing data.

Figure 6:
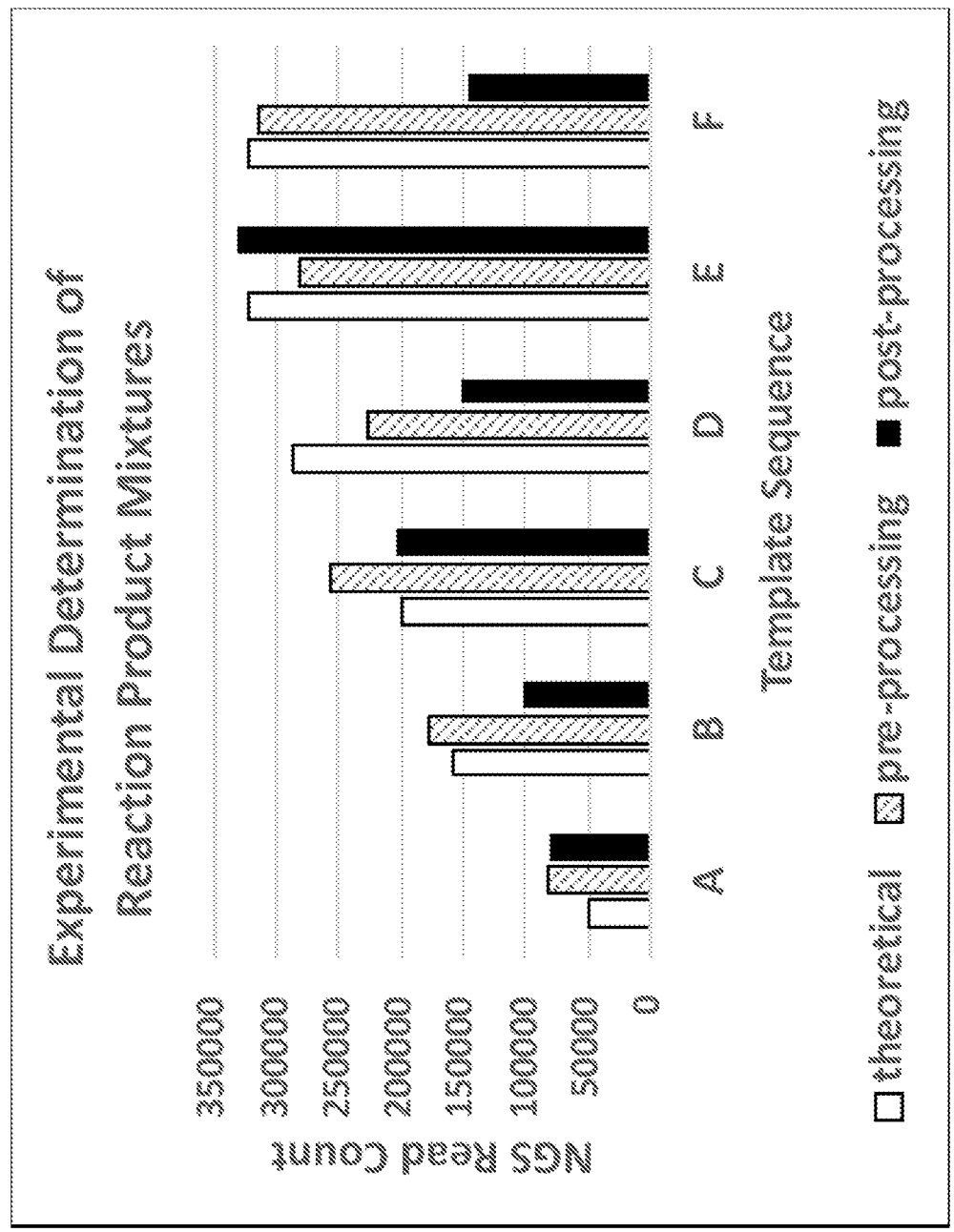
FIG. 6 is a graph of relative abundance of molecules as measured by fluorescent spectroscopy for template sequences A-F.

Referring to FIG. 6, the white bars represent the A260 sample mixture which was made in the lab using measurements of DNA concentration by absorbance at 260 nm. Hashed bars represent the pre-processing sample, and black bars represent the post-processing sample. White bars show an estimation of how many reads one could expect from NGS based on calculations derived from the ratio of the amounts of template A-F observed by A260 and the total number of reads from the pre-processing sample. The hashed bars represent the pre-processing sample as directly measured by NGS. In theory, the pre-processing (hashed bar) relative ratios should be the same as the A260 (white bar) relative ratios, since they are the SAME sample. The white bars also reflect the ratio of templates observed by A260, AND the total length of all white bars equals the total length of all hashed bars—since they are the same sample. That is, the total number of A260 read counts was calculated to be the same as the pre-processing total read count as measured by NGS. The post-processing sample black bars represent reads of a sample that had undergone significant processing, including a step designed to diminish the number of F templates. Therefore, the read counts for this sample could not be normalized to the total number of reads in the pre-processing sample. But because the ratio of A-E reads to each other should not have changed during processing, the post-processing read counts were normalized to the read count of the positive control A template.

This experiment demonstrates the feasibility of determining product distributions and reaction yields using NGS. Both positive control compounds representing examples of successful incorporation of a building block, and negative control compounds representing unsuccessful attempts at incorporation of a building block were present in the same mixture, just as they would be during library synthesis. Further, the positive control compounds were protected from digestion by reaction between a molecule of formula (II) and molecule of formula (III) to produce a molecule of formula (I), whereas negative molecules were not. Both positive and negative controls were processed in exactly the same way, and then measured simultaneously. During synthesis of a library, many hundreds or thousands of reactions are performed to produce millions to billions of compounds, and chemical reaction yields can easily range from near 100% to below 1%; this is a span of greater than 100-fold between reacted and unreacted library materials. Heretofore there has not existed a technique for making a direct measurement of the chemical yield of so vast a number of chemical reactions. This technique works by maintaining the relative ratios of a mixture of positive DNA sequences through several enzymatic steps of processing and by diminishing or abolishing the number of negative DNA sequences. In this experiment, one sees the ratio of positive sequences observed pre-processing, and post-processing, is similar to that observed by A260. Variation between the pre-preprocessing sample and the post-processing sample does not exceed the variation between the pre-processing sample and the A260 sample. One also sees a marked diminishment of the negative control signal, and greater diminishment engenders greater accuracy.

Control experiments mimicking the above protocol were also conducted, but the positive templates annealed to "live bait" molecules of formula (III) were kept separate from negative templates annealed to "dead bait" so that they could be run on a gel side by side for analysis. See FIG. 7.

Figure 7:
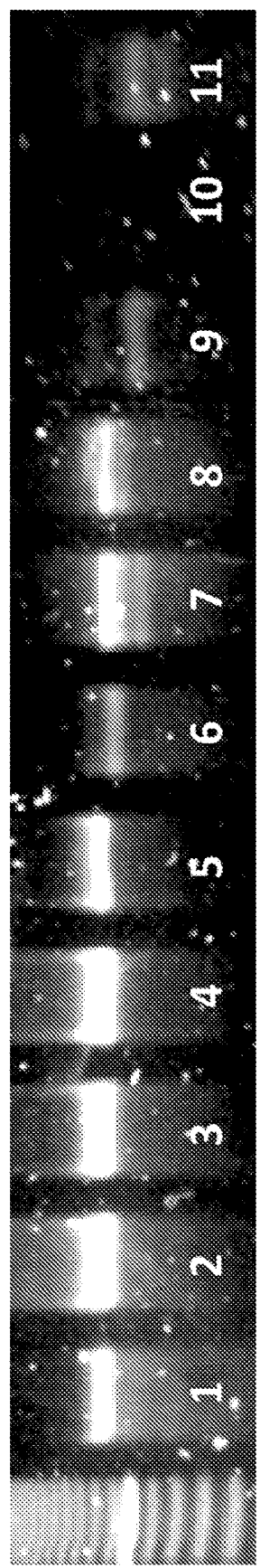
FIG. 7 is a picture of fluorescent observation of double and/or single stranded DNA during electrophoretic studies of template sequences.

Referring to FIG. 7,
Lane 1 dsDNA template.
Lane 2 ssDNA template was annealed to "live bait" molecules of formula (III), and treated with Bst 2.0 polymerase The product is dsDNA.
Lane 3 repeat of Lane 2, but further treated with Recf exonuclease. No digestion by Recf of ds DNA is observed. (Recf is a single-stranded DNA specific exonuclease that catalyzes the removal of deoxy-nucleotide monophosphates from DNA in the 5'→3' direction (1). $Rec_{Jf}$ is a recombinant fusion protein of RecJ and maltose binding protein (MBP).)
Lane 4 sDNA template annealed to "live bait" molecules of formula (III), and treated with MMLV-Reverse Transcriptase. The product is dsDNA.
Lane 5 repeat of Lane 4, but further treated with Recf exonuclease. No digestion by RecJf of ds DNA is observed.
Lane 6 ssDNA template annealed to "dead bait" oligos bearing the same sequence as the "live bait" molecules of formula (III), but having a 3' terminal dideoxyC base intended to abolish 5' to 3' extension. (Note this ssDNA is also annealed to a fluorescently-labeled primer which improves visualization on the gel, but causes a slight shift in mobility)
Lane 7. ssDNA template annealed to dead bait and treated with BST 2.0. This polymerase appears to extend the template, diminishing its utility in this application. Some uncopied ssDNA appears to still be present in the sample.
Lane 8 repeat of Lane 7, but further treated with Recf exonuclease. The ssDNA is digested, but the dsDNA remains.
Lane 9 ssDNA template annealed to dead bait and treated with MMLV. No extension of the primer or dsDNA product is observed.
Lane 10 repeat of Lane 9, but with further treatment by Recf exonuclease. ssDNA is digested.
Lane 11 ssDNA template annealed to a fluorescently labeled primer analog to the bait molecules The gel was run in 3% agarose in TBE buffer at 150V.

This experiment clearly demonstrates the feasibility of making a ssDNA template into a dsDNA template when it is annealed to a "live bait" primer molecule of formula (III) that is extended by MMLV-RT. It also demonstrates that the same ssDNA will not be made double-stranded by MMLV-RT if it is primed with a "dead bait" primer bearing a 3' dideoxy C. Further, this experiment shows that $Rec_{Jf}$ exonuclease will digest single-stranded DNA. But will not digest double-stranded DNA.

Importantly, this experiment shows that when two ssDNAa are primed, treated with a polymerase, like MMLV-RT, and further treated with an ssDNA exonuclease, like $Rec_{Jf}$, that the ssDNAs primed with a "dead" primer (one bearing a moiety that retards or abolishes primer extension by the polymerase) will not be extended by the polymerase and will be digested by the exonuclease. It shows when the ssDNA is primed by a primer allowing extension, then being made double-stranded will protect it from digestion by the exonuclease.

This data proves in principle that the enzymatic tools exists for the disclosed invention. The invention calls for a means to selectively preserve (or digest as needed) certain DNAs. In this instance, using different primers rendered ssDNA protectable, or digestible, as needed.

What is claimed is:

1. A method of assessing synthetic yield of a reaction step that adds a free positional building block unit B to a molecule of formula (IV), the method comprising:
   providing a pool of molecules of formula (IV), $$G\text{-}L\text{-}(B)_{(K-1)} \qquad (IV);$$

amplifying G within formula (IV) from a first portion of the pool of molecules of formula (IV) by polymerase chain reaction (PCR) to form a pool of pre-reaction copies of G;
   reacting the molecule of formula (IV) in a second portion of the pool of molecules of formula (IV) with the free positional building block unit B and a molecule of formula (III), $$Q\text{-}U \qquad (III),$$

to form a pool of verification molecules of formula (I), $$G\text{-}L\text{-}(B)_K\text{-}Q\text{-}U \qquad (I);$$

wherein
   G is an oligonucleotide, the oligonucleotide comprising at least two coding regions, wherein the at least two coding regions are single stranded;
   L is a linker that operatively links G to $(B)_K$ or $(B)_{(K-1)}$;
   $(B)_K$ and $(B)_{(K-1)}$ represent a series of individual positional building block units B bound together to form a polymer chain having K number of positional units, and K represents an integer from 1 to about 20;
   Q is a non-positional building block directly attached to the positional building block B at the terminal position K; and
   (i) G contains T, wherein:
      T is an attachment oligonucleotide that is positioned from 0 to about 120 bases from a 3' end of G,
      the 3' end of G is the base that is directly attached to L,
      T is at least partially single stranded,
      U is an oligonucleotide that is capable of hybridizing to T, and
      U hybridizing to T forms a loop structure, wherein subsequent polymerase chain reaction selectively amplifies molecules of formula (I) comprising said loop structure but does not amplify molecules of formula (IV) lacking said loop structure, or (ii) U is an affinity chromatography agent;

wherein each positional building block B at position K in the series of $(B)_K$ is identified by and corresponds to one of the coding regions in G;

(a) provided that U is an oligonucleotide that is capable of hybridizing to T, removing unreacted molecules of formula (IV) from the pool of verification molecules of formula (I) by annealing the oligonucleotide U to T, when G contains T, to form the loop structure, performing PCR to form a double stranded pool of verification molecules of formula (I), wherein G is double stranded, and adding a selection agent to the double stranded pool of verification molecules of formula (I), or (b) provided that U is an affinity chromatography agent, removing unreacted molecules of formula (IV) from the pool of verification molecules of formula (I) by a method selected from the group consisting of affinity chromatography, immobilized metal ion chromatography, metal chelation chromatography, size exclusion chromatography, normal phase chromatography, reverse phase chromatography, and a combination thereof;

amplifying at least one oligonucleotide G from the pool of verification molecules of formula (I) to form a pool of post-reaction copies of G; and assessing synthetic yield of the reaction step that adds the free positional building block unit B to the molecule of formula (IV) in the pool of molecules of formula (IV) by comparing the pool of pre-reaction copies of G and the pool of post-reaction copies of G, wherein the synthetic yield is based on the ratio of the number of copies of G in the pool of post-reaction copies of G to the pool of pre-reaction copies of G.

2. The method of claim 1, further comprising:

sequencing at least one of the pool of pre-reaction copies of G and the pool of post-reaction copies of G.

3. The method of claim 2, further comprising:

identifying the lowest yield reaction step from at least two reactions, wherein the first reaction of the at least two reactions comprises reacting the second portion of the pool of molecules of formula (IV) with the free positional building block unit B, wherein the second reaction of the at least two reactions comprises reacting a second molecule of formula (IV) with a second free positional building block unit B and a second molecule of formula (III) to form a second pool of verification molecules of formula (I), and wherein the identification of the lowest yield reaction step from at least two reactions is by calculating the synthetic yield of two or more reaction steps used to prepare a verification molecule of formula (I) from the pools of verification molecules of formula (I).

* * * * *

SEQUENCE LISTING

<160> NUMBER OF SEQ ID NOS: 4

<210> SEQ ID NO 1
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 1

Asp Tyr Lys Asp Asp Asp Asp Lys
1               5

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tttccacgct agtatgcacg                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cgtgcatact agcgtggaaa                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: dideoxyC

<400> SEQUENCE: 4
cgtgcatact agcgtggaac                                                   20
```